US005891656A

United States Patent [19]
Zarling et al.

[11] Patent Number: 5,891,656
[45] Date of Patent: *Apr. 6, 1999

[54] UP-CONVERTING REPORTERS FOR BIOLOGICAL AND OTHER ASSAYS USING LASER EXCITATION TECHNIQUES

[75] Inventors: David A. Zarling, Menlo Park, Calif.; Michel J. Rossi, Lausanne, Switzerland; Norman A. Peppers, Belmont, Calif.; James Kane, Lawrenceville, N.J.; Gregory W. Faris, Menlo Park, Calif.; Mark J. Dyer, San Jose, Calif.; Steve Y. Ng, San Francisco, Calif.; Luke V. Schneider, Half Moon Bay, Calif.

[73] Assignee: SRI International, Menlo, Calif.

[ * ] Notice: The term of this patent shall not extend beyond the expiration date of Pat. No. 5,674,698.

[21] Appl. No.: 887,428

[22] Filed: Jul. 2, 1997

Related U.S. Application Data

[63] Continuation of Ser. No. 416,023, Mar. 30, 1995, Pat. No. 5,674,698, which is a continuation-in-part of Ser. No. 381,006, Jan. 30, 1995, abandoned, which is a continuation of Ser. No. 946,068, Sep. 14, 1992, abandoned.

[51] Int. Cl.$^6$ .................................................. G01N 33/53
[52] U.S. Cl. .......................... 435/792; 435/7.21; 422/56; 422/82.08
[58] Field of Search .................................. 435/7.92, 7.21; 422/56, 82.08; 427/7

[56] References Cited

U.S. PATENT DOCUMENTS

| | | | |
|---|---|---|---|
| 3,593,055 | 7/1971 | Geusinc et al. | 313/501 |
| 3,599,109 | 8/1971 | Guggenheim et al. | 372/410 |
| 3,634,614 | 1/1972 | Geusic et al. | 348/759 |
| 4,032,351 | 6/1977 | Auzel et al. | 501/3 |
| 4,100,416 | 7/1978 | Hirshfeld et al. | 250/461.2 |
| 4,206,132 | 6/1980 | Sievers | 534/15 |
| 4,228,237 | 10/1980 | Hevey et al. | 435/5 |
| 4,492,751 | 1/1985 | Boguslaski et al. | 435/7.72 |
| 4,666,862 | 5/1987 | Chang | 436/501 |
| 4,695,393 | 9/1987 | Whitehead et al. | 252/62.54 |
| 4,710,635 | 12/1987 | Chupp | 250/461.2 |
| 4,724,217 | 2/1988 | Miller et al. | 436/82 |
| 4,727,020 | 2/1988 | Recktenwald | 435/6 |
| 4,837,169 | 6/1989 | Toner | 436/546 |
| 4,905,169 | 2/1990 | Buican et al. | 364/525 |
| 4,913,883 | 4/1990 | Imai et al. | 422/82.01 |
| 4,983,359 | 1/1991 | Tomioka et al. | 422/81 |
| 5,043,265 | 8/1991 | Tanke et al. | 435/6 |
| 5,066,580 | 11/1991 | Lee et al. | 435/7.21 |
| 5,132,242 | 7/1992 | Cheung | 436/501 |
| 5,141,740 | 8/1992 | Rajagopalan et al. | 424/9.364 |
| 5,166,948 | 11/1992 | Gavrilovic et al. | 372/70 |
| 5,185,265 | 2/1993 | Steen et al. | 436/519 |
| 5,188,942 | 2/1993 | Reddington et al. | 435/5 |
| 5,196,709 | 3/1993 | Berndt et al. | 250/458.1 |
| 5,208,651 | 5/1993 | Buican | 356/346 |
| 5,247,339 | 9/1993 | Ogino | 356/73 |
| 5,324,633 | 6/1994 | Fodor et al. | 435/6 |
| 5,399,315 | 3/1995 | Paz-Pujalt et al. | 422/56 |
| 5,436,170 | 7/1995 | Cornell et al. | 436/527 |
| 5,443,955 | 8/1995 | Cornell et al. | 435/7.21 |
| 5,514,337 | 5/1996 | Groger et al. | 422/82.08 |
| 5,599,578 | 2/1997 | Butland | 427/7 |
| 5,674,698 | 10/1997 | Zarling et al. | 435/7.92 |

FOREIGN PATENT DOCUMENTS

| | | |
|---|---|---|
| 0071859 | 2/1983 | European Pat. Off. . |
| 0174744 | 3/1986 | European Pat. Off. . |
| 0476556 | 3/1992 | European Pat. Off. . |
| 2103362 | 2/1983 | United Kingdom . |

OTHER PUBLICATIONS

Evangelista et al., "Enzyme–amplified Lanthanide Luminescence for Enzyme Detection in Bioanalytical Assays," Anal.Biol. (1991) 137:213–224.

Hemmila et al., "Europium as a Label in Time–resolved Immunofluorometric Assays," Anal.Biol. (1984) 137:335–343.

Lovgren et al., "Detection of Lanthanide Chelates by Time–resolved Fluorescence, in Nonisotopic Dna Probe Techniques" Academic Press (1992) 227–261.

Mukkala et al., "The Synthesis and Use of Activate N–benzyl Derivatives of Diethylenetriaminetetraacetic Acids: Alternative Reagents for Labeling of Antibodies with Metal Ions," Anal. Bio. (1989) 176:319–325.

P.A. Santa Cruz, et al., "Quim, Nova" (1983) 6:149–151). (Spanish article)–Title in English.

Voller, "The Enzyme Linked Immunosorbent Assay (ELISA),"in Diagnostic Horizons,(1978) 2:1:1–7.

Beverloo et al., "Preparation and microscopic visualization of multicolor luminescent immunophosphors", Cytometry (1992) 13:561–570.

B.J. Tromberg et al. "Proc. SPIE–INT" Soc. Opt. Eng., (1991) 1427:101–108.

D.C. Yeh et al., "J. Appl. Phys"., (1988) 63:4644–4650.

D.C. Yeh et al., "Phys. Rev. B", (1989) 39:80–90.

D.R. Tallant et al., J. Chem. Phys., (1975) 63:2074–2085.

Wojciechowski, et al., "Infrared–to–Blue Up–converting Phosphor", Electron Technology (1978) 11:3:31–47.

(List continued on next page.)

Primary Examiner—James C. Housel
Assistant Examiner—Ginny Allen Portner
Attorney, Agent, or Firm—Morgan, Lewis & Bockius LLP

[57] ABSTRACT

The invention provides methods, compositions, and apparatus for performing sensitive detection of analytes, such as biological macromolecules and other analytes, by labeling a probe molecule with an up-converting label. The up-converting label absorbs radiation from an illumination source and emits radiation at one or more higher frequencies, providing enhanced signal-to-noise ratio and the essential elimination of background sample autofluorescence. The methods, compositions, and apparatus are suitable for the sensitive detection of multiple analytes and for various clinical and environmental sampling techniques.

6 Claims, 32 Drawing Sheets

OTHER PUBLICATIONS

Moser, K., et al., "Infrared Spectral Distribution of Photoconductivity and Up–conversion in GaP Light Emitting Diodes", *J. Appl Phys*, (1985) 57:12:5438–5442.

Tanabe, S., et al., "Up–conversion Fluorescences of $TeO_2$– and $Ga_2O_3$– Based Oxide Glasses Containing $Er^{3+}$", Journal of Non–Crystalline Solids, (1990) 122:79–82.

Allain et al., "Room Temperature CW Tunable Green Upconversion Holmium Fibre Laser," *Electronics Letters* (1990) 26:261–263.

Allain et al., "Blue Upconversion Fluorozirconate Fibre Laser", *Electronic Letters*, (1990) 26:166–168.

Auzel, "Materials and Devices Using Double–pumped Phosphors and Energy Transfer", *Proceedings of the IEEE* (1973) 61:758–786.

Berthou and Jorgensen "Optical–fibre temperature sensor based on upconversion–excited fluorescence", *Optic Letters* (1990) 15:1100–1102.

Bethune et al., "Atoms in carbon cages: the structure and properties of endohedral fullerences", *Nature* (1993) 366:123–128.

Beverloo et al., "Inorganic phosphors as new luminscent labels for immunocytochemistry and time–resolved microscopy", *Cytometry* (1990) 11:784–792.

Camus et al., "Two–photon absorption spectroscopy in ytterbium", *J. Phys. B: Atom. Molec. Phys.* (1978) 11:L395–L397.

Campiglia, A.D. et al., "Utilization of an Inorganic Phosphor as a Reference Signal in Solid– Surface Room Temperature Phosphorimetry", *Anal. Chem.* (1988) vol. 60(g):2165–2167.

Diamandis and Christopoulos, Detection of Lanthanide Chelates and Multiple Labeling Strategies Based on Time–resolved Fluorescence, in Nonisotopic DNA Probe Techniques, *Academic Press* (1992) 263–274.

Eichstein et al., "Laser–excited Time–resolved Solid–phase Fluoroimmunoassays with the New Europium Chelate 4, 7–bis (chlorosulfophenyl)–1, 10–phenanthroline–2, 9–dicarboxylic Acid as Label," *Anal. Chem.* (1988) 60:1069–1074.

Gudgin Templeton et al., "Time Resolved Fluorescence Detection of Enzyme–amplified Lanthanide Luminescence for Nucleic Acid Hybridization Assays," *Clin. Chem.* (1991) 37/9:1509–1512.

Johnson et al., "Infrared–to–visible Conversion by Rare–earth Ions in Crystals," *J. Appl Phys.* (1972) 43:3.

Johnston and Wright, "Trace Analysis of Nonfluorescent Ions by Associate Clustering with a Fluorescent Probe," *Anal. Chem.* (1979) 51:1774–1780.

Kano et al., $NaLnF_4:YB^{3+}$,(Ln:Y,Gd,La): Efficient Green–emitting Infrared–excited Phosphors, *J. Electrochem. Soc.* (1972) 119:1561–1564.

Leif and Vallarino, "Rare–earth Chelates as Fluorescent Marks in Cell Separation and Analysis," *Cell Separation Science and Technology* (1991) 3:41–58.

Lenth and Macfarlane, *Lasers, Optics & Photonics News,* (1992) 3:8–15.

Louge et al., "Optical Fiber Measurements of Particle Velocity Using Laser–induced Phosphorescence," *Applied Optics* (1991) 30:1976–1981.

Manashirov et al., "Effect of the Purity of Initial Substances on Luminescence Intensity of Erbium in Anti–stroke Luminophores," *Chemical Abstracts,* (1989) 110:457 Abstract No. 30750B.

McFarlane, "Dual Wavelength Visible Upconversion Laser," *Appl. Phys. Letts.* (1989) 54:2301–2302.

McFarlane, "Violet Cw Neodymium Upconversion Laser," *Appl. Phys. Letts.* (1988) 54:1300–1302.

Nguyen et al., "Blue–green (450–nm) Upconversion $Tm^{3+}$:Ylf Laser," *Applied Optics* (1989) 28:3553–3555.

Rich and Pinow, Exploring the Ultimate Efficiency in Infrared–to–Visible Coverting Phosphors Activated with Er and Sensitized with Yb, *J. Appl. Phys.* (1972) 43:2357–2365.

Schindele and Renzoni, "Ultra Fluors: New Fluorophores for Immunological Applications", *J. Clin. Immun.* (1990) 13:182–186.

Seveus et al., "Time–Resolved Fluorescence Imaging of Europium chelate Label in Immunochistochemistry and in Situ Hybridization," *Cytometry* (1992) 13:329–338.

Silversmith et al., "Green Infrared–Pumped Erbium Upconversion Laser," *J. Opt. Soc. Am.* (1982) 3:128–12.

Soini and Kojola,"Time–resolved Fluorometer for Lanthanide Cachelates—a New Generation of Nonisotopic Immunoassays,"*Clin Chem.* (1983) 29/1:65–68.

Soules and Hoffman, "Luminescent Materials (Phosphors)," *Encylclopedia of Chemical Technology,* (1981) Third Edition, 14:527–545.

Tiffany, "Fluorometry, Nephelometry, and Turbidimetry," *Textbook of Clinical Chemistry,* (1986) 78–90.

Xu and Hemmila, "Co–fluorescence Enhancement System Based on Pivaloyltrifluoroacetone and Yttriuim for the Simultaneous Detection of Europium, Terbium, Samarium and Dysprosium," *Anal. Chimica Acta.* (1992) 256:9–16.

Lovgren, J. et al, Jul. 12, 1994, J. Immunol. Methods, vol. 173(1), pp. 119–125.

Beverloo et al, Cytometry, 1992, vol. 13(6), pp. 561–570.

Lovgren, T et al, Oct. 1997, vol. 43(10) pp. 1937–1943, Clinical Chemistry.

Heinonen, Petal, Clin. Chem., 1977, 43(7), pp. 1142–1150.

Evangelista, R.A et al, Analytical Biochem., vol. 197(1), 1991, pp. 213–224.

Hemmilä, I. et al, 1984, Analytical Biochem., vol. 137(2), pp. 335–343.

Xu et al, Analyst, Nov. 1991, vol. 116(11), pp. 1155–1158.

Mukkala, V.M et al., Analytical Biochem., vol. 176 #2, (Feb. 1, 1989), pp. 319–325.

Beverloo, HB et al, Anal. Biochem., Jun. 1992, vol. 203(2), pp. 326–334.

Competitive Homogeneous Assay

Competitive Homogeneous Antigen Capture Assay

UP-CONVERTING REPORTERS FOR BIOLOGICAL AND OTHER ASSAYS USING LASER EXCITATION TECHNIQUES

CONTINUING DATA

This application is a continuation of application Ser. No. 08/416,023, filed Mar. 30, 1995, now U.S. Pat. No. 5,674,698 which is a continuation-in-part of application Ser. No. 08/381,006, filed Jan. 30, 1995, now abandoned, which is a continuation of application Ser. No. 07/946,068, filed Sep. 14, 1992, now abandoned.

BACKGROUND OF THE INVENTION

The invention relates generally to detectable labels and compositions useful in assay methods for detecting soluble, suspended, or particulate substances or analytes such as proteins, carbohydrates, nucleic acids, bacteria, viruses, and eukaryotic cells and more specifically relates to compositions and methods that include luminescent (phosphorescent or fluorescent) labels.

Methods for detecting specific macromolecular species, such as proteins, drugs, and polynucleotides, have proven to be very valuable analytical techniques in biology and medicine, particularly for characterizing the molecular composition of normal and abnormal tissue samples and genetic material. Many different types of such detection methods are widely used in biomedical research and clinical laboratory medicine. Examples of such detection methods include: immunoassays, immunochemical staining for microscopy, fluorescence-activated cell sorting (FACS), nucleic acid hybridization, water sampling, air sampling, and others.

Typically, a detection method employs at least one analytical reagent that binds to a specific target macromolecular species and produces a detectable signal. These analytical reagents typically have two components: (1) a probe macromolecule, for example, an antibody or oligonucleotide, that can bind a target macromolecule with a high degree of specificity and affinity, and (2) a detectable label, such as a radioisotope or covalently-linked fluorescent dye molecule. In general, the binding properties of the probe macromolecule define the specificity of the detection method, and the detectability of the associated label determines the sensitivity of the detection method. The sensitivity of detection is in turn related to both the type of label employed and the quality and type of equipment available to detect it.

For example, radioimmunoassays (RIA) have been among the most sensitive and specific analytical methods used for detecting and quantitating biological macromolecules. Radioimmunoassay techniques have been used to detect and measure minute quantities of specific analytes, such as polypeptides, drugs, steroid hormones, polynucleotides, metabolites, and tumor markers, in biological samples. Radioimmunoassay methods employ immunoglobulins labeled with one or more radioisotopes as the analytical reagent. Radiation ($\alpha$, $\beta$, or $\gamma$) produced by decay of the attached radioisotope label serves as the signal which can be detected and quantitated by various radiometric methods.

Radioisotopic labels possess several advantages, such as: very high sensitivity of detection, very low background signal, and accurate measurement with precision radiometric instruments (scintillation and gamma counters) or with inexpensive and sensitive autoradiographic techniques. However, radioisotopic labels also have several disadvantages, such as: potential health hazards, difficulty in disposal, special licensing requirements, and instability (radioactive decay and radiolysis). Further, the fact that radioisotopic labels typically do not produce a strong (i.e., non-Cerenkov) signal in the ultraviolet, infrared, or visible portions of the electromagnetic spectrum makes radioisotopes generally unsuitable as labels for applications, such as microscopy, image spectroscopy, and flow cytometry, that employ optical methods for detection.

For these and other reasons, the fields of clinical chemistry, water and air monitoring, and biomedical research have sought alternative detectable labels that do not require radioisotopes. Examples of such non-radioactive labels include: (1) enzymes that catalyze conversion of a chromogenic substrate to an insoluble, colored product (e.g., alkaline phosphatase, $\beta$-galactosidase, horseradish peroxidase) or catalyze a reaction that yields a fluorescent or luminescent product (e.g., luciferase) (Beck and Koster (1990) *Anal. Chem.* 62: 2258; Durrant, I. (1990) *Nature* 346: 297; *Analytical Applications of Bioluminescence and Chemiluminescence* (1984) Kricka et al. (Eds.) Academic Press, London), and (2) direct fluorescent labels (e.g., fluorescein isothiocyanate, rhodamine, Cascade blue), which absorb electromagnetic energy in a particular absorption wavelength spectrum and subsequently emit visible light at one or more longer (i.e., less energetic) wavelengths.

Using enzymes and phosphorescent/fluorescent or calorimetric detectable labels offers the significant advantage of signal amplification, since a single enzyme molecule typically has a persistent capacity to catalyze the transformation of a chromogenic substrate into detectable product. With appropriate reaction conditions and incubation time, a single enzyme molecule can produce a large amount of product, and hence yield considerable signal amplification. However, detection methods that employ enzymes as labels disadvantageously require additional procedures and reagents in order to provide a proper concentration of substrate under conditions suitable for the production and detection of the colored product. Further, detection methods that rely on enzyme labels typically require prolonged time intervals for generating detectable quantities of product, and also generate an insoluble product that is not attached to the probe molecule.

An additional disadvantage of enzyme labels is the difficulty of detecting multiple target species with enzyme-labeled probes. It is problematic to optimize reaction conditions and development time(s) for two or more discrete enzyme label species and, moreover, there is often considerable spectral overlap in the chromophore end products which makes discrimination of the reaction products difficult.

Fluorescent labels do not offer the signal amplification advantage of enzyme labels, nonetheless, fluorescent labels possess significant advantages which have resulted in their widespread adoption in immunocytochemistry. Fluorescent labels typically are small organic dye molecules, such as fluorescein, Texas Red, or rhodamine, which can be readily conjugated to probe molecules, such as immunoglobulins or *Staph. aureus* Protein A. The fluorescent molecules (fluorophores) can be detected by illumination with light of an appropriate excitation frequency and the resultant spectral emissions can be detected by electro-optical sensors or light microscopy.

A wide variety of fluorescent dyes are available and offer a selection of excitation and emission spectra. It is possible to select fluorophores having emission spectra that are sufficiently different so as to permit multitarget detection and discrimination with multiple probes, wherein each probe species is linked to a different fluorophore. Because the spectra of fluorophores can be discriminated on the basis of both narrow band excitation and selective detection of emission spectra, two or more distinct target species can be detected and resolved (Titus et al. (1982) *J. Immunol. Methods* 50: 193; Nederlof et al. (1989) *Cytometry* 10: 20; Ploem, J. S. (1971) *Ann. NY Acad. Sci.* 177: 414).

Unfortunately, detection methods which employ fluorescent labels are of limited sensitivity for a variety of reasons. First, with conventional fluorophores it is difficult to discriminate specific fluorescent signals from nonspecific background signals. Most common fluorophores are aromatic organic molecules which have broad absorption and emission spectra, with the emission maximum red-shifted 50–100 nm to a longer wavelength than the excitation (i.e., absorption) wavelength. Typically, both the absorption and emission bands are located in the UV/visible portion of the spectrum. Further, the lifetime of the fluorescence emission is usually short, on the order of 1 to 100 ns. Unfortunately, these general characteristics of organic dye fluorescence are also applicable to background signals which are contributed by other reagents (e.g., fixative or serum), or autofluorescence or the sample itself (Jongkind et al. (1982) *Exp. Cell Res.* 138: 409; Aubin, J. E. (1979) *J. Histochem. Cytochem.* 27: 36). Autofluorescence of optical lenses and reflected excitation light are additional sources of background noise in the visible spectrum (Beverloo et al. (1991) *Cytometry* 11: 784; Beverloo et al. (1992) *Cytometry* 13: 561). Therefore, the limit of detection of specific fluorescent signal from typical fluorophores is limited by the significant background noise contributed by nonspecific fluorescence and reflected excitation light.

A second problem of organic dye fluorophores that limits sensitivity is photolytic decomposition of the dye molecule (i.e., photobleaching). Thus, even in situations where background noise is relatively low, it is often not possible to integrate a weak fluorescent signal over a long detection time, since the dye molecules decompose as a function of incident irradiation in the UV and near-UV bands.

However, because fluorescent labels are attractive for various applications, several alternative fluorophores having advantageous properties for sensitive detection have been proposed. One approach has been to employ organic dyes comprising a phycobiliprotein acceptor molecule dye that emits in the far red or near infrared region of the spectrum where nonspecific fluorescent noise is reduced. Phycobiliproteins are used in conjunction with accessory molecules that effect a large Stokes shift via energy transfer mechanisms (U.S. Pat. No. 4,666,862; Oi et al. (1982) *J. Cell. Biol.* 93: 891). Phycobiliprotein labels reduce the degree of spectral overlap between excitation frequencies and emission frequencies. An alternative approach has been to use cyanine dyes which absorb in the yellow or red region and emit in the red or far red where autofluorescence is reduced (Mujumbar et al. (1989) *Cytometry* 10: 11).

However, with both the phycobiliproteins and the cyanine dyes the emission frequencies are red-shifted (i.e., frequency downshifted) and emission lifetimes are short, therefore background autofluorescence is not completely eliminated as a noise source. More importantly perhaps, phycobiliproteins and cyanine dyes possess several distinct disadvantages: (1) emission in the red, far red, and near infrared region is not well-suited for detection by the human eye, hampering the use of phycobiliprotein and cyanine labels in optical fluorescence microscopy, (2) cyanines, phycobiliproteins, and the coupled accessory molecules (e.g., Azure A) are organic molecules susceptible to photobleaching and undergoing undesirable chemical interactions with other reagents, and (3) emitted radiation is down-converted, i.e., of longer wavelength(s) than the absorbed excitation radiation. For example, Azure A absorbs at 632 nm and emits at 645 nm, and allophycocyanin absorbs at 645 nm and emits at 655 nm, and therefore autofluorescence and background noise from scattered excitation light is not eliminated.

Another alternative class of fluorophore that has been proposed are the down-converting luminescent lanthanide chelates (Soini and Lovgren (1987) *CRC Crit. Rev. Anal. Chem.* 18: 105; Leif et al. (1977) *Clin. Chem.* 23: 1492; Soini and Hemmila (1979) *Clin. Chem.* 25: 353; Seveus et al. (1992) *Cytometry* 13: 329). Down-converting lanthanide chelates are inorganic phosphors which possess a large downward Stokes shift (i.e., emission maxima is typically at least 100 nm greater than absorption maxima) which aids in the discrimination of signal from scattered excitation light. Lanthanide phosphors possess emission lifetimes that are sufficiently long (i.e., greater than 1 $\mu$s) to permit their use in time-gated detection methods which can reduce, but not totally eliminate, noise caused by shorter-lived autofluorescence and scattered excitation light. Further, lanthanide phosphors possess narrow-band emission, which facilitates wavelength discrimination against background noise and scattered excitation light, particularly when a laser excitation source is utilized (Reichstein et al. (1988) *Anal. Chem.* 60: 1069). Recently, enzyme-amplified lanthanide luminescence using down-converting lanthanide chelates has been proposed as a fluorescent labeling technique (Evangelista et al. (1991) *Anal. Biochem.* 197: 213; Gudgin-Templeton et al. (1991) *Clin Chem.* 37: 1506).

Until recently, down-converting lanthanide phosphors have had the significant disadvantage that their quantum efficiency in aqueous (oxygenated) solutions is so low as to render them unsuitable for cytochemical staining. Beverloo et al. (op.cit.) have described a particular down-converting lanthanide phosphor (yttrium oxysulfide activated with europium) that produces a signal in aqueous solutions which can be detected by time-resolved methods. Seveus et al. (op.cit.) have used down-converting europium chelates in conjunction with time-resolved fluorescence microscopy to reject the signal from prompt fluorescence and thereby reduce autofluorescence. Tanke et al. (U.S. Pat. No. 5,043, 265) report down-converting phosphor particles as labels for immunoglobulins and polynucleotides.

However, the down-converting lanthanide phosphor of Beverloo et al. and the europium chelate of Seveus et al. require excitation wavelength maxima that are in the ultraviolet range, and thus produce significant sample autofluorescence and background noise (e.g., serum and/or fixative fluorescence, excitation light scattering and refraction, etc.) that must be rejected (e.g., by filters or time-gated signal rejection). Further, excitation with ultraviolet irradiation damages nucleic acids and other biological macromolecules, posing serious problems for immunocytochemical applications where it is desirable to preserve the viability of living cells and retain cellular structures (e.g., FACS, cyto-architectural microscopy).

Laser scanning fluorescence microscopy has been used for two-photon excitation of a UV-excitable fluorescent organic dye, Hoechst 33258, using a stream of strongly focused laser pulses (Denk et al. (1990) *Science* 248: 73). The organic fluorphore used by Denk et al. was significantly photobleached by the intense, highly focused laser light during the course of imaging. Motsenbocker et al. (EP 476

35 556) describes a method to increase luminol chemiluminescence by adding a dye catalyst that absorbs long wavelength radiation (deep red light) and subsequently reacts with molecular oxygen to generate an oxidant which can itself react with luminol and produce oxidized luminol which emits blue light. Gavrilovic (U.S. Pat. No. 5,166,948) discloses a method and apparatus for optical pumping of infrared pump light to a visible or ultraviolet emission light having a wavelength shorter than the pump light (i.e., up-converted emission).

Thus, there exists a significant need in the art for labels and detection methods that permit sensitive optical and/or spectroscopic detection of specific label signal(s) with essentially total rejection of nonspecific background noise, and which are compatible with intact viable cells and aqueous or airborne environments.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides labels, detection methods, and detection apparatus which permit ultrasensitive detection of cells, biological macromolecules, and other analytes, which can be used for multiple target detection and target discrimination. The up-converting labels of the invention permit essentially total rejection of non-specific background autofluorescence and are characterized by excitation and emitted wavelengths that are typically in the infrared or visible portions of the spectrum, respectively, and thus avoid the potentially damaging effects of ultraviolet radiation. The up-converting labels of the invention convert long-wavelength excitation radiation (e.g., near-IR) to emitted radiation at about one-half to one-third the wavelength of the excitation wavelength. Since background fluorescence in the visible range is negligible if near-IR excitation wavelengths are used, the use of up-converting labels provides essentially background-free detection of signal.

In brief, the invention provides the use of luminescent materials that are capable of multiphoton excitation and have upshifted emission spectra. In one embodiment of the invention, up-converting phosphors (i.e., which absorb multiple photons in a low frequency band and emit in a higher frequency band) are used as labels which can be linked to one or more probes, such as an immunoglobulin, polynucleotide, streptavidin, Protein A, receptor ligand, or other probe molecule. In an another embodiment, up-converting organic dyes serve as the label. The organic dye labels and phosphor labels of the invention are highly compatible with automated diagnostic testing, microscopic imaging applications, and coded particle detection, among many other applications.

The nature of the invention provides considerable flexibility in the apparatus for carrying out the methods. As a general matter, the excitation source may be any convenient light source, including inexpensive near-infrared laser diodes or light-emitting diodes (LEDs), and the detector may be any convenient detector, such as a photodiode. In the case of a single reporter, the apparatus includes a laser diode capable of emitting light at one or more wavelengths in the reporter's excitation band and a detector that is sensitive to at least some wavelengths in the reporter's emission band. The laser light is preferably focused to a small region in the sample, and light emanating from that region is collected and directed to the detector. An electrical signal representing the intensity of light in the emission band provides a measure of the amount of reporter present. Depending on the detector's spectral response, it may be necessary to provide a filter to block the excitation light.

Simultaneous detection of multiple reporters is possible, at least where the reporters have different excitation bands or different emission bands. Where the excitation bands differ, multiple laser diodes emitting at respective appropriate wavelengths are combined using a wavelength division multiplexer or other suitable techniques, such as frequency labeling, frequency modulation, and lock-in detector device. If the emission bands are different (whether or not the excitation bands are different), light in the different emission bands is separated and sent to multiple detectors. If the emission bands overlap, a single detector may be used, but other detection techniques are used. One example is to use time multiplexing techniques so that only one reporter is emitting at a given time. Alternatively, the different laser diodes can be modulated at different characteristic frequencies and lock-in detection performed.

Detection methods and detection apparatus of the present invention enable the ultrasensitive detection of up-converting phosphors and up-converting organic dyes by exploiting what is essentially the total absence of background noise (e.g., autofluorescence, serum/fixative fluorescence, excitation light scatter) that are advantageous characteristics of up-converting labels. Some embodiments of the invention utilize time-gated detection and/or wavelength-gated detection for optimizing detection sensitivity, discriminating multiple samples, and/or detecting multiple probes on a single sample. Phase-sensitive detection can also be used to provide discrimination between signal(s) attributable to an up-converting phosphor and background noise (e.g. autofluorescence) which has a different phase shift.

Up-converting organic dyes, such as red-absorbing dyes, also can be used in an alternate embodiment that converts the photons absorbed by the dye into a transient voltage that can be measured using electrodes and conventional electronic circuitry. After having undergone two-photon absorption the dye is ionized by additional photons from the light source (e.g., a laser) leading to short-lived molecular ions whose presence can be detected and quantified by measuring the transient photoconductivity following the excitation irradiation. In this embodiment, resonant multiphoton ionization is used to provide a quantitative measurement of the number and/or concentration of dye molecules in a sample. Furthermore, essentially all photoions formed in the irradiated sample contribute to the signal, whereas photons are emitted isotopically and only a fraction can be collected using optics. Measurement of the transient photocurrent effectively transfers the conversion of photons into an electronic signal that is readily measured with relatively simple and inexpensive sensors such as electrodes.

In some embodiments, the present invention utilizes one or more optical laser sources for generating excitation illumination of one or more discrete frequency(ies). In certain variations of the invention, laser irradiation of an up-converting label can modify the immediate molecular environment through laser-induced photochemical processes involving either direct absorption or energy transfer; such spatially-controlled deposition of energy can be used to produce localized damage and/or to probe the chemical environment of a defined location. In such embodiments, the up-converting label can preferably act as a photophysical catalyst.

The invention provides methods for producing targeted damage (e.g., catalysis) in chemical or biological materials, wherein a probe is employed to localize a linked up-converting label to a position near a targeted biological structure that is bound by the probe. The localized up-converting label is excited by one or more excitation wavelengths and emits at a shorter wavelength which may be directly cytotoxic or genotoxic (e.g., by producing free radicals such as superoxide, and/or by generating thymine-thymine dimers), or which may induce a local photolytic chemical reaction to produce reactive chemical species in the immediate vicinity of the label, and hence in the vicinity of the targeted biological material. Thus, targeting probes labeled with one or more up-converting labels (e.g., an up-converting inorganic phosphor) may be used to produce targeted damage to biological structures, such as cells, tissues, neoplasms, vasculature, or other anatomical or histological structures.

Embodiments of the present invention also include up-converting phosphors which can also be excited by an electron beam or other beam of energetic radiation of sufficient energy and are cathodoluminescent. Such electron-stimulated labels afford novel advantages in eliminating background in ultrasensitive biomolecule detection methods. Typically, stimulation of the up-converting phosphor with at least two electrons is employed to generate a visible-light or band emission.

The invention also provides for the simultaneous detection of multiple target species by exploiting the multiphoton excitation and subsequent background-free fluorescence detection of several up-converting phosphors or up-converting dyes. In one embodiment, several phosphors/dyes are selected which have overlapping absorption bands which allow simultaneous excitation at one wavelength (or in a narrow bandwidth), but which vary in emission characteristics such that each probe-label species is endowed with a distinguishable fluorescent "fingerprint." By using various methods and devices, the presence and concentration of each of the phosphors or dyes can be determined.

The invention also provides biochemical assay methods for determining the presence and concentration of one or more analytes, typically in solution. The assay methods employ compositions of probes labeled with up-converting phosphors and/or up-converting dyes and apparatus for magnetically and/or optically trapping particles that comprise the analyte and the labeled probe. In one embodiment, a sandwich assay is performed, wherein an immobilized probe, immobilized on a particle, binds to a predetermined analyte, producing an immobilization of the bound analyte on the particle; a second probe, labeled with an up-converting label can then bind to the bound analyte to produce a bound sandwich complex containing an up-converting label bound to a particle. By combining different probe-label combinations, particles of various sizes, colors, and/or shapes with distinct immobilized probe (s), and/or various excitation wavelengths, it is possible to perform multiple assays essentially simultaneously or contemporaneously. This multiplex advantage affords detection and quantitation of multiple analyte species in a single sample. The assay methods are also useful for monitoring the progress of a reaction, such as a physical, chemical, biochemical, or immunological reaction, including binding reactions. For example, the invention may be used to monitor the progress of ligand-binding reactions, polynucleotide hybridization reactions, including hybridization kinetics and thermodynamic stability of hybridized polynucleotides.

The invention also provides methods, up-converting labels, and compositions of labeled binding reagents for performing fluorescence-activated cell sorting (FACS) by flow cytometry using excitation radiation that is in the infrared portion of the spectrum and does not significantly damage cells. This provides a significant advantage over present FACS methods which rely on excitation illumination in the ultraviolet portion of the spectrum, including wavelengths which are known to produce DNA lesions and damage cells.

The invention also provides compositions comprising at least one fluorescent organic dye molecule attached to an inorganic up-converting phosphor. The fluorescent organic dye molecule is selected from the group consisting of: rhodamines, cyanines, xanthenes, acridines, oxazines, porphyrins, and phthalocyanines, and may optionally be complexed with a heavy metal. The fluorescent organic dye may be adsorbed to the inorganic up-converting phosphor crystal and/or may be covalently attached to a coated inorganic up-converting phosphor, a derivatized vitroceramic up-converting phosphor, or a microencapsulated inorganic up-converting phosphor. Frequently, covalent conjugation between the up-converting inorganic phosphor particles and proteins (e.g., avidin, immunoglobulin) can be accomplished with heterobifunctional crosslinkers.

DESCRIPTION OF SPECIFIC EMBODIMENTS

Definitions

Figure 1:
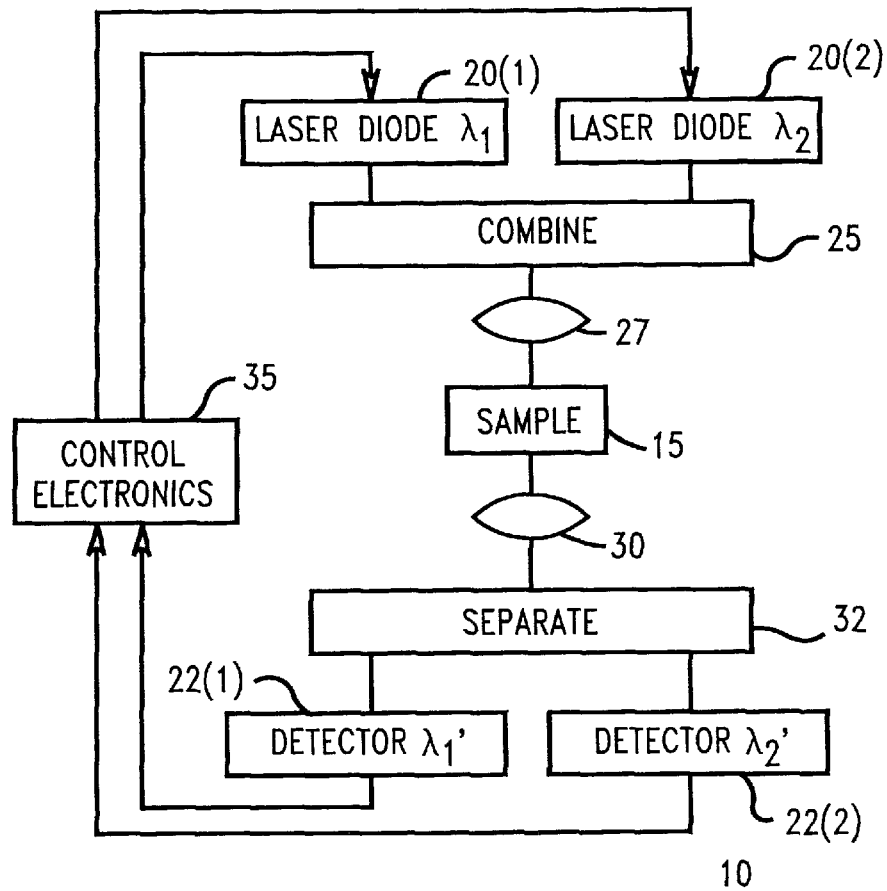
FIG. 1 is an optical and electronic block diagram illustrating representative apparatus for performing diagnostics on a sample according to the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, "label" refers to a chemical substituent that produces, under appropriate excitation conditions, a detectable optical signal. The optical signal produced by an excited label is typically electromagnetic radiation in the near-infrared, visible, or ultraviolet portions of the spectrum. The labels of the invention are up-converting labels, which means that the chemical substituent absorbs at least two photons at an excitation frequency and subsequently emits electromagnetic energy at an emission frequency higher than the excitation frequency. Thus, there is generally a significant Stokes shift between the original excitation frequency and the final emission frequency. A label is generally attached to a probe to serve as a reporter that indicates the presence and/or location of probe. The invention encompasses organic and inorganic up-converting labels, but preferably employs up-converting inorganic lanthanide phosphors as labels. Thus, a typical label of the invention is a submicron-size up-converting lanthanide phosphor particle. The label can alternatively comprise a lanthanide ion in a chelate or cage compound.

As used herein, a "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background). Generally, the probe-target binding is a non-covalent interaction with a binding affinity ($K_D$) of at least about $1 \times 10^6$ M$^{-1}$, preferably with at least about $1 \times 10^7$ M$^{-1}$, and more preferably with an affinity of at least about $1 \times 10^8$ M$^{-1}$ or greater. Antibodies typically have a binding affinity for cognate antigen of about $1 \times 10^{10}$ M$^{-1}$ or more. For example but not limitation, probes of the invention include: antibodies, polypeptide hormones, polynucleotides, streptavidin, Staphlyococcus aureus protein A, receptor ligands (e.g., steroid or polypeptide hormones), leucine zipper polypeptides, lectins, antigens (polypeptide, carbohydrate, nucleic acid, and hapten epitopes), and others.

As used herein, a "probe-label conjugate" and a "labeled probe" refer to a combination comprising a label attached to a probe. In certain embodiments, more than one label substituent may be attached to a probe. Alternatively, in some embodiments more than one probe may be attached to a label (e.g., multiple antibody molecules may be attached to a submicron-size inorganic up-converting phosphor bead). Various attachment chemistries can be employed to link a label to a probe, including, but not limited to, the formation of: covalent bonds, hydrogen bonds, ionic bonds, electrostatic interactions, and surface tension (phase boundary) interactions. Attachment of label can also involve incorporation of the label into or onto microspheres, microparticles, immunobeads, and superparamagnetic magnetic beads (Polysciences, Inc., Warrington, Pa.; Bangs Laboratories, Inc. 979 Keystone way, Carmel, Ind. 46032). For example, inorganic up-converting phosphor particles can be encapsulated in microspheres that are composed of polymer material that is essentially transparent or translucent in the wavelength range(s) of the excitation and emitted electromagnetic radiation (U.S. Pat. No. 5,132,242, incorporated herein by reference). Such microspheres can be functionalized by surface derivatization with one or more reactive groups (e.g., carboxylate, amino, hydroxylate, or polyacrolein) for covalent attachment to a probe, such as a protein. Probe-label conjugates can also comprise a phosphor chelate.

As used herein, the term "target" and "target analyte" refer to the object(s) that is/are assayed for by the methods of the invention. For example but not limitation, targets can comprise polypeptides (e.g., hGH, insulin, albumin), glycoproteins (e.g., immunoglobulins, thrombomodulin, γ-glutamyltranspeptidase; Goodspeed et al. (1989) Gene 76: 1), lipoproteins, viruses, microorganisms (e.g., pathogenic bacteria, yeasts), polynucleotides (e.g., cellular genomic DNA, RNA in a fixed histological specimen for in situ hybridization, DNA or RNA immobilized on a nylon or nitrocellulose membrane, viral DNA or RNA in a tissue or biological fluid), and pharmaceuticals (i.e., prescribed or over-the-counter drugs listed in the Physicians Drug Reference and/or Merck Manual, or illegal substances such as intoxicants or anabolic steroids).

As used herein, the term "antibody" refers to a protein consisting of one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and $F(ab')_2$, as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879–5883 (1988) and Bird et al., Science, 242, 423–426 (1988)). (See, generally, Hood et al., "Immunology", Benjamin, N. Y., 2nd ed. (1984), and Hunkapiller and Hood, Nature, 323, 15–16 (1986)). Thus, not all immunoglobulins are antibodies. (See, U.S. Ser. No. 07/634,278, which is incorporated herein by reference, and Co et al. (1991) Proc. Natl. Acad. Sci. (U.S.A.) 88: 2869, which is incorporated herein by reference).

As used herein, "probe polynucleotide" refers to a polynucleotide that specifically hybridizes to a predetermined target polynucleotide. For example but not limitation, a probe polynucleotide may be a portion of a cDNA corresponding to a particular mRNA sequence, a portion of a genomic clone, a synthetic oligonucleotide having sufficient sequence homology to a known target sequence (e.g., a telomere repeat TTAGGG or an Alu repetitive sequence) for specific hybridization, a transcribed RNA (e.g., from an SP6 cloning vector insert), or a polyamide nucleic acid (Nielsen et al. (1991) Science 254: 1497). Various target polynucleotides may be detected by hybridization of a labeled probe polynucleotide to the target sequence(s). For example but not limitation, target polynucleotides may be: genomic sequences (e.g., structural genes, chromosomal repeated sequences, regulatory sequences, etc.), RNA (e.g., mRNA, hnRNA, rRNA, etc.), pathogen sequences (e.g., viral or mycoplasmal DNA or RNA sequences), or transgene sequences.

"Specific hybridization" is defined herein as the formation of hybrids between a probe polynucleotide and a target polynucleotide, wherein the probe polynucleotide preferentially hybridizes to the target DNA such that, for example, at least one discrete band can be identified on a Southern blot of DNA prepared from eukaryotic cells that contain the target polynucleotide sequence, and/or a probe polynucleotide in an intact nucleus localizes to a discrete chromosomal location characteristic of a unique or repetitive sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., Molecular Cloning: A Laboratory Manual (1989), 2nd Ed., Cold Spring Harbor, N.Y. and Berger and Kimmel, Methods in Enzymology, Volume 152, Guide to Molecular Cloning Techniques (1987), Academic Press, Inc., San Diego, Calif., Dunn et al. (1989) J. Biol. Chem. 264: 13057 and Goodspeed et al. (1989) Gene 76: 1.

As used herein, the term "label excitation wavelength" refers to an electromagnetic radiation wavelength that, when absorbed by an up-converting label, produces a detectable fluorescent emission from the up-converting label, wherein the fluorescent emission is of a shorter wavelength (i.e., higher frequency radiation) that the label excitation wavelength. As used herein, the term "label emission wavelength" refers to a wavelength that is emitted from an up-converting label subsequent to, or contemporaneously with, illumination of the up-converting label with one or more excitation wavelengths; label emission wavelengths of up-converting labels are shorter (i.e., higher frequency radiation) than the corresponding excitation wavelengths. Both label excitation wavelengths and label emission wavelengths are characteristic to individual up-converting label species, and are readily determined by performing simple excitation and emission scans.

Invention Overview

The subject invention encompasses fluorescent labels hat are excited by an excitation wavelength and subsequently emit electromagnetic radiation at up-shifted frequencies (i.e., at higher frequencies than the excitation radiation).

In accordance with the present invention, labels comprising up-converting inorganic phosphors and/or up-converting organic dyes are provided for various applications. The up-converting labels of the invention may be attached to one or more probe(s) to serve as a reporter (i.e., a detectable marker) of the location of the probe(s). The up-converting labels can be attached to various probes, such as antibodies, streptavidin, protein A, polypeptide ligands of cellular receptors, polynucleotide probes, drugs, antigens, toxins, and others. Attachment of the up-converting label to the probe can be accomplished using various linkage chemistries, depending upon the nature of the specific probe. For example but not limitation, microcrystalline up-converting lanthanide phosphor particles may be coated with a polycarboxylic acid (e.g., Additon XW 330, Hoechst, Frankfurt, Germany) during milling and various proteins (e.g., immunoglobulin, streptavidin or protein A) can be physically adsorbed to the surface of the phosphor particle (Beverloo et al. (1991) op.cit., which is incorporated herein by reference). Alternatively, various inorganic phosphor coating techniques can be employed including, but not limited to: spray drying, plasma deposition, and derivatization with functional groups (e.g., —COOH, —NH$_2$, —CONH$_2$) attached by a silane coupling agent to —SiOH moieties coated on the phosphor particle or incorporated into a vitroceramic phosphor particle comprising silicon oxide(s) and up-converting phosphor compositions. Vitroceramic phosphor particles can be aminated with, for example, aminopropyltriethoxysilane for the purpose of attaching amino groups to the vitroceramic surface on linker molecules, however other omega-functionalized silanes can be substituted to attach alternative functional groups. Probes, such as proteins or polynucleotides may then be directly attached to the vitroceramic phosphor by covalent linkage, for example through siloxane bonds or through carbon—carbon bonds to linker molecules (e.g., organo-functional silylating agents) that are covalently bonded to or adsorbed to the surface of a phosphor particle. Covalent conjunction between the up-converting inorganic phosphor particles and proteins e.g., avidin, immunogobulin) can be accomplished with homobifunctional, or preferably heterobifunctional, crosslinkers. For example, surface slianization of the phosphors with tri(ethoxy)thiopropyl silane leaves a phosphor surface with a thiol functionality to which a protein (e.g., antibody) or any compound containing a primary amine can be grafted using conventional N-succinimidyl(4-iodoacetyl)amino-benzoate (SIAB) chemistry (Weltman et al. (1983). Other silanization and cross-linking methods compatible with the inorganic phosphors may be used at the discretion of the practitioner.

Microcrystalline up-converting phosphor particles are typically smaller than about 7 microns in diameter, preferably less than about 1 micron in diameter (i.e., submicron), and more preferably are 0.1 to 0.3 microns or less in diameter. It is generally most preferred that the phosphor particles are as small as possible while retaining sufficient quantum conversion efficiency to produce a detectable signal; however, for any particular application, the size of the phosphor particle(s) to be used should be selected at the discretion of the practitioner. For instance, some applications (e.g., detection of a non-abundant cell surface antigen) may require a highly sensitive phosphor label that need not be small but must have high conversion efficiency and/or absorption cross-section, while other applications (e.g., detection of an abundant nuclear antigen in a permeablized cell) may require a very small phosphor particle that can readily diffuse and penetrate subcellular structures, but which need not have high conversion efficiency. Therefore, the optimal size of inorganic phosphor particle is application dependent and is selected by the practitioner on the basis of quantum efficiency data for the various phosphors of the invention. Such conversion efficiency data may be obtained from available sources e.g., handbooks and published references) or may be obtained by generating a standardization curve measuring quantum conversion efficiency as a function of particle size. In some applications, such as those requiring highly sensitive detection of small phosphor particles, infrared laser diodes are preferably selected as an excitation source.

Although the properties of the up-converting phosphors will be described in detail in a later section, it is useful to outline the basic mechanisms involved. Up-conversion has been found to occur in certain materials containing rare-earth ions in certain crystal materials. For example, ytterbium and erbium act as an activator couple in a phosphor host material such as barium-yttrium-fluoride. The ytterbium ions act as the absorber, and transfer energy non-radiatively to excite the erbium ions. The emission is thus characteristic of the erbium ion's energy levels.

Up-Converting Microcrystalline Phosphors

Although the invention can be practiced with a variety of up-converting inorganic phosphors, it is believed that the preferred embodiment(s) employ one or more phosphors derived from one of several different phosphor host materials, each doped with at least one activator couple. Suitable phosphor host materials include: sodium yttrium fluoride (NaYF$_4$), lanthanum fluoride (LaF$_3$), lanthanum oxysulfide, yttrium oxysulfide, yttrium fluoride (YF$_3$), yttrium gallate, yttrium aluminum garnet, gadolinium fluoride (GdF$_3$), barium yttrium fluoride (BaYF$_5$, BaY$_2$F$_8$), and gadolinium oxysulfide. Suitable activator couples are selected from: ytterbium/erbium, ytterbium/thulium, and ytterbium/holmium. Other activator couples suitable for up-conversion may also be used. By combination of these host materials with the activator couples, at least three phosphors with at least three different emission spectra (red, green, and blue visible light) are provided. Generally, the absorber is ytterbium and the emitting center can be selected from: erbium, holmium, terbium, and thulium; however, other up-converting phosphors of the invention may contain other absorbers and/or emitters. The molar ratio of absorber: emitting center is typically at least about 1:1, more usually at least about 3:1 to 5:1, preferably at least about 8:1 to 10:1, more preferably at least about 11:1 to 20:1, and typically less than about 250:1, usually less than about 100:1, and more usually less than about 50:1 to 25:1, although various ratios may be selected by the practitioner on the basis of desired characteristics (e.g., chemical properties, manufacturing efficiency, absorption cross-section, excitation and emission wavelengths, quantum efficiency, or other considerations). The ratio(s) chosen will generally also depend upon the particular absorber-emitter couple(s) selected, and can be calculated from reference values in accordance with the desired characteristics.

The optimum ratio of absorber (e.g., ytterbium) to the emitting center (e.g., erbium, thulium, or holmium) varies, depending upon the specific absorber/emitter couple. For example, the absorber:emitter ratio for Yb:Er couples is typically in the range of about 20:1 to about 100:1, whereas the absorber:emitter ratio for Yb:Tm and Yb:Ho couples is typically in the range of about 500:1 to about 2000:1. These different ratios are attributable to the different matching energy levels of the Er, Tm, or Ho with respect to the Yb level in the crystal. For most applications, up-converting phosphors may conveniently comprise about 10–30% Yb and either: about 1–2% Er, about 0.1–0.05% Ho, or about 0.1–0.05% Tm, although other formulations may be employed.

Some embodiments of the invention employ inorganic phosphors that are optimally excited by infrared radiation of about 950 to 1000 nm, preferably about 960 to 980 nm. For example but not limitation, a microcrystalline inorganic phosphor of the formula $YF_3$:$Yb_{0.10}Er_{0.01}$ exhibits a luminescence intensity maximum at an excitation wavelength of about 980 nm. Inorganic phosphors of the invention typically have emission maxima that are in the visible range. For example, specific activator couples have characteristic emission spectra: ytterbium-erbium couples have emission maxima in the red or green portions of the visible spectrum, depending upon the phosphor host; ytterbium-holmium couples generally emit maximally in the green portion, ytterbium-thulium typically have an emission maximum in the blue range, and ytterbium-terbium usually emit maximally in the green range. For example, $Y_{0.80}Yb_{0.19}Er_{0.01}F_2$ emits maximally in the green portion of the spectrum.

Although up-converting inorganic phosphor crystals of various formulae are suitable for use in the invention, the following formulae, provided for example and not to limit the invention, are generally suitable:

$Na(Y_xYb_yEr_z)F_4$: x is 0.7 to 0.9, y is 0.09 to 0.29, and z is 0.05 to 0.01;

$Na(Y_xYb_yHo_z)F_4$: x is 0.7 to 0.9, y is 0.0995 to 0.2995, and z is 0.0005 to 0.001; and $Na(Y_xYb_yTm_z)F_4$: x is 0.7 to 0.9, y is 0.0995 to 0.2995, and z is 0.0005 to 0.001.

$(Y_xYb_yEr_z)O_2S$: x is 0.7 to 0.9, y is 0.05 to 0.12; z is 0.05 to 0.12.

$(Y_{0.86}Yb_{0/08}Er_{0.06})_2O_3$ is a relatively efficient up-converting phosphor material.

For exemplification, but not to limit the invention, ytterbium(Yb)-erbium(Er)-doped yttrium oxysulfides luminesce in the green after excitation at 950 nm. These are non-linear phosphors, in that the ytterbium acts as an "antenna" (absorber) for two 950 nm photons and transfers its energy to erbium which acts as an emitter (activator). The critical grain size of the phosphor is given by the quantum yield for green emission and the doping level of both Yb and Er, which is generally in the range of about 1 to 10 percent, more usually in the range of about 2 to 5 percent. A typical Yb:Er phosphor crystal comprises about 10–30% Yb and about 1–2% Er. Thus, a phosphor grain containing several thousand formula units ensures the emission of at least one or more photons during a typical laser irradiation time. However, the nonlinear relationship between absorption and emission indicates that intense illumination at the excitation wavelength(s) may be necessary to obtain satisfactory signal in embodiments employing very small phosphor particles (i.e., less than about 0.3 $\mu$m). Additionally, it is usually desirable to increase the doping levels of activator/emitter couples for producing very small phosphor particles so as to maximize quantum conversion efficiency.

Inorganic microcrystalline phosphors with rare earth activators generally have narrow absorption and line emission spectra. The line emission spectra are due $f$—$f$ transitions within the rare earth ion. These are shielded internal transitions which result in narrow line emission.

In certain applications, such as where highly sensitive detection is required, intense illumination can be provided by commercially available sources, such as infrared laser sources (e.g., continuous wave (CW) or pulsed semiconductor laser diodes). For example, in applications where the microcrystalline phosphor particle must be very small and the quantum conversion efficiency is low, intense laser illumination can increase signal and decrease detection times. Alternatively, some applications of the invention may require phosphor compositions that have inherently low quantum conversion efficiencies (e.g., low doping levels of activator couple), but which have other desirable characteristics (e.g., manufacturing efficiency, ease of derivatization, etc.); such low efficiency up-converting phosphors are preferably excited with laser illumination at a frequency at or near (i.e., within about 25 to 75 nm) an absorption maximum of the material. The fact that no other light is generated in the system other than from the up-converting phosphor allows for extremely sensitive signal detection, particularly when intense laser illumination is used as the source of excitation radiation. Thus, the unique property of up-conversion of photon energy by up-converting phosphors makes possible the detection of very small particles of microcrystalline inorganic phosphors. For practical implementation of phosphors as ultrasensitive reporters, particularly as intracellular reporters, it is essential that the grain size of the phosphor be as small as practicable (typically less than about 0.3 to 0.1 $\mu$m), for which laser-excited up-converting phosphors are well-suited.

For example, various phosphor material compositions capable of up-conversion are suitable for use in the invention are shown in Table I.

TABLE I

Phosphor Material Compositions

| Host Material | Absorber Ion | Emitter Ion | Color |
| --- | --- | --- | --- |
| Oxysulfides ($O_2S$) | | | |
| $Y_2O_2S$ | Ytterbium | Erbium | Green |
| $Gd_2O_2S$ | Ytterbium | Erbium | Red |
| $La_2O_2S$ | Ytterbium | Holmium | Green |
| Oxyhalides ($OX_y$) | | | |
| YOF | Ytterbium | Thulium | Blue |
| $Y_3OCl_7$ | Yterbium | Terbium | Green |
| Fluorides ($F_x$) | | | |
| $YF_3$ | Ytterbium | Erbium | Red |
| $GdF_3$ | Ytterbium | Erbium | Green |
| $LaF_3$ | Ytterbium | Holmium | Green |
| $NaYF_3$ | Ytterbium | Thulium | Blue |
| $BaYF_5$ | Ytterbium | Thulium | Blue |
| $BaY_2F_6$ | Ytterbium | Terbium | Green |
| Gallates ($Ga_xO_y$) | | | |
| $YGaO_3$ | Ytterbium | Erbium | Red |
| $Y_3Ga_5O_{12}$ | Ytterbium | Erbium | Green |
| Silicates ($Si_xO_y$) | | | |
| $YSi_2O_5$ | Ytterbium | Holmium | Green |
| $YSi_3O_7$ | Ytterbium | Thulium | Blue |

In addition to the materials shown in Table I and variations thereof, aluminates, phosphates, and vanadates can be suitable phosphor host materials. In general, when silicates are used as a host material, the conversion efficiency is relatively low. In certain uses, hybrid up-converting phosphor crystals may be made (e.g., combining one or more host material and/or one or more absorber ion and/or one or more emitter ion).

Exemplary up-converting phosphors excited at about 980 nm include, but are not limited to: $Y_{0.80}Yb_{0.18}Er_{0.02})F_3$; $Y_{0.87}Yb_{0.13}Tm_{0.001})F_3$; $Y_{0.80}Yb_{0.198}Ho_{0.002})F_3$; $Gd_{0.80}Yb_{0.18}Er_{0.02})F_3$; $Gd_{0.87}Yb_{0.13}Tm_{0.001})F_3$; $Gd_{0.80}Yb_{0.198}Ho_{0.002})F_3$; $Y_{0.86}Yb_{0.08}Er_{0.06})_2O_2S$; $Y_{0.87}Yb_{0.13}Tm_{0.001})_2O_2S$; $Y_{0.80}Yb_{0.198}Ho_{0.002})_2O_2S$; $Gd_{0.86}Yb_{0.08}Er_{0.06})_2O_2S$; $Gd_{0.87}Yb_{0.13}Tm_{0.001})_2O_2S$; $Gd_{0.80}Yb_{0.198}Ho_{0.002})_2O_2S$.

Exemplary up-converting phosphors excited at about 1500 nm include, but are not limited to: $Y_{0.96}Er_{0.06})_2O_2S$; $Gd_{0.96}Er_{0.06})_2O_2S$.

Preparation of Inorganic Phosphor Labels

Techniques and methods for manufacture of inorganic phosphors has been described in the art. Up-converting phosphor crystals can be manufactured by those of ordinary skill in the art by various published methods, including but not limited to the following: Yocom et al. (1971) *Metallurgical Transactions* 2: 763; Kano et al. (1972) *J. Electrochem. Soc.*, p. 1561; Wittke et al. (1972) *J. Appl. Physics* 43: 595; Van Uitert et al. (1969) *Mat. Res. Bull.* 4: 381; which are incorporated herein by reference. Other references which may be referred to are: Jouart J. P. and Mary G (1990) *J. Luminescence* 46: 39; McPherson G. L. and Meyerson S. L. (1991) *Chem. Phys. Lett.* (April) p. 325; Oomen et al. (1990) *J. Luminescence* 46: 353; NI H and Rand S. C. (1991) *Optics Lett.* 16 (September); McFarlane R. A. (1991) *Optics Lett.* 16 (September); Koch et al. (1990) *Appl. Phys. Lett.* 56: 1083; Silversmith et al. (1987) *Appl. Phys. Lett.* 51: 1977; Lenth W and McFarlane R. M. (1990) *J. Luminescence* 45: 346; Hirao et al. (1991) *J. Non-crystalline Solids* 135: 90; McFarlane et al. (1988) *Appl. Phys. Lett.* 52: 1300, incorporated herein by reference).

In general, inorganic phosphor particles are milled to a desired average particle size and distribution by conventional milling methods known in the art, including milling in a conventional barrel mill with zirconia and/or alumina balls for periods of up to about 48 hours or longer. Phosphor particles used in binding assays are typically about 3.0 to 0.01 $\mu$m in diameter (or along the long axis if non-spherical), more usually about 2.0 to 0.1 $\mu$m in size, and more conveniently about 1.0 to 0.3 $\mu$m in size, although phosphor particles larger or smaller than these dimensions may be preferred for certain embodiments. Phosphor particle size is selected by the practitioner on the basis of the desired characteristics and in accordance with the guidelines provided herein. Fractions having a particular particle size range may be prepared by sedimentation, generally over an extended period (i.e., a day or more) with removal or the desired size range fraction after the appropriate sedimentation time. The sedimentation process may be monitored, such as with a Horiba Particle Analyzer.

However, milling crystalline materials has several weaknesses. With milling, the particle morphology is not uniform, as milled particles result from random fracture of larger crystalline particles. Since the sensitivity of a detection assay using up-converting inorganic phosphors depends on the ability to distinguish between bound and unbound phosphor particles, it is preferable that the particles be of identical size and morphology. Size, weight, and morphology of up-converting microcrystalline phosphor particles can affect the number of potential binding sites per particle and thus the potential strength of particle binding to reporter and/or analyte. Monodisperse submicron spherical particles of uniform size can be generated by homogeneous precipitation reactions at high dilutions. For example, small yttrium hydroxy carbonate particles are formed by the hydrolysis of urea in a dilute yttrium solution. Similarly, up-converting inorganic phosphors can be prepared by homogeneous precipitation reactions in dilute conditions. For example, $(Y_{0.86}Yb_{0.08}Er_{0.06})_2O_3$ was prepared as monodisperse spherical particles in the submicron size range by precipitation.

However, after precipitation it is typically necessary to anneal the oxide in air at about 1500° C., which can cause faceting of the spherical particles which can generate aggregate formation. Faceting can be substantially reduced by converting the small spherical particles of the oxide or hydroxy carbonate precursor to the oxysulfide phase by including a polysulfide flux for annealing. Using this technique, highly efficient oxysulfide particles in the 0.3 to 0.4 $\mu$m diameter range were prepared as a dispersion in water. Frequently, sonication can be used to produce a monodisperse mixture of discrete spherical particles. After fractionation and coating, these particles can be used as up-converting reporters. Furthermore, this general preparative procedure is suitable for preparing much smaller phosphor particles (e.g., 0.1 $\mu$m diameter or smaller), which may be advantageous for various assay formats.

Frequently, such as with phosphors having an oxysulfide host material, the phosphor particles are preferably dispersed in a polar solvent, such as acetone or DMSO and the like, to generate a substantially monodisperse emulsion (e.g., for a stock solution). Aliquots of the monodisperse stock solution may be further diluted into an aqueous solution (e.g., a solution of avidin in buffered water or buffered saline).

It was found that washing phosphors in acetone or DMSO improved suspendability of inorganic phosphor particles in water. In particular, the phosphor particles prepared with polysulfide flux are preferably resuspended and washed in hot DMSO and heated for about an hour in a steam bath then allowed to cool to room temperature under continuous agitation. The phosphor particles may be pre-washed with acetone (typically heated to boiling) prior to placing the particles in the DMSO. Hot DMSO-treated phosphors were found to be reasonably hydrophilic and form stable suspensions. A Microfluidizer™ (Microfluidics Corp.) can be used to further improve the dispersion of particles in the mixture. DMSO-phosphor suspensions can be easily mixed with water, preferably with mall amounts of surfactant present. In general, olysaccharides (e.g., guar gum, xanthan gum, gum arabic, lginate, guaiac gum) can be used to promote deaggregation of particles. In a variation, particles are washed in hot DMSO and serially diluted into a 0.1% aqueous gum arabic solution, which appears to virtually eliminate water dispersion problems of phosphors.

Resuspended phosphors in organic solvent, such as DMSO, are typically allowed to settle for a suitable period (e.g., about 1–3 days), and the supernatant which is typically turbid is used for subsequent conjugation.

Ludox™ is a colloidal silica dispersion in water with a small amount of organic material (e.g., formaldehyde, glycols) and a small amount of alkali metal. Ludox™ and its equivalents can be used to coat up-converting phosphor particles which can subsequently be fired to form a ceramic silica coating which cannot be removed from the phosphor particles, but which can be readily silanized with organofunctional silanes (containing thiol, primary amine, and carboxylic acid functionalities) using standard silanization chemistries (Arkles, B, in: Silicon Compounds: Register and Review; 5th Edition (1991); Anderson, R. G., Larson, G. L., and Smith, C, eds.; p. 59–64, Huls America, Piscataway, N.J.).

Phosphor particles can be coated or treated with surface-active agents (e.g., anionic surfactants such as Aerosol OT) during the milling process or after milling is completed. For example, particles may be coated with a polycarboxylic acid (e.g., Additon XW 330, Hoechst, Frankfurt, Germany or Tamol, see Beverloo et al. (1992) op.cit.) during milling to produce a stable aqueous suspension of phosphor particles, typically at about pH 6–8. The pH of an aqueous solution of phosphor particles can be adjusted by addition of a suitable buffer and titration with acid or base to the desired pH range.

Depending upon the chemical nature of the coating, some minor loss in conversion efficiency of the phosphor may occur as a result of coating, however the power available in a laser excitation source can compensate for such reduction in conversion efficiency and ensure adequate phosphor emission.

In general, preparation of inorganic phosphor particles and linkage to binding reagents is performed essentially as described in Beverloo et al. (1992) op.cit., and Tanke U.S. Pat. No. 5,043,265. Alternatively, a water-insoluble polyfunctional polymer which exhibits glass and melt transition temperatures well above room temperature can be used to coat the up-converting phosphors in a nonaqueous medium. For example, such polymer functionalities include: carboxylic acids (e.g., 5% acrylic acid/95% methyl acrylate copolymer), amine (e.g., 5% aminoethyl acrylate/95% methyl acrylate copolymer) reducible sulfonates (e.g., 5% sulfonated polystyrene), and aldehydes (e.g., polysaccharide copolymers). The phosphor particles are coated with water-insoluble polyfunctional polymers by coacervative encapsulation in nonaqueous media, washed, and transferred to a suitable aqueous buffer solution to conduct the heterobifunctional crosslinking to a protein (e.g., antibody) or polynucleotide probe molecule. An advantage of using water-insoluble polymers is that the polymer microcapsule will not migrate from the surface of the phosphor upon aging the encapsulated phosphors in an aqueous solution (i.e., improved reagent stability). Another advantage in using copolymers in which the encapsulating polymer is only partially functionalized is that one can control the degree of functionalization, and thus the number of biological probe molecules which can be attached to a phosphor particle, on average. Since the solubility and coacervative encapsulation process will depend on the dominant nonfunctionalized component of the copolymer, the functionalized copolymer ratio can be varied over a wide range to generate a range of potential crosslinking sites per phosphor, without having to substantially change the encapsulation process.

A preferred functionalization method employs heterobifunctional crosslinkers that can be made to link the biological macromolecule probe to the insoluble phosphor particle in three steps: (1) bind the crosslinker to the polymer coating on the phosphor, (2) separate the unbound crosslinker from the coated phosphors, and (3) bind the biological macromolecule to the washed, linked polymer-coated phosphor. This method prevents undesirable crosslinking interactions between biological macromolecules and so reduces irreversible aggregation as described by Tanke et al. Examples of suitable heterobifunctional crosslinkers, polymer coating functionalities, and linkable biological macromolecules include, but are not limited to:

| Coating Functionality | Heterobifunctional Crosslinker | Biological Macromolecule |
|---|---|---|
| carboxylate | N-hydroxysuccimide 1-ethyl-3-(3-dimethylamino propyl)-carbodiimide (EDC) | Proteins (e.g., Ab, avidin) |
| primary amine | N-5-azido-2-nitrobenzoyl oxysuccimide (ANB—NOS) N-succinimidyl (4-iodoacetyl) aminobenzoate (SIAB) | All having 1° amine |
| thiol (reduced sulfonate) | N-succinimidyl (4-iodoacetyl) aminobenzoate (SIAB) | Proteins |

Binding Assays

Up-converting phosphors and up-converting organic dyes are used as reporters (i.e., detectable markers) to label binding reagents, either directly or indirectly, for use in binding assays to detect and quantitate the presence of analyte(s) in a sample. Binding reagents are labeled directly by attachment to up-converting reporters (e.g., surface adsorption, covalent linkage). Binding reagents which can be directly labeled include, but are not limited to: primary antibodies (i.e., which bind to a target analyte), secondary antibodies (i.e., which bind to a primary antibody or prosthetic group, such as biotin or digoxygenin), *Staphlococcus aureus* Protein A, polynucleotides, streptavidin, and receptor ligands. Binding reagents can also be indirectly labeled; thus, a primary antibody (e.g., a rabbit anti-erb-B antibody) can be indirectly labeled by noncovalent binding to a directly labeled second antibody (e.g., a goat anti-rabbit antibody linked to an up-converting inorganic phosphor). Quantitative detection of the analyte-probe complex may be conducted in conjunction with proper calibration of the assay for each probe employed. A probe is conveniently detected under saturating excitation conditions using, for example, a laser source or focused photodiode source for excitation illumination.

Specific binding assays are commonly divided into homogeneous and heterogeneous assays. In a homogeneous assay, the signal emitted by the bound labeled probe is different from the signal emitted by the unbound labeled probe, hence the two can be distinguished without the need for a physical separation step. In heterogeneous assays, the signal emitted from the bound and unbound labeled probes is identical, hence the two must be physically separated in order to distinguish between them. The classical heterogeneous specific binding assay is the radioimmunoassay (RIA) (Yalow et al. (1978) *Science* 200: 1245, which is incorporated herein by reference). Other heterogeneous binding assays include the radioreceptor assay (Cuatrecasas et al. (1974) *Ann. Rev. Biochem.* 43: 109), the sandwich radioimmunoassay (U.S. Pat. No. 4,376,110, which is incorporated herein by reference), and the antibody/lectin sandwich assay (EP 0 166 623, which is incorporated herein by reference). Heterogeneous assays are usually preferred, and are generally more sensitive and reliable than homogeneous assays.

Whether a tissue extract is made or a biological fluid sample is used, it is often desirable to dilute the sample in one or more diluents that do not substantially interfere with subsequent assay procedures. Generally, suitable diluents are aqueous solutions containing a buffer system (e.g., 50 mM $NaH_2PO_4$ or 5–100 mM Tris, pH4–pH10), non-interfering ionic species (5–500 mM KCl or NaCl, or sucrose), and optionally a nonionic detergent such as Tween. When the sample to be analyzed is affixed to a solid support, it is usually desirable to wash the sample and the solid support with diluent prior to contacting with probe. The sample, either straight or diluted, is then analyzed for the diagnostic analyte.

In the general method of the invention, an analyte in a sample is detected and quantified by contacting the sample with a probe-label conjugate that specifically or preferentially binds to an analyte to form a bound complex, and then detecting the formation of bound complex, typically by measuring the presence of label present in the bound complexes. A probe-label conjugate can include a directly labeled analyte-binding reagent (e.g., a primary antibody linked to an up-converting phosphor) and/or an indirectly labeled analyte-binding reagent (e.g., a primary antibody that is detected by a labeled second antibody, or a biotinylated polynucleotide that is detected by labeled streptavidin). The bound complex(es) are typically isolated from unbound probe-label conjugate(s) prior to detection of label, usually by incorporating at least one washing step, so as to remove background signal attributable to label present in unbound probe-label conjugates). Hence, it is usually desirable to incubate probe-label conjugate(s) with the analyte sample under binding conditions for a suitable binding period.

Binding conditions vary, depending upon the nature of the probe-label conjugate, target analyte, and specific assay method. Thus, binding conditions will usually differ if the probe is a polynucleotide used in an in situ hybridization, in a Northern or Southern blot, or in solution hybridization assay. Binding conditions will also be different if the probe is an antibody used in an in situ histochemical staining method or a Western blot (Towbin et al. (1979) Proc. Natl. Acad. Sci. (U.S.A.) 76: 4350, incorporated herein by reference). In general, binding conditions are selected in accordance with the general binding methods known in the art. For example, but not for limitation, the following binding conditions are provided for general guidance:

For antibody probes:
10–200 mM Tris, pH 6–8; usually 100 mM Tris pH 7.5
15–250 mM NaCl; usually 150 mM NaCl
0.01–0.5 percent, by volume, Tween 20
1 percent bovine serum albumin
4°–37° C.; usually 4° to 15° C.

For polynucleotide probes:
3–10× SSC, pH 6–8; usually 5× SSC, pH 7.5
0–50 percent deionized formamide
1–10× Denhardt's solution
0–1 percent sodium dodecyl sulfate
10–200 µg/ml sheared denatured salmon sperm DNA
20°–65° C., usually 37°–45° C. for polynucleotide probes longer than 50 bp, usually 55°–65° C. for shorter oligonucleotide probes Additional examples of binding conditions for antibodies and polynucleotides are provided in several sources, including: Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.; Young and Davis (1983) *Proc. Natl. Acad. Sci. (U.S.A.)* 80: 1194, which are incorporated herein by reference. When the probe is a receptor ligand, such as IL-2, β-interferon, or other polypeptide hormones, cytokines, or lymphokines, suitable binding conditions generally are those described in the art for performing the respective receptor-ligand binding assay.

Various examples of suitable binding conditions useful in immunoassays and immunohistochemistry are discussed, for example, in Harlow and Lane, *Antibodies: A Laboratory Manual,* Cold Spring Harbor, N.Y. (1988), which is incorporated herein by reference. In general, suitable binding conditions for immunological reactions include an aqueous binding buffer containing a salt (e.g., 5–500 mM NaCl or KCl), a buffer (e.g., Tris or phosphate buffer at pH 4–10), and optionally a nonionic detergent (e.g., Tween). in some embodiments, proteinase inhibitors or stabilizers may be included. The binding reactions are conducted for a suitable binding period, which, for antibody reactions, are typically at least about 1 to 5 minutes, preferably at least about 30 minutes to several hours, although typically less than about 24 hours, more preferably less than about a few hours or less. Binding reactions (including washes) are typically carried out a temperature range of about 0° C. to about 45° C., preferably about 4° C. to about 20°–25° C.

Binding assays, which include in situ hybridization, in situ binding assays, and immunohistochemical staining, are usually performed by first incubating the sample with a blocking or prehybridization solution, followed by incubating the sample with probe under binding conditions for a suitable binding period, followed by washing or otherwise removing unbound probe, and finally by detecting the presence, quantity, and/or location of bound probe. The step of detecting bound probe can be accomplished by detecting label, if the probe is directly labeled, or by incubating the bound complex(es) with a second binding reagent (e.g., streptavidin) that is labeled and which binds to the probe, thus accomplishing indirect labeling of the probe.

Up-converting labels are attached to probe(s) or second binding reagents that specifically or preferentially bind to probe(s) by any of the various methodologies discussed herein. Additionally, up-converting phosphor particles can be encapsulated in microspheres and coated with a probe (e.g., a specific antigen or antibody) for use as a labeled probe in an immunodiagnostic assay or nucleic acid hybridization assay to detect an analyte in a sample, such as the presence of an antibody, virus, or antigen in a blood serum sample, according to the method of Hari et al. (1990) *Biotechniques* 9: 342, which is incorporated herein by reference. Microencapsulation of phosphor can be accomplished in several ways known in the art, including coating the phosphor with a monomer solution and polymerizing the monomer to generate a polymer shell encasing the phosphor article. Phosphor particles embedded in a polymer coating, such as a gel coating, can be functionalized (e.g., with amino groups) for covalent attachment to a binding component.

Similarly, up-converting phosphor particles can be coated with probe directly, either by surface adsorption, by multiple hydrogen bonding, by electrostatic interaction, by van der Waals binding, or by covalent linkage to a functional group on a functionalized inorganic phosphor particle (e.g., a vitroceramic phosphor), for example, by linking an amino acid side-chain amine or carboxylate group of a probe protein to a carboxylate or amine group, respectively, on a functionalized phosphor particle.

In certain embodiments, such as where stearic and/or charge interference of a bulky up-converting phosphor particle inhibits binding of the linked binding reagent to a target, it is desirable to incorporate a molecular spacer between the phosphor particle and the binding reagent. For example, a derivatized microencapsulated phosphor or vitroceramic phosphor may be conjugated to a heterobifunctional reagent having a —$(CH_2)_n$— spacer, where n is usually an integer from about 2 to about 50, between terminal functional groups. Similarly, phosphors may be directly derivatized with derivatizing agents (e.g., omega-functionalized silanes) having long intramolecular spacer chains, wherein a functional group reactive with a desired binding reagent is separated from the surface of the phosphor by a spacer of usually at least about 15 Å (i.e., the equivalent of about 10 —$CH_2$— straight-chain groups). in some embodiments, labels are attached by spacer arms of various lengths to reduce potential stearic hindrance. Multiple layers of spacer arms may also be used (e.g., multiple layers of streptavidin-biotin linkages).

Multiple Analyte Detection

Since up-converting phosphors can be differentiated on the basis of the excitation and/or emission wavelength spectra, up-converting phosphors can be used to detect and discriminate multiple analyte targets, such as, for example, cell surface antigens or soluble macromolecules.

For example, streptavidin, avidin, or another linker macromolecule (e.g., antidigoxigenin antibody) are attached, respectively, to each of two different phosphors (for illustration, designated here as Phosphor#1 and Phosphor#2) which differ in their absorption and/or emission spectra so as to facilitate discrimination of the two phosphors based on absorption and/or emission wavelengths; e.g., one phosphor may emit in the blue and the other may emit in the green. For example and not limitation, Na($Y_{0.80}Yb_{0.18}Er_{0.02}$)$F_4$ emits predominantly in the green, and Na($Y_{0.73}Yb_{0.27}Tm_{0.001}$)$F_4$ emits predominantly in the blue, and thus these two phosphors may be discriminated on the basis of their phosphorescent emissions. Alternatively, two phosphors may produce essentially similar emission spectra but may have different excitation wavelengths which provide a basis for their discrimination in multiple analyte detection. A first binding component (e.g., an antibody) that binds specifically to a first analyte species (e.g., a lymphocyte CD4 antigen) and incorporates biotinyl moieties which may be bound by streptavidin-Phosphor#1 conjugates can be used to quantitatively detect the presence of a first analyte in a sample (e.g., a serum sample) by measuring phosphorescence of Phosphor#1 in analyte-binding component complexes. A second binding component (e.g., a probe polynucleotide) that binds specifically to a second analyte species (e.g., an HIV-1 sequence) and incorporates digoxygenin moieties (e.g., 11-UTP-digoxygenin) which may be bound by antidigoxigenin-Phosphor#2 conjugates can be used to quantitatively detect the presence of a second analyte in the sample by measuring phosphorescence of Phosphor#2 in analyte-binding component complexes. Thus, by simultaneously or contemporaneously detecting the presence of multiple phosphor reporters having differentiable signal characteristics, multiple analytes may be quantitatively detected in a single sample.

Sandwich Binding Assays

Up-converting phosphors labels can be used as reporters for sandwich binding assays (U.S. Pat. No. 4,376,110, which is incorporated herein by reference). For example, a magnetic bead, such as a superparamagnetic immunobead or functionalized magnetizable polymer particle (Polysciences, Inc., Warrington, Pa.), can serve as the solid substrate which has an immobilized first binding component e.g., an antibody, a polynucleotide, or a lectin) that binds to a first epitope (i.e., a binding locus: an antigenic determinant, sugar moiety, chemical substituent, or nucleotide sequence) of an analyte. The analyte binds to the first binding component and also to a second binding component (e.g., an antibody, a lectin, or a polynucleotide) which binds to a second epitope of the analyte. Thus, the analyte bridges the two binding components to form a sandwich complex which is immobilized with respect to the solid substrate. The second binding component typically has an attached or incorporated label, such as a biotinyl group which can be bound to a streptavidin-coated up-converting phosphor. Alternatively, the second binding component can be linked directly to an up-converting phosphor, such as through a covalent linkage with a functionalized vitroceramic up-converting phosphor.

The sandwich complex comprises the first binding component, an analyte, and the second binding component, which is labeled, either directly or indirectly, with an up-converting reporter. The sandwich complex is thus immobilized on the solid substrate, although the solid substrate itself may be mobile (e.g., a superparamagnetic bead circulating in a sample slurry). The presence and amount of analyte(s) can be quantitatively measured by detecting the presence of up-converting reporter in sandwich complexes.

For example, a solid substrate may have a plurality of distinct species of first binding component (e.g., an array of different oligopeptides affixed to a solid support). One or more of the species of first binding component may bind to a particular analyte (e.g., a muscarinic receptor) in an analyte solution that is in contact with the solid support. Binding of the analyte to one or more of the first binding component species may then be detected with a second binding component (e.g., an anti-muscarinic receptor antibody) labeled with an up-converting phosphor (either directly or through a biotinylated secondary antibody).

Solid substrates can be attached to a first binding component which can bind more than one distinct analyte (e.g., may be immunocrossreactive or polyspecific) and/or can be attached to multiple first binding component species which can bind multiple distinct analytes. Similarly, multiple second binding component species with binding specificities for particular analytes can be employed. When multiple second binding component species are employed, it is typically desirable to label each second binding component species with a unique up-converting label that can be distinguished on the basis of its absorption and/or emission properties.

It is possible to use different absorbers in combination with various emitters to produce a collection of phosphors having several differentiable combinations of excitation and emission spectra. For example but not limitation, six differentiable phosphors may be generated from two absorbers and three emitters. A first absorber, $A_1$, has an excitation wavelength of $\lambda_{A1}$, a second absorber, $A_2$ has an excitation wavelength of $\lambda_{A2}$, a first emitter, $E_1$, has an emission line at $\lambda_{E1}$ a second emitter, $E_2$ has an emission line at $\lambda_{E2}$, and a third emitter, $E_3$, has an emission line at $\lambda E_3$. The six phosphors may be differentiated and the signal from each individually quantitated by illuminating the sample with an excitation wavelength $\lambda_{A1}$ and detecting separately the emitted radiation at $\lambda_{E1}$, $\lambda_{E2}$, and $\lambda_{E3}$, and separately illuminating the sample with $\lambda A2$ and detecting separately the emitted radiation at $\lambda_{E1}$, $\lambda_{E2}$, and $\lambda_{E3}$. Table II shows the various absorber:emitter combinations and their excitation and emission wavelengths.

TABLE II

| Absorber:Emitter Combination | Excitation λ | Emission λ |
|---|---|---|
| A1:E1 | λA1 | λE1 |
| A1:E2 | λA1 | λE2 |
| A1:E3 | λA1 | λE3 |
| A2:E1 | λA2 | λE1 |
| A2:E2 | λA2 | λE2 |
| A2:E3 | λA2 | λE3 |

Of course, additional absorber:emitter combinations are possible to provide more than six differentiable phosphor labels.

It is also possible to utilize solid substrates of different types which may be distinguished (e.g., by size, color, density, magnetic properties, shape, charge) so that a particular type of solid substrate is associated with a particular species of first binding component.

For example and not limitation, the following three brief examples are provided to explicate further possible applications of multiple analyte sandwich assay methods.

Substrate Differentiation

The following example describes the use of distinguishable substrate types to detect the presence of specific immunoglobulin idiotypes in a sample (e.g., a blood serum sample taken from a patient) which can provide diagnostic information about the immune status of a patient (e.g., is a patient seroreactive with a particular antigen).

Large superparamagnetic beads are conjugated to an immunogenic Herpesvirus Type II envelope glycoprotein, medium-sized superparamagnetic beads are conjugated to HIV gp120 glycoprotein, and small superparamagnetic beads are conjugated to an immunogenic cytomegalovirus envelope glycoprotein. A serum sample is taken from a patient and is incubated with a mixture of the superparamagnetic beads under binding conditions to permit specific binding of immunoglobulins in the sample with the three immobilized viral glycoprotein species. The superparamagnetic beads are separated from the sample to remove non-specifically bound immunoglobulin and incubated with up-converting phosphor particles coated with *Staphylococcus aureus* Protein A, which binds to IgG, under binding conditions. Superparamagnetic beads having specifically bound IgG are thus labeled with the phosphor-Protein A conjugate. Large, medium, and small superparamagnetic beads are then separately illuminated with phosphor excitation electromagnetic radiation and time-gated emitted phosphorescence is detected. Background attributable to non-specific binding, if any, is determined and subtracted using internal standard beads (bovine serum albumin coated superparamagnetic beads) and positive and negative control serum samples. The intensity of phosphorescence associated with the large, medium, and small beads provides a measure of the amount of antibodies in the sample which are reactive with the Herpesvirus Type II envelope glycoprotein, HIV gp120 glycoprotein, and cytomegalovirus envelope glycoprotein, respectively. This information can be used to determine whether an individual patient has been infected with the HIV-1, human CMV, and/or Herpes Simplex Type II viruses.

Phosphor Differentiation

The following example describes the use of differentiable up-converting phosphors to detect the presence and relative abundance of particular isoforms of human APP (amyloid precursor protein) in a serum or brain biopsy sample. Various isoforms of APP arise in the brain as a consequence of alternative exon usage and/or alternative proteolytic processing pathways. Thus, although all APP isoforms may share a common, hypothetical epitope (X), a particular APP isoform may have a unique epitope (Y), while another APP isoform has a unique epitope (Z). it is possible that the relative abundance of a particular APP isoform in a sample may be of predictive value or may be pathognomonic for Alzheimer's Disease.

Superparamagnetic beads are conjugated to an antibody that binds specifically to a common APP epitope (X) shared by all isoforms. A specific antibody reactive with the unique Y epitope is labeled with Phosphor #1, which is excited by wavelength $\lambda_1$ and emits in a wavelength spectrum centered in the blue. A specific antibody reactive with the unique Z epitope is labeled with Phosphor #2, which is excited by a wavelength $\lambda_2$ and emits in a wavelength spectrum centered in the green. A sample containing APP isoforms is incubated with the superparamagnetic beads and labeled specific antibodies under binding conditions. The superparamagnetic beads are retrieved from the sample, either individually or in bulk. The beads are illuminated with wavelength $\lambda_1$ and blue light emission is detected and measured, and illuminated with $\lambda_2$ and green light emission is detected and measured. The intensity of $\lambda_1$-induced blue emission is a measure of the APP isoform(s) having the Y epitope, while the intensity of the $\lambda_2$-induced green emission is a measure of the APP isoform(s) having the Z epitope. If the emissions from two phosphors are readily distinguishable, $\lambda_1$ and $\lambda_2$ may be identical. The standardized relative intensities of the two phosphors provides a measure of the relative abundance of the APP isoform(s) containing the Y or Z epitopes.

Phosphor and Substrate Differentiation

The following example describes the use of differentiable up-converting phosphors in conjunction with distinguishable substrate types to detect the presence and relative abundance of particular T lymphocyte subpopulations in a blood sample taken from an individual. Although described here with reference to detecting T cell subpopulations, analyte multiplexing (i.e., detecting and/or characterizing multiple analytes in a sample by using various solid substrate types and/or up-converting phosphor labels) is believed to be a generally applicable method.

Large superparamagnetic beads are conjugated to an anti-CD4 antibody, medium-sized superparamagnetic beads are conjugated to anti-CD8 antibody, and small superparamagnetic beads are conjugated to an anti-CD28 antibody. An antibody that specifically binds to the CD2 antigen is labeled with an up-converting phosphor that has an excitation wavelength $\lambda_1$ and emits in the red. An antibody that specifically binds to the CD45R antigen is labeled with an up-converting phosphor that has an excitation wavelength $\lambda_2$ and emits in the green. An antibody that specifically binds to the CDw60 antigen is labeled with an up-converting phosphor that has an excitation wavelength $\lambda_3$ and emits in the blue.

A blood (or serum, sputum, urine, feces, biopsy tissue, etc.) sample is taken from a patient and is incubated with a mixture of the superparamagnetic beads and phosphor-labeled antibodies under binding conditions to permit specific binding of cells in the blood sample with the three bead-immobilized antibody species and the three phosphor-labeled antibody species. After antigen-antibody binding occurs, the superparamagnetic beads are segregated and examined, either sequentially or simultaneously, by illumination with $\lambda_1$, $\lambda_2$, and $\lambda_3$, and quantitative detection of red, green, and blue emissions, respectively. For example, the intensity of $\lambda_1$-induced red light emission associated with the large beads is a rough measure of the amount of cells having both CD4 and CD2 surface antigens and/or the relative abundance of those surface antigens (e.g., there may be very few CD4$^+$ cells that have CD2, but those few cells may have a large amount of CD2 antigen, and hence a large CD2 phosphorescent signal).

Similarly, the intensity of $\lambda_2$-induced green light associated with the large beads is a rough measure of the amount of cells having both CD4 and CD45R surface antigens and/or the relative abundance of those surface antigens in a sample.

In this manner, an analyte sample, such as a blood sample, can be "fingerprinted" for the presence and relative distribution(s) (e.g., cosegregation and/or correlation) of various analyte species. Such an analyte fingerprint may be used for providing diagnostic or therapeutic information, for example, as to measuring a patient's immune status or measuring response to chemotherapy directed against a particular blood cell subset. Similar analyte fingerprints can be used to type pathogenic organisms and viruses, as well as to order polynucleotide sequences for gene mapping and/or sequencing.

Superparamagnetic beads which can be differentiated based on size, shape, color, or density can be magnetically trapped individually and scanned with appropriate excitation illumination(s) and phosphor emission(s) characteristic of particular analytes detected. For example, a unitary detector can simultaneously or contemporaneously trap the superparamagnetic bead from a suspension, determine the bead type (size, shape, and/or color), and scan for presence and abundance of particular phosphors (by illuminating with excitation wavelength(s) and detecting emitted wavelengths).

By performing binding assays under dilute conditions wherein an average of one analyte or less (e.g., lymphocyte) is bound per microbead, it is possible to type cells individually (e.g., determine the abundance of CD45R on each individual CD4+ cell) and thus generate more precise lymphocyte subpopulation definitions.

Biotinylated magnetic beads can also be used to monitor the kinetics of binding streptavidin to phosphor particles and/or to segregate or purify streptavidin-coated up-converting phosphor particles from a reaction. Thus, streptavidin and up-converting phosphor particles are mixed in a reaction vessel under binding conditions for forming streptavidin-coated phosphor particles. After a suitable binding period, unbound streptavidin may be removed (e.g., by centrifugation wherein phosphor particles are collected as the pellet, unbound streptavidin in the supernatant is decanted, and the pellet is resuspended), biotinylated magnetic beads are added to the remaining phosphor suspension in binding conditions, and streptavidin-coated phosphor particles are recovered bound to the biotinylated magnetic beads.

Photophysical Catalysis by Up-Converting Phosphors

Other applications of the invention employ phosphors as a photophysical catalyst linked to a probe, where the radiation emitted by the phosphor is used, typically in conjunction with a dye molecule, to produce localized intense electromagnetic radiation in an area adjacent to the probe for various purposes other than detection (e.g., cytotoxicity, ionization of chemical species, mutagenesis, etc.). For example, an antibody that specifically binds to a cell surface antigen, such as a CD8 antigen on a $CD8^+$ lymphocyte, may be used as a probe linked to a up-converting phosphor to localize the phosphor to $CD8^+$ lymphocytes. A sample containing $CD8^+$ lymphocytes can be incubated with the anti-$CD8^+$ probe-phosphor conjugate and irradiated with an excitation wavelength (e.g., from an infrared laser diode), resulting in emission of up-shifted photons (i.e., higher frequency electromagnetic radiation) in the vicinity of $CD8^+$ lymphocytes to which the anti-$CD8^+$ probe-phosphor conjugate has bound. The emitted radiation may be of a wavelength that is directly mutagenic and/or cytotoxic (e.g., ultraviolet radiation that can lead to formation of thymine dimers, 760–765 nm light is also believed to produce chromosomal damage) or may be of a wavelength that can cause a photolytic decomposition of a chemical present in the environment, leading to local formation of reactive species that may damage adjacent cells (e.g., photodecomposition of buckminsterfullerene, $C_{60}$, to $C_{58}$ and $C_2$, may produce free radicals that may cause lipid peroxidation of cell membranes).

Since phosphor-emitted radiation is isotropic, it is generally desirable to physically separate targets (e.g., $CD8^+$ lymphocytes) from non-targets (e.g., $CD8^-$ lymphocytes) prior to excitation irradiation, so that undesirable damage to non-targets by isotropic emission(s) (i.e., "secondary damage") is avoided. Physical separation may be accomplished by various means, including but not limited to: (1) performing excitation irradiation on a dilute suspension of target and non-target cells, wherein the mean distance separating individual cells is sufficient to reduce secondary damage to non-targets, and (2) employing hydrodynamic focusing to pass cells (both targets and non-targets) single file through an illumination zone (e.g., as in a fluorescence-activated cell sorter or the like). Thus, an up-converting phosphor linked to an anti-$CD8^+$ antibody can be used to selectively damage $CD8^+$ lymphocytes in a lymphocyte sample, where (1) the phosphor emits at a wavelength that is either directly cytotoxic and/or (2) the phosphor emits at a wavelength that produces reactive chemical species by photocatalysis of a compound present in the sample (e.g., a sample can be doped with buckminsterfullerene).

Instead of using the emitted radiation directly for photocatalytic action on tissue or tumors, an excited form of oxygen, so called singlet excited oxygen ($O_2{}^1\Delta g$) can be generated by energy transfer from a dye sensitizer to dissolved molecular oxygen. This scheme makes use of the tissue penetrating power of near-infrared radiation (red and ultrared region light, including 970 nm) which reaches the inorganic up-converting phosphor. Two of the infrared photons are converted either into a red, green, or blue photon depending on the absorption spectrum of the sensitizer dye. The dye is excited by the up-converted radiation into a triplet state which transfers its energy to a dissolved molecular oxygen molecule to yield an excited (singlet) oxygen molecule. The cytotoxic activity of singlet oxygen is well documented in photodynamic therapy and other biomedical applications (see, Wagnieres et al. (19–21 Jan. 1990) *Future Directions and Applications of Photodynamic Therapy*, pp. 249, SPIE Institutes for Advanced Optical Technologies, Society of Photo-Optical Instrumentation Engineers, Box 10, Bellingham, Wash. 98277; Pelegrin et al. (1991) *Cancer* 67: 2529; Wagnieres et al. (24–25 May 1991) *Future Directions and Applications of Photodynamic Therapy*, pp. 219; Folli et al. (17 Dec. 1991) *Fluoresceine Clinique* 4; Braichotte et al. (May 1991) *ENT-Clinic,* Lausanne, Switzerland).

In this application the up-converting phosphor is mixed or laced with a sensitizing dye such as methylene blue, rose bengal or phthalocyanine derivatives, such as Zn-phthalocyanine. In the first and third case a red-emitting phosphor is used, whereas for rose bengal a green-emitting phosphor is best suited. The phthalocyanine derivatives are ideally suited for this purpose because of their total insolubility in aqueous or biological solutions. These dyes therefore stay in close proximity to the emitters so that the specificity of the cell surface-reporter/probe/dye complex becomes the limiting factor. In this case, specialized combinations of reporter/probe/dye formulations preferably in the 0.1 to 0.3-micron size range must be synthesized in order to enable efficient energy transfer: first, up-converted radiation is absorbed by the dye as completely as possible; and second, the dye excited energy (triplet state) is transferred to dissolved molecular oxygen. Both processes are very efficient if the absorption spectrum of the sensitizer dye is matched to the up-converted radiation.

This scheme presents a step beyond the traditional photodynamic therapy methods in that the red light can be used both for tracking and diagnostic as well as for therapeutic purposes after up-converting thus necessitating only one (infrared) light source at about 1000 nm. A further advantage is the greater range within biological samples of the infrared radiation compared to other known photodynamic therapy excitation schemes (750–850 nm).

For embodiments employing up-converting phosphors as photophysical catalysts, it is generally desirable that: (1) the wavelength(s) of the excitation radiation do not produce significant photocatalysis of the substrate compound, (2) the wavelength(s) of the excitation radiation are not directly cytotoxic or mutagenic, and (3) the emitted radiation is directly cytotoxic and/or is of an appropriate wavelength to produce a biologically effective amount of photodecomposition of a substrate compound (e.g., buckminsterfullerene, psoralen, compounds containing azide substituents or other photoactivated groups). Alternatively, histidine side chains of polypeptides can be oxidized by light in the presence of dye sensitizers, such as methylene blue or rose bengal (*Proteins, Structures and Molecular Principles,* (1984) Creighton (ed.), W.H. Freeman and Company, New York; *Introduction to Protein Structure,* (1991), C. Branden and J. Tooze, Garland Publishing, New York, N.Y., which are incorporated herein by reference). Thus, for example, up-converting phosphors linked to anti-CD8 antibodies can be used as photophysical catalysts to produce selective, localized damage to $CD8^+$ lymphocytes. In accordance with the invention, essentially any antibody can be linked to an appropriate up-converting phosphor, either directly or by conjugation to protein A which may then bind the immunoglobulin. Thus, the up-converting photophysical catalysts of the invention may be used to target essentially any desired antigen or cell type that can be distinguished by the presence of an identified antigen.

Up-converting Chelates

Certain applications require small reporters. For example, the transport, ability to stay in suspension, the bonding dynamics, and the tendency toward removal by microphages may be improved for smaller reporters. However, the reduced sensitivity available with smaller reporters must also be considered.

One type of small up-converting inorganic phosphor consists of rare earth ions in chelates. The use of lanthanide chelates as reporters has been developed for biological assays as described on pages 6 and 7 of this application. This prior use of lanthanide chelates involved down-conversion. That is, the emission light is at a wavelength which is longer than the excitation wavelength.

Figure 5A:
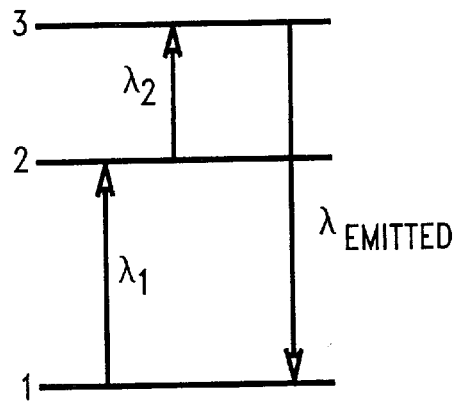
FIG. 5A, 5B, 5C show schematically energy state transitions in multi-photon excitation schemes.
Figure 5B:
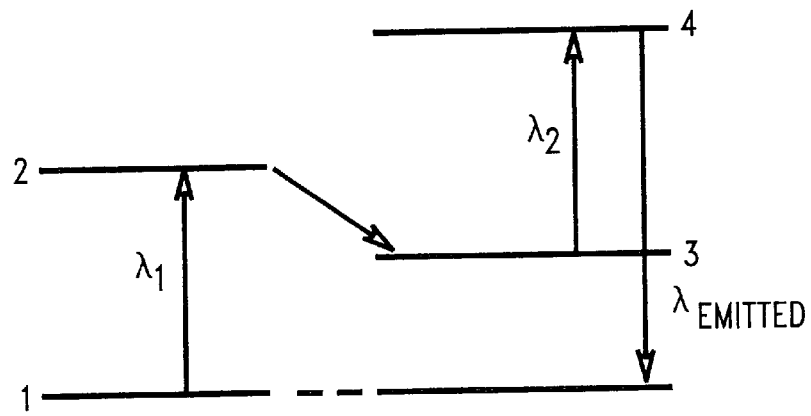

Rare earth chelates may be used as up-converting reporters through stepwise excitation such as shown in FIG. 5*a*, or in FIG. 5*b* (except that all levels would be in the same ion). Energy transfer from a sensitizer ion to an activator ion cannot be used in the case of a single rare earth ion.

Chelates suitable for use as up-converting phosphors include ethylenediaminetetraacetic acid (EDTA), dipicolinic acid (DPA), diethylenetriaminetetraacetic acid (DTTA), diethylenetriaminepentaacetic acid (DTPA), tetraazacyclotetradecanetetraacetic acid (TETA), as well as antibiotics, natural chelating proteins, phthalocyanines, and cryptates. Methods for preparation of lanthanide chelates and their use in biological assays are described in the literature (Mukkala et al. (1989) *Anal. Biochem.* 176: 319, Hemmila et al. (1984) *Anal. Biochem.* 137: 335, Soini and Kojola (1983) *Clin. Chem.* 29: 65, *Nonisotopic DNA Probe Techniques* (1992) Kricka (Ed.) Academic Press, New York, as well as the references on page 6 of this application). Up-conversion phosphor reporters can also consist of rare earth ions inside cage compounds such as fullerene materials following the procedures described by Bethune et al. (1993) *Nature* 366: 123 and references therein.

Suitable ions for up-conversion in chelates include erbium, neodymium, thulium, holmium, and praseodymium. Other candidate ions include the other lanthanide elements, the actinide elements, and other metal elements. Stepwise excitation schemes suitable for up-conversion in lanthanide chelates are described in the literature on up-conversion lasers. Examples include up-conversion in erbium (Silversmith et al. (1986) *J. Opt. Soc. Am. A*3: 128, and Macfarlane et al. (1989) *Appl. Phys. Lett.* 54: 2301), neodymium (Macfarlane et al. (1988) *Appl. Phys. Lett.* 52: 1300), thulium (Nguyen et al. (1989) *Appl. Opt.* 28: 3553 and Allain et al. (1990a) *Electron. Lett.* 226: 166), holmium (Allain et al. (1990b) *Electron. Lett.* 26: 261), and praseodymium (Smart et al. (1991) *Electron. Lett.* 27: 1307). Other up-conversion laser schemes that rely on energy transfer, energy pooling, cross relaxation, or avalanche absorption are not appropriate for up-converting chelates because they rely on energy transfer between ions. These processes are described by Auzel (1973) *Proc. IEEE* 61: 758 and Lenth and Macfarlane (March 1992) *Optics and Photonic News* 3: 8. Energy transfer can be efficient in a crystalline host containing many rare earth ions, but not in a solution where the concentration of ions is low and the phonon structure is less constrained.

In certain cases, these schemes may not function as well for up-conversion in chelates. For example, certain of the schemes have been demonstrated using crystalline host materials at very low temperatures, and may not function as well at room temperature in a chelate. Schemes that do not involve intermediate relaxation such as that of Smart et al. have advantages in chelates because they can be excited more effectively with pulsed sources. Higher peak powers can be obtained from diode lasers when they are operated in a pulsed mode. The higher peak powers lead to more efficient up-conversion due to the nonlinear dependence on excitation power.

Up-Converting Organic Dyes

Similar to the up-converting inorganic phosphor reporters we propose to use "molecular" labels whose fluorescence will be detected by optoelectronic means. Infrared or red light is exciting the probe-reporter complex bound to a target, after which light is emitted at shorter wavelengths with respect to the illuminating source. This up-converted light is free of scattered light from the source or autofluorescence by virtue of its higher energy. Furthermore, autofluorescence is greatly reduced by virtue of the excitation in the infrared or red spectral range. The light source is a pump laser whose pump pulses are short in order to achieve high powers and low energy in order to enable non-linear optical processes in the dye. The goal is to excite the second excited singlet state ($S_2$) in a dye with a ps pulse from a tunable dye laser using two red or infrared photons. After pumping the $S_2$ state the dye relaxes within a few ps to the fluorescing state ($S_1$) which can be detected by optoelectronic means. The goal of reaching the $S_2$ state using two photons enables one to take advantage of the increasing two-photon cross sections as one approaches the $S_2$ state using two-photon absorption. The non-resonant two-photon absorption cross sections are on the order of $10^{-49}$ to $10^{-50}$ $cm^4s$, whereas the cross sections corresponding to $S_2$ absorption are larger by two to three orders of magnitude. A few specific examples will be mentioned: in general cyanines, xanthenes, rhodamines, acridines and oxazines are well suited for this purpose. Blue dyes can also be used, but the excitation wavelength will be in the red. Rhodamine can be excited at 650 to 700 nm using two photons, and fluorescence is expected around 555 nm. Many IR dyes such as IR-140, IR-132 and IR-125 can be excited at 1060 nm using two photons of the Nd:YAG fundamental, and fluorescence is expected in the 850 to 950 nm range. An example of a blue dye is BBQ excited at 480 nm to reach the $S_2$ state at 240 nm, and fluorescence is expected at 390 nm. Many of these dyes are only slightly soluble in aqueous solution and are either polar in nature (cyanines) or have polar substituents. Depending on the nature of the probe, no or only minimal attachment chemistry needs to be undertaken because of the abundance of functional groups on the dye chromophore. Several companies sell entire lines of dyes: examples are KODAK, Exciton and Lambda Physik. The scientific foundations of two-photon laser excitation in organic dye molecules have been treated in a few experimental papers: A. Penzkofer and W. Leupacher, *Optical and Quantum Electronics* 19 (1987), 327–349; C. H. Chen and M. P. McCann, *Optics Commun.* 63 (1987), 335; J. P. Hermann and J. Ducuing, *Optics Commun.* 6 (1972), 101; B. Foucault and J. P. Hermann, *Optics Commun.* 15 (1975), 412; Shichun Li and C. Y. She, *Optica Acta* 29 (1982), 281–287; D. J. Bradley, M. H. R. Hutchinson and H. Koetser, *Proc. R. Soc. Lond. A* 329 (1972), 105–119.

Resonant Multiphoton Ionization

At very high laser intensities the up-converting organic dyes are induced to absorb an additional exciting photon in the field of focussed laser radiation. At those high laser Intensities the fluorescence is suppressed in favor of absorption of an additional photon. This process usually brings the organic dye molecules above the ionization limit in solution and they stabilize by emitting an electron into the solvent shell. The result of this three-photon interaction is a molecular ion and an attached or solvated electron. When this charge separation is taking place in an electric field, the charges drift and generate a voltage that can be detected in an extremely sensitive manner. This amounts to the measurement of the transient conductivity in the solvent system and is usually more sensitive than light detection. The disadvantage of this method is that it necessitates electrodes that sense the moving charges. In that sense it is not as non-invasive a method as light detection. On the other hand it bypasses the conversion of light into a photoelectric signal which represents an enormous advantage. Every optical system has a restricted viewing angle that reduces efficiency, whereas photoionization "senses" always close to 100% of the charges generated. Effectively, the non-linear interaction of the laser field converts every excited organic dye molecule into an electric pulse at sufficiently high field intensities that can be routinely achieved using commercial laser sources. Specific examples are the excitation of Rhodamine around 650 to 700 nm, or BBQ excitation around 480 nm. Organic dyes absorbing in the red have to absorb two additional photons after being excited into $S_2$ thus making the whole process a four-photon excitation process, which is slower than a three-photon non-linear process. There may, however, be circumstances where such a four-photon process is desirable.

Detection Apparatus

Detection and quantitation of inorganic up-converting phosphor(s) is generally accomplished by: (1) illuminating a sample suspected of containing up-converting phosphors with electromagnetic radiation at an excitation wavelength, and (2) detecting phosphorescent radiation at one or more emission wavelength band(s).

Illumination of the sample is produced by exposing the sample to electromagnetic radiation produced by at least one excitation source. Various excitation sources may be used, including infrared laser diodes and incandescent filaments, as well as other suitable sources. Optical filters which have high transmissibility in the excitation wavelength range(s) and low transmissibility in one or more undesirable wavelength band(s) can be employed to filter out undesirable wavelengths from the source illumination. Undesirable wavelength ranges generally include those wavelengths that produce detectable sample autofluoresence and/or are within about 25–100 nm of excitation maxima wavelengths and thus are potential sources of background noise from scattered excitation illumination. Excitation illumination may also be multiplexed and/or collimated; for example, beams of various discrete frequencies from multiple coherent sources (e.g., lasers) can be collimated and multiplexed using an array of dichroic mirrors. In this way, samples containing multiple phosphor species having different excitation wavelength bands can be illuminated at their excitation frequencies simultaneously. Illumination may be continuous or pulsed, or may combine continuous wave (CW) and pulsed illumination where multiple illumination beams are multiplexed (e.g., a pulsed beam is multiplexed with a CW beam), permitting signal discrimination between phosphorescence induced by the CW source and phosphorescence induced by the pulsed source, thus allowing the discrimination of multiple phosphor species having similar emission spectra but different excitation spectra. For example but not limitation, commercially available gallium arsenide laser diodes can be used as an illumination source for providing near-infrared light.

The ability to use infrared excitation for stimulating up-converting phosphors provides several advantages. First, inexpensive IR and near-IR diode lasers can be used for sustained high-intensity excitation illumination, particularly in IR wavelength bands which are not absorbed by water. This level of high-intensity illumination would not be suitable for use with conventional labels, such as ordinary fluorescent dyes (e.g., FITC), since high-intensity UV or visible radiation produces extensive photobleaching of the label and, potentially, damage to the sample. The ability to use higher illumination intensities without photobleaching or sample damage translates into larger potential signals, and hence more sensitive assays.

The compatibility of up-converting labels with the use of diode lasers as illumination sources provide other distinct advantages over lamp sources and most other laser sources. First, diode laser intensity can be modulated directly through modulation of the drive current. This allows modulation of the light for time-gated or phase-sensitive detection techniques, which afford sensitivity enhancement without the use of an additional modulator. Modulators require high-voltage circuitry and expensive crystals, adding both cost and additional size to apparatus. The laser diode or light-emitting diode may be pulsed through direct current modulation. Second, laser illumination sources provide illumination that is exceptionally monochromatic and can be tightly focused on very small spot sizes, which provides advantages in signal-to-noise ratio and sensitivity due to reduced background light outside of the desired excitation spectral region and illuminated volume. A diode laser affords these significant advantages without the additional expense and size of other conventional or laser sources.

Detection and quantitation of phosphorescent radiation from excited up-converting phosphors can be accomplished by a variety of means. Various means of detecting phosphorescent emission(s) can be employed, including but not limited to: photomultiplier devices, avalanche photodiode, charge-coupled devices (CCD), CID devices, photographic film emulsion, photochemical reactions yielding detectable products, and visual observation (e.g., fluorescent light microscopy). If the reporters are organic dyes, resonant multiphoton ionization can be sensed using electrostatic position-sensitive detectors. Detection can employ time-gated and/or frequency-gated light collection for rejection of residual background noise. Time-gated detection is generally desirable, as it provides a method for recording long-lived emission(s) after termination of illumination; thus, signal(s) attributable to phosphorescence or delayed fluorescence of up-converting phosphor is recorded, while short-lived autofluoresence and scattered illumination light, if any, is rejected. Time-gated detection can be produced either by specified periodic mechanical blocking by a rotating blade (i.e., mechanical chopper) or through electronic means wherein prompt signals (i.e., occurring within about 0.1 to 0.3 µs of termination of illumination) are rejected (e.g., an electronic-controlled, solid-state optical shutter such as Pockel's or Kerr cells). Up-converting phosphors and up-converting delayed fluorescent dyes typically have emission lifetimes of approximately a few milliseconds (perhaps as much as 10 ms, but typically on the order of 1 ms), whereas background noise usually decays within about 100 ns. Therefore, when using a pulsed excitation source, it is generally desirable to use time-gated detection to reject prompt signals.

Since up-converting phosphors are not subject to photobleaching, very weak emitted phosphor signals can be collected and integrated over very long detection times (continuous illumination or multiple pulsed illumination) to increase sensitivity of detection. Such time integration can be electronic or chemical (e.g., photographic film). When non-infrared photographic film is used as a means for detecting weak emitted signals, up-converting reporters provide the advantage as compared to down-converting phosphors that the excitation source(s) typically provide illumination in a wavelength range (e.g., infrared and near infrared) that does not produce significant exposure of the film (i.e., is similar to a darkroom safelight). Thus, up-converting phosphors can be used as convenient ultrasensitive labels for immunohistochemical staining and/or in situ hybridization in conjunction with fluorescence microscopy using an infrared source (e.g., a infrared laser diode) and photographic film (e.g., Kodak Ektachrome) for signal and image detection of visible range luminescence (with or without an infrared-blocking filter).

Instrumentation Overview

The basic purpose of the instrumentation is to expose the up-converting phosphor particles of an assay sample to near-infrared (NIR) light and to measure the amount of visible light that is emitted.

FIG. 1 is an optical and electronic block diagram illustrating representative apparatus 10 for performing diagnostics on a sample 15 according to the present invention. The invention may be carried out with one or a plurality of reporters. For purposes of illustration, the apparatus shows a system wherein two diagnostics are performed on a single sample in which two phosphor reporters are used. The first reporter has an excitation band centered at $\lambda_1$ and an emission band centered at $\lambda_1'$ while the second reporter has respective excitation and emission bands centered at $\lambda_2$ and $\lambda_2'$. Since the reporters of the present invention rely on multiphoton excitation, wavelengths $\lambda_1$ and $\lambda_2$ are longer than wavelengths $\lambda_1'$ and $\lambda_2'$. The former are typically in the near infrared and the latter in the visible.

A pair of light sources 20(1) and 20(2), which may be laser diodes or light-emitting diodes (LEDs), provide light at the desired excitation wavelengths, while respective detectors 22(1) and 22(2), which may be photodiodes, detect light at the desired emission wavelengths. The emitted radiation is related to the incident flux by a power law, so efficiency can be maximized by having the incident beam sharply focused on the sample. To this end, light from the two sources is combined to a single path by a suitable combination element 25, is focused to a small region by a lens or other focusing mechanism 27, and encounters the sample. Light emitted by the phosphor reporters is collected by a lens 30, and components in the two emission bands are separated by a suitable separation element 32 and directed to the respective detectors.

There are a number of possible regimes for driving the laser diodes and detecting the emitted light in the different wavelength bands. This is shown generically as a control electronics block 35 communicating with the laser diodes and detectors. The particular timing and other characteristics of the control electronics will be described below in connection with specific embodiments.

There may be a plurality of reporters having distinct emission bands but a common excitation band. In such a case, the system would include multiple detectors for a single laser diode. Similarly, there may be a plurality of reporters having distinct excitation bands but a common emission band. In such a case, the system would include multiple laser diodes for a single detector, and would use time multiplexing techniques or the like to separate the wavelengths.

Light from the two sources is shown as being combined so as to be focused at a single location by a common focusing mechanism. This is not necessary, even if it is desired to illuminate the same region of the sample. Similarly, the collection need not be via a single collection mechanism. If it is necessary to preserve all the light, the combination and separation elements can include a wavelength division multiplexer and a demultiplexer using dichroic filters. If loss can be tolerated, 50% beam splitters and filters can be used.

The schematic shows the light passing through the sample and being detected in line. As a general matter, the emission from the phosphor reporters is generally isotropic, and it may be preferred to collect light at an angle from the direction of the incident light to avoid background from the excitation source. However, since the excitation and the emission bands are widely separated, such background is unlikely to be an issue in most cases. Rather, other considerations may dictate other geometries. For example, it may be desired to detect light traveling back along the path of the incident radiation so that certain elements in the optical train are shared between the excitation and the detection paths.

A typical type of instrument with shared elements is a microscope where the objective is used to focus the excitation radiation on the sample and collect the emitted radiation. A potentially advantageous variation on such a configuration makes use of the phenomenon of optical trapping. In a situation where the reporter is bound to a small bead, it may be possible to trap the bead in the region near the beam focus. The same source, or a different source, can be used to excite the reporter. The use of an infrared diode laser to trap small particles is described in Sato et al., "Optical trapping of small particles using a 1.3 µm compact InGaAsP laser," *Optics Letters,* Vol. 16, No. 5 (Mar. 1, 1991), incorporated herein by reference.

Specific Detection Techniques

As outlined above, multichannel detection uses optical devices such as filters or dichroic beam splitters where the emission bands of the phosphor reporters are sufficiently separated. Similarly, it was pointed out that multiple reporters having a common emission band could be detected using electronic techniques. These electronic techniques will be described below in connection with multiple sources. However, the techniques will be first described in the context of a single channel. The techniques are useful in this context since there are sources of background that are in the same wavelength range as the signal sought to be measured.

Figure 2A:
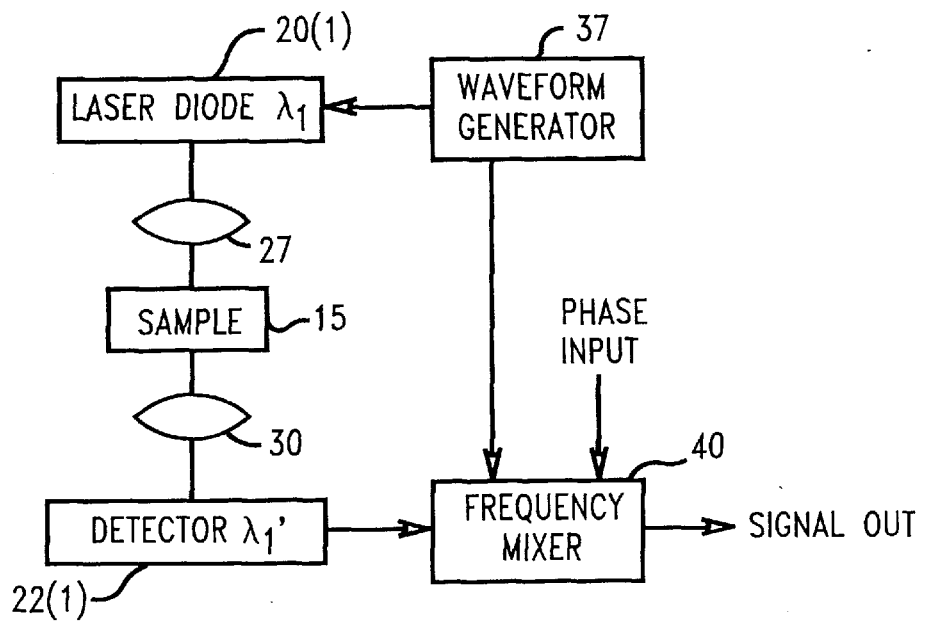
FIG. 2A shows apparatus for implementing phase sensitive detection in the context of a single channel.

FIG. 2A shows an apparatus for implementing phase sensitive detection in the context of a single channel. Corresponding reference numerals are used for elements corresponding to those in earlier described figures. In this context, control electronics 35 comprises a waveform generator 37 and a frequency mixer 40. Waveform generator 37 drives laser diode 20(1) at a frequency $f_1$, and provides a signal at $f_1$ to the frequency mixer. The frequency mixer also receives the signal from detector 22(1) and a phase control input signal. This circuitry provides additional background discrimination because the background has a much shorter lifetime than the signal sought to be measured (nanoseconds or microseconds compared to milliseconds). This causes the signal and background to have different phases (although they are both modulated at the characteristic frequency of the waveform generator). For a discussion of the lifetime-dependent phase shift, see Demtröder, *Laser Spectroscopyy* Springer-Verlag, New York, 1988, pp. 557–559, incorporated herein by reference). The phase input signal is controlled to maximize the signal and discriminate against the background. This background discrimination differs from that typical for phase sensitive detection where the signal is modulated and the background is not. Discrimination against unmodulated background is also beneficial here, leading to two types of discrimination.

Figure 2B:
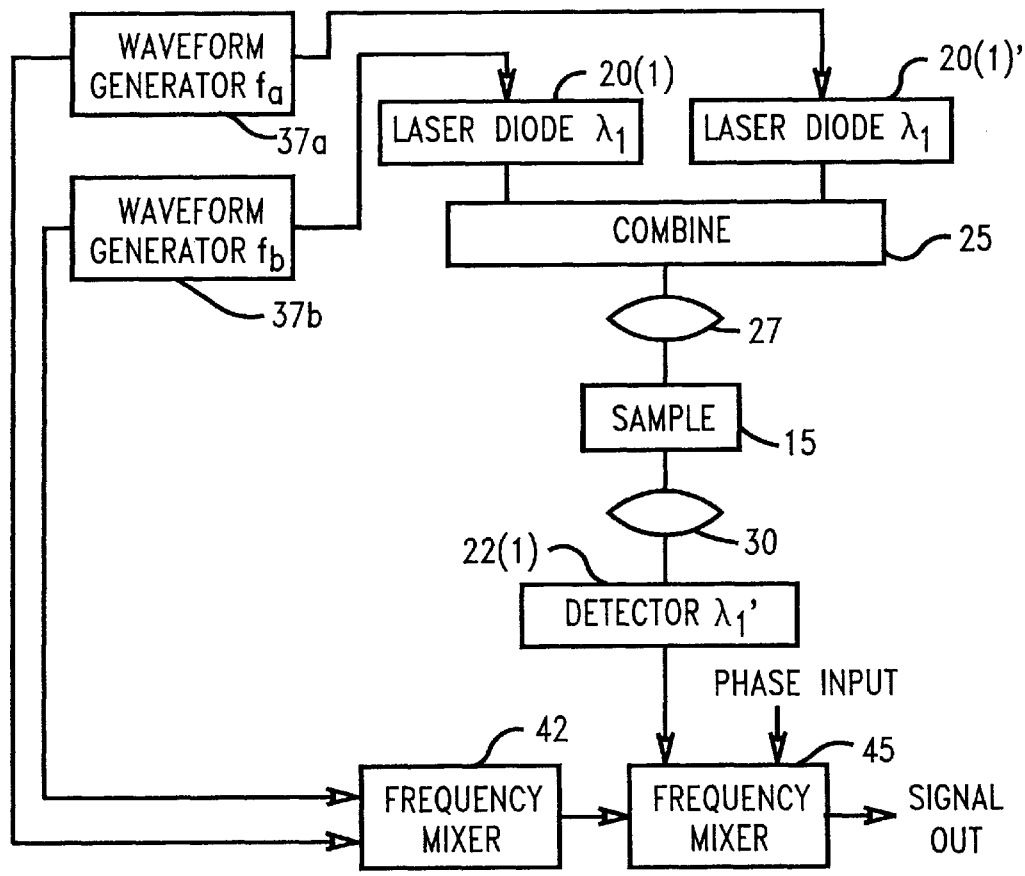
FIG. 2B shows apparatus where first and second laser diodes are modulated by signals from waveform generators.

Because the signal relies on two-photon excitation, it is possible to use two modulated laser diodes and to detect the signal at the sum or difference of the modulation frequencies. FIG. 2B shows such an arrangement where first and second laser diodes 20(1) and 20(1)' (emitting at the same wavelength $\lambda_1$, or possibly different wavelengths) are modulated by signals from waveform generators 37a and 37b operating at respective frequencies $f_a$ and $f_b$. The waveform generator output signals are communicated to a first frequency mixer 42, and a signal at $f_a \pm f_b$ is communicated to a second frequency mixer 45. The signal from detector 22(1) and a phase input signal are also communicated to frequency mixer 45.

Figure 3:
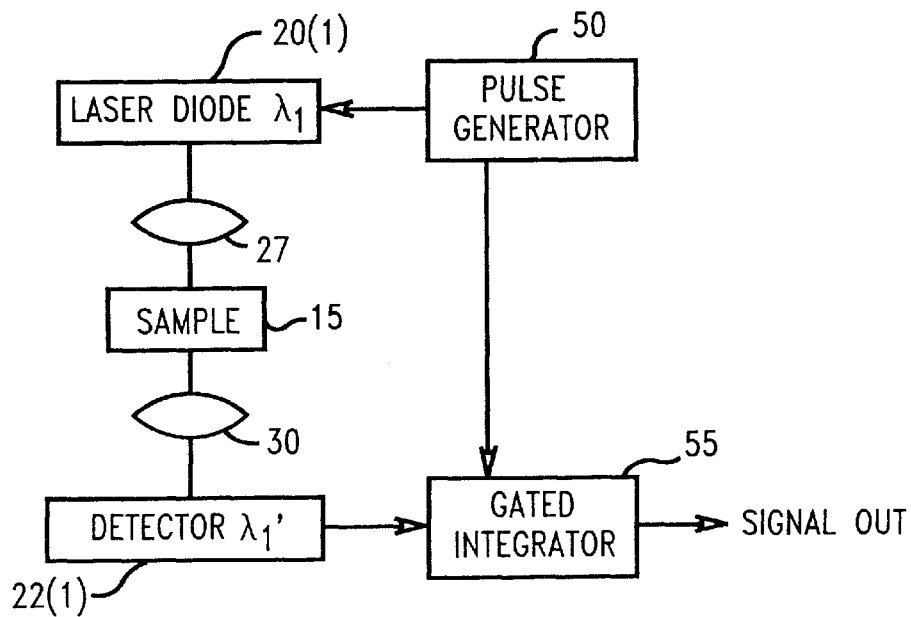
FIG. 3 shows apparatus for performing gated detection.

FIG. 3 shows apparatus for performing gated detection. Since the background is shorter-lived than the signal, delaying the detection allows improved discrimination. To this end, the laser diode is driven by a pulse generator 50, a delayed output of which is used to enable a gated integrator or other gated analyzer 55.

Figure 4:
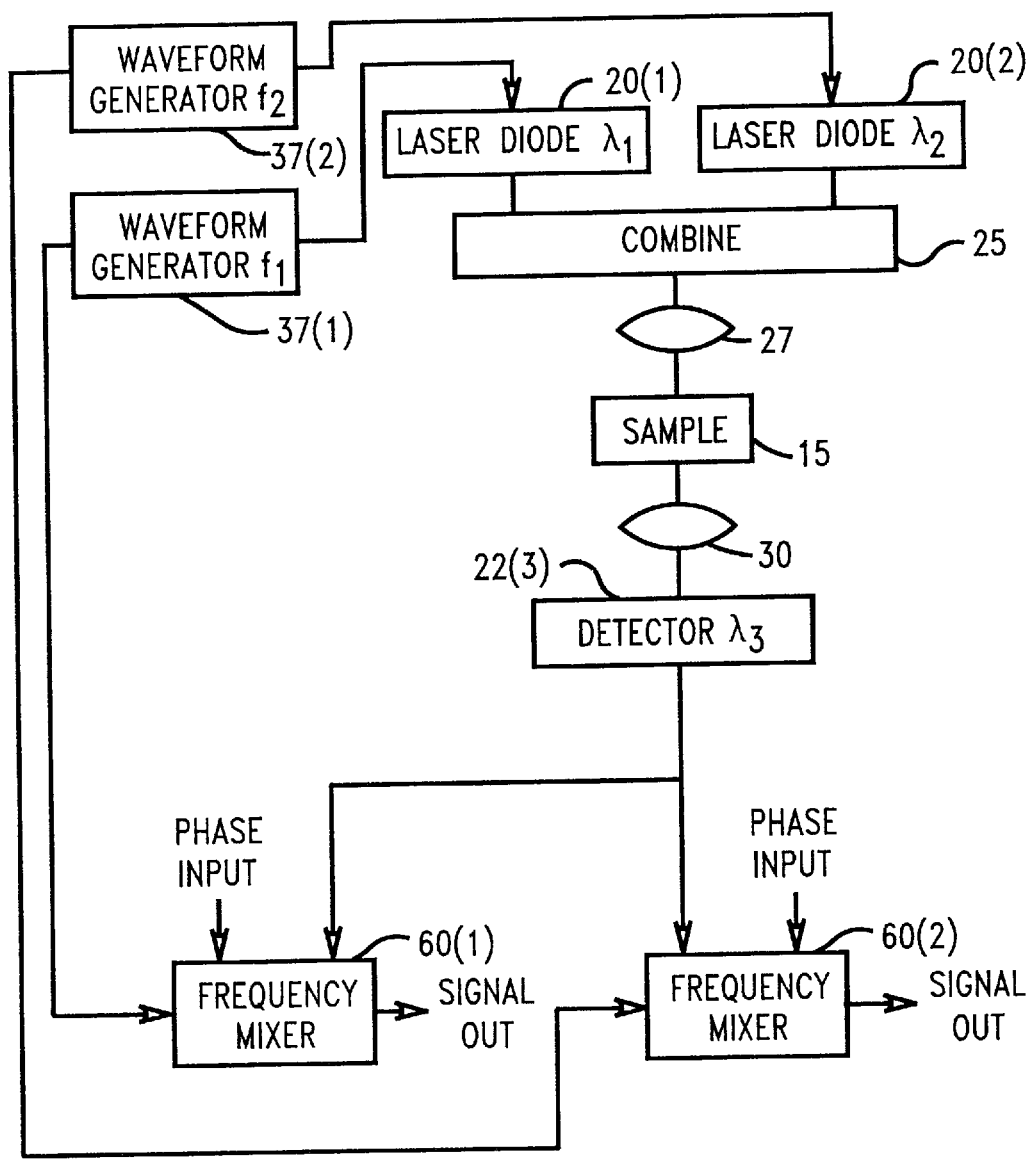
FIG. 4 shows an apparatus for performing diagnostics on a sample using first and second reporters excitation bands centered at $\lambda_1$ and $\lambda_2$, respectively, and having overlapping emission bands near $\lambda_3$.

FIG. 4 shows an apparatus for performing diagnostics on a sample using first and second, reporters having excitation bands centered at $\lambda_1$ and $\lambda_2$, and having overlapping emission bands near $\lambda_3$. The sample is irradiated by light from laser diodes 20(1) and 20(2) as discussed above in connection with FIG. 1. First and second waveform generators 37(1) and 37(2) drive the laser diodes at respective frequencies $f_1$ and $f_2$, and further provide signals at $f_1$ and $f_2$ to respective frequency mixers 60(1) and 60(2). The signal from detector 22(3) is communicated to both frequency mixers, which also receive respective phase input signals. Thus, frequency mixer 60(1) provides an output signal corresponding to the amount of emitted light modulated at frequency $f_1$, which provides a measure of the presence of the first reporter in the sample. Similarly, frequency mixer 60(2) provides an output signal corresponding to the amount of emitted light modulated at frequency $f_2$, which provides a measure of the presence of the second reporter in the sample.

The use of two different wavelengths was discussed above in the context of two reporters having different excitation bands. However, the discussion is germane to a single reporter situation as well. Since the excitation is a two-photon process, there is no requirement that the two photons have the same energy. Rather, it is only necessary that the total energy of the two photons fall within the excitation band. Thus, since it is relatively straightforward and inexpensive to provide different wavelengths with laser diodes, there are more possible combinations, i.e., more possible choices of total excitation energy. This allows more latitude in the choice of rare earth ions for up-converters since the excitation steps need not rely on energy transfer coincidences involving a single photon energy. Further, it may be possible to achieve direct stepwise excitation of the emitting ion (the erbium ion in the example outlined above) without using energy transfer from another absorbing ion (the ytterbium ion in the example) while taking advantage of resonant enhancement of intermediate levels. Additionally, the use of different wavelengths for a single reporter can provide additional options for excitation-dependent multiplexing and background discrimination techniques.

Figure 5C:
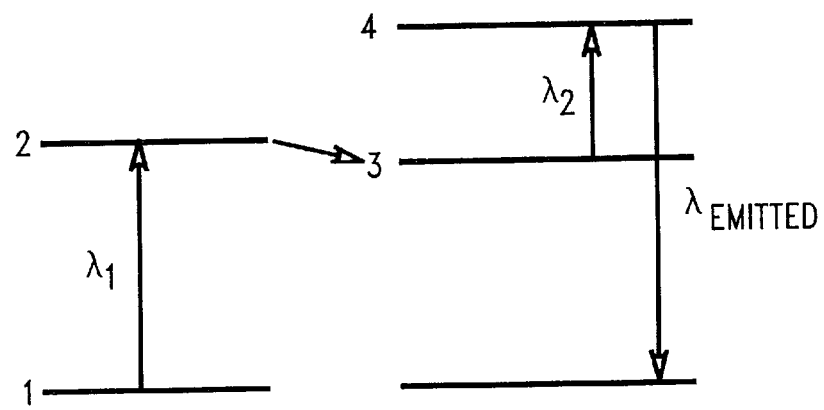
Figure 6:
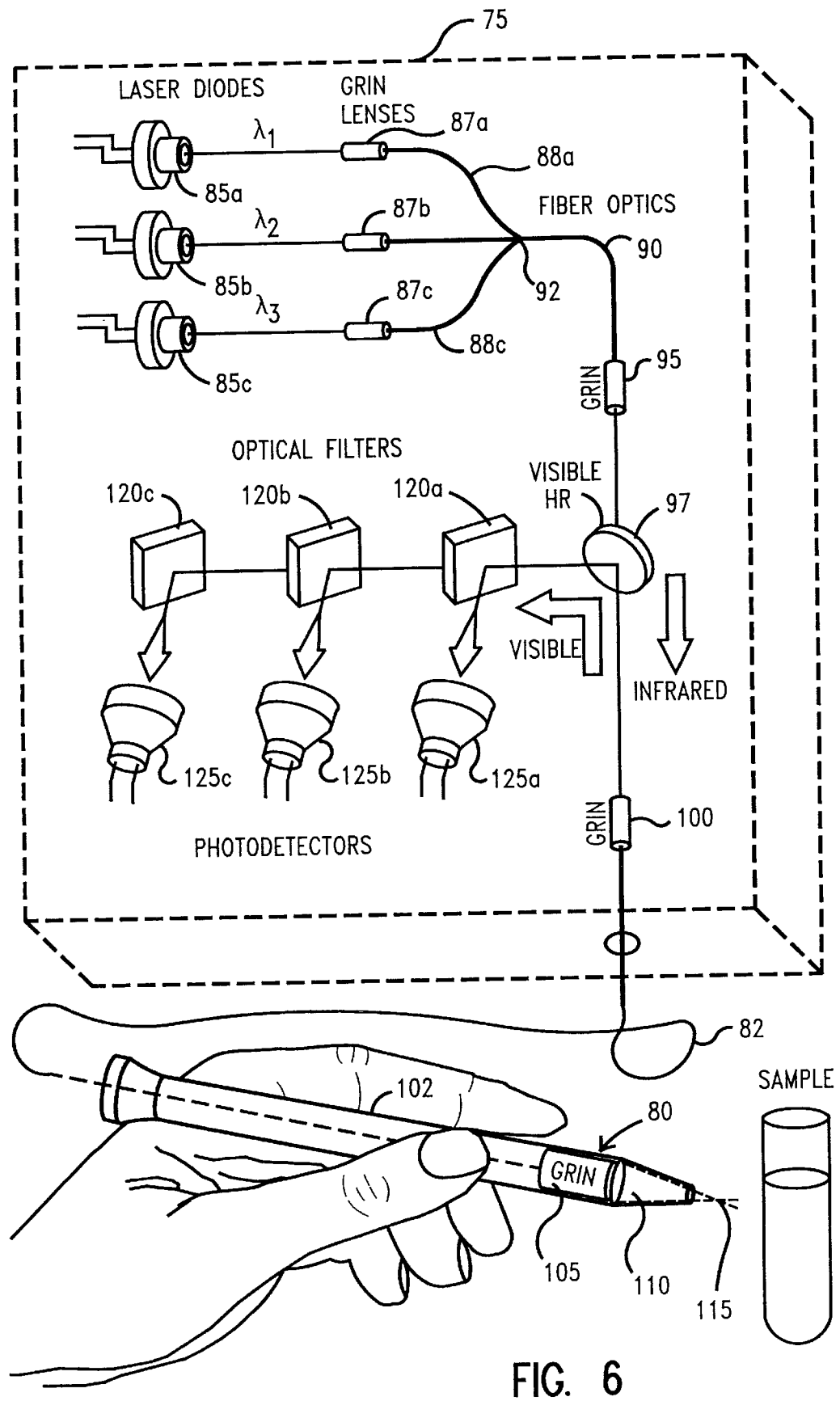
FIG. 6 shows a miniaturized instrument using a hand-held probe.

Multiple wavelength excitation of a single phosphor may occur in a number of ways, as shown in FIGS. 5A through 5C. Two lasers may cause stepwise excitation of a single ion, as shown in FIG. 5A. A first laser stimulates excitation from level 1 to level 2, and a second laser stimulates excitation from level 2 to level 3, at which level emission occurs. Single ion excitation can also occur using energy transfer as shown in FIG. 5B. In this case, a first laser stimulates excitation from level 1 to level 2, energy transfer occurs from level 2 to level 3, and a second laser stimulates excitation from level 3 to level 4. In a variation of the latter process, levels 1 and 2 can be in a first ion (i.e., a sensitizer ion) and levels 3 and 4 in a second ion (i.e., activator ion) as shown in FIG. 5C.

In a stepwise excitation scheme shown in FIG. 5A, energy transfer is not required, and thus information on the polarization of the excitation lasers may be preserved and cause polarization of the emitted radiation. In this case, depolarization of the light may allow for enhanced discrimination between signal and background noise.

For the multi-ion multi-laser excitation scheme shown in FIG. 5C, there may be several phosphors that share a common excitation wavelength. In this case, discrimination between different phosphors may be performed on the basis of different emission wavelengths and/or through time-gated, frequency-modulated, and/or phase-sensitive detection utilizing modulation of the excitation wavelength(s).

Specific Instrument Embodiments

FIG. 5 is a schematic view showing the optical train of a particular embodiment of apparatus for carrying out the present invention on a sample using a hand-held probe. This embodiment takes the form of a miniaturized instrument comprising a housing 75 (shown in phantom), a hand-held probe 80, with a fiber optic connecting cable 82. The optical and electronics components are located within the housing. For purposes of illustration, the optical components of a 3-channel system are shown. The sample may contain up to three reporters having distinct emission bands, for example, in the blue, green, and red portions of the visible spectrum. It is also assumed that the reporters have distinct excitation bands in the near infrared.

The output beams from three laser diodes 85a–c are communicated through graded index (GRIN) lenses 87a–c, focused onto the ends of respective fiber segments 38a–c and coupled into a single fiber 90 by a directional coupler 92 or other suitable device. The light emerging from the end of fiber 90 is collimated by a GRIN lens 95, passes through a dichroic beam splitter 97, and is refocused by a GRIN lens 100 onto the end of fiber optic cable 82. The beam splitter is assumed to pass the infrared radiation from the laser diodes but reflect visible light.

Hand-held probe 80 includes a handpiece 102, an internal GRIN lens 105, and a frustoconical alignment tip 110. The light emerging from fiber 82 is focused by GRIN lens 105 at a focus point 115 that is slightly beyond alignment tip 110. The alignment tip is brought into proximity with the test tube holding the sample so that focus point 115 is in the sample. It is assumed that the test tube is transmissive to the laser radiation.

A portion of the light emanating from the region of focus point 115 in the sample is collected by GRIN lens 105, focused into fiber 82, collimated by GRIN lens 100, and reflected at dichroic beam splitter 97. This light may contain wavelengths in up to the three emission bands. Optical filters 120a–c direct the particular components to respective photodetectors 125a–c. A particular filter arrangement is shown where each filter reflects light in a respective emission band, but other arrangements would be used if, for example, one or more of the filters were bandpass filters for the emission bands.

The control electronics are not shown, but could incorporate the time-multiplexed or heterodyne techniques discussed above. Such techniques would be necessary, for example, if the emission bands were not distinct.

Figure 7A:
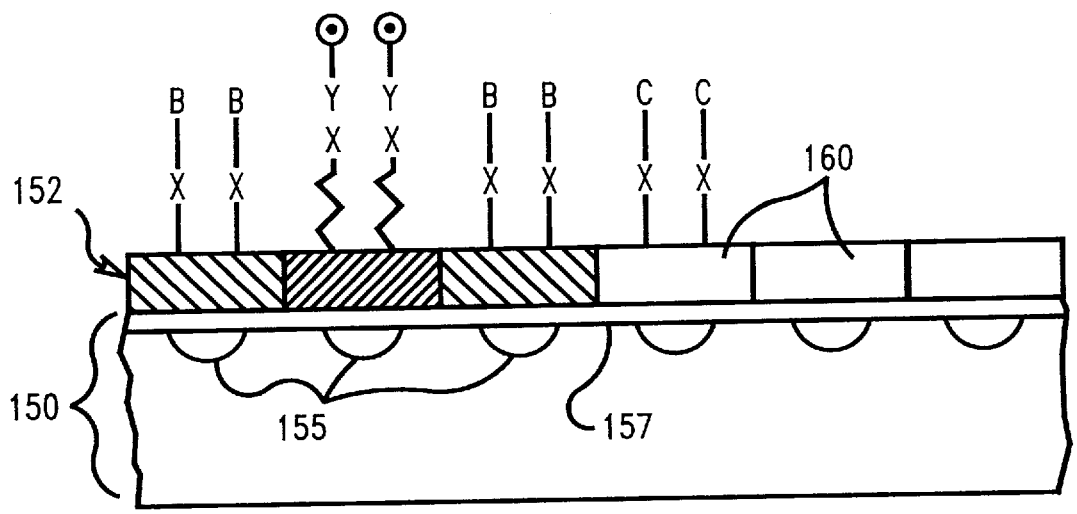
FIG. 7A shows the use of a charge-coupled device (CCD) array used to detect emissions from a large plurality of binding sites.

FIG. 7A is a schematic of an embodiment of the invention in which a charge coupled device (CCD) imaging array 150 is used as a detector in combination with a two dimensional array 152 of peptides or other biologically active species deposited on a glass or plastic substrate. The CCD array has a number of individually addressable photosensitive detector elements 155 with an overlying passivation layer 157 while the peptide array has a number of individual binding sites 160. The probe containing the phosphor would be reaction specific to one or more of the elements in this peptide array and would therefore become physically attached to those elements and only those elements. The peptide array is shown as having a one-to-one geometric relation to the imaging array in which one pixel corresponds to each element in the peptide array. However, it is also possible to have larger peptide elements that cover a group of detector elements should such be necessary.

Various of the techniques described above can be used to enable the detector array to distinguish the emissions of the phosphor from the infrared laser stimulation.

First, it is possible to use a phosphor that responds to IR stimulation beyond the sensitivity range of the detector array. An example of such a phosphor would be Gadolinium oxysulfide: 10% Erbium. This phosphor is stimulated by 1.5-micron radiation and emits at 960 nm and 520 nm. The detector array is insensitive to 1.5-micron radiation but is sensitive to the up-converted radiation.

Further, since the phosphor emission is relatively slow in rise and fall time it could be time resolved from a pulsed laser stimulation source by the CCD detector array. The decay time for the upconversion process is a variable dependent on the particular emitting transition and the phosphor host; however, it is normally in the range 500 $\mu$s seconds to 10 ms. This is very slow compared to the laser excitation pulse and the capability of the detector array.

The techniques for fabricating the CCD array are well-known since CCD imaging arrays have been commercially available for many years. A variety of such devices can be obtained from David Sarnoff Research Center, Princeton, N.J.

The techniques for fabricating the peptide array are described in a paper by Fodor et al., "Light-Directed, Spatially Addressable Parallel Chemical Synthesis," *Science*, Vol. 251, pp. 767–773 (Feb. 15, 1991), incorporated herein by reference. The particular array described contains 1024 discrete elements in a 1.28 cm×1.28 cm area.

Figure 7B:
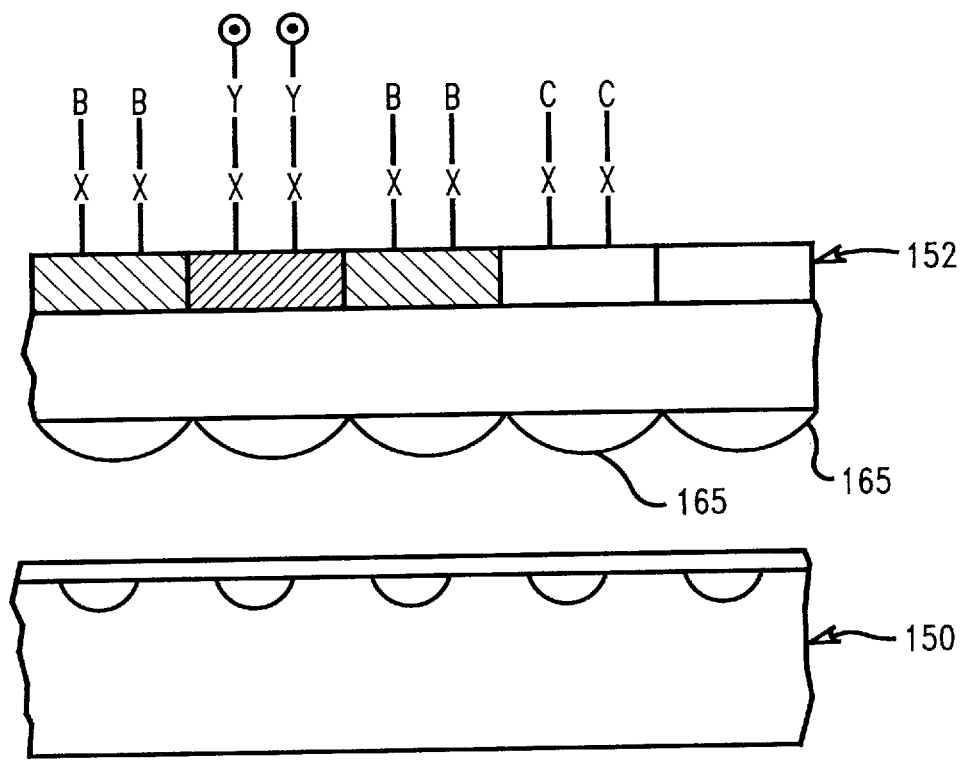
FIG. 7B shows the CCD array used in conjunction with a lens array.

The embodiment of FIG. 7A shows the peptide array in intimate contact with the CCD array. Indeed it may be possible to deposit the peptides directly on the passivation layer without a separate substrate. However, there may be situations where spatially separated arrays are preferred FIG. 7B shows an embodiment where the peptide array and the CCD array are separated. An array of lenses 165 collect the light from respective binding sites and focus it on respective detector elements. This arrangement facilitates the use of filters to the extent that other techniques for rejecting the excitation radiation are not used.

Figure 8:
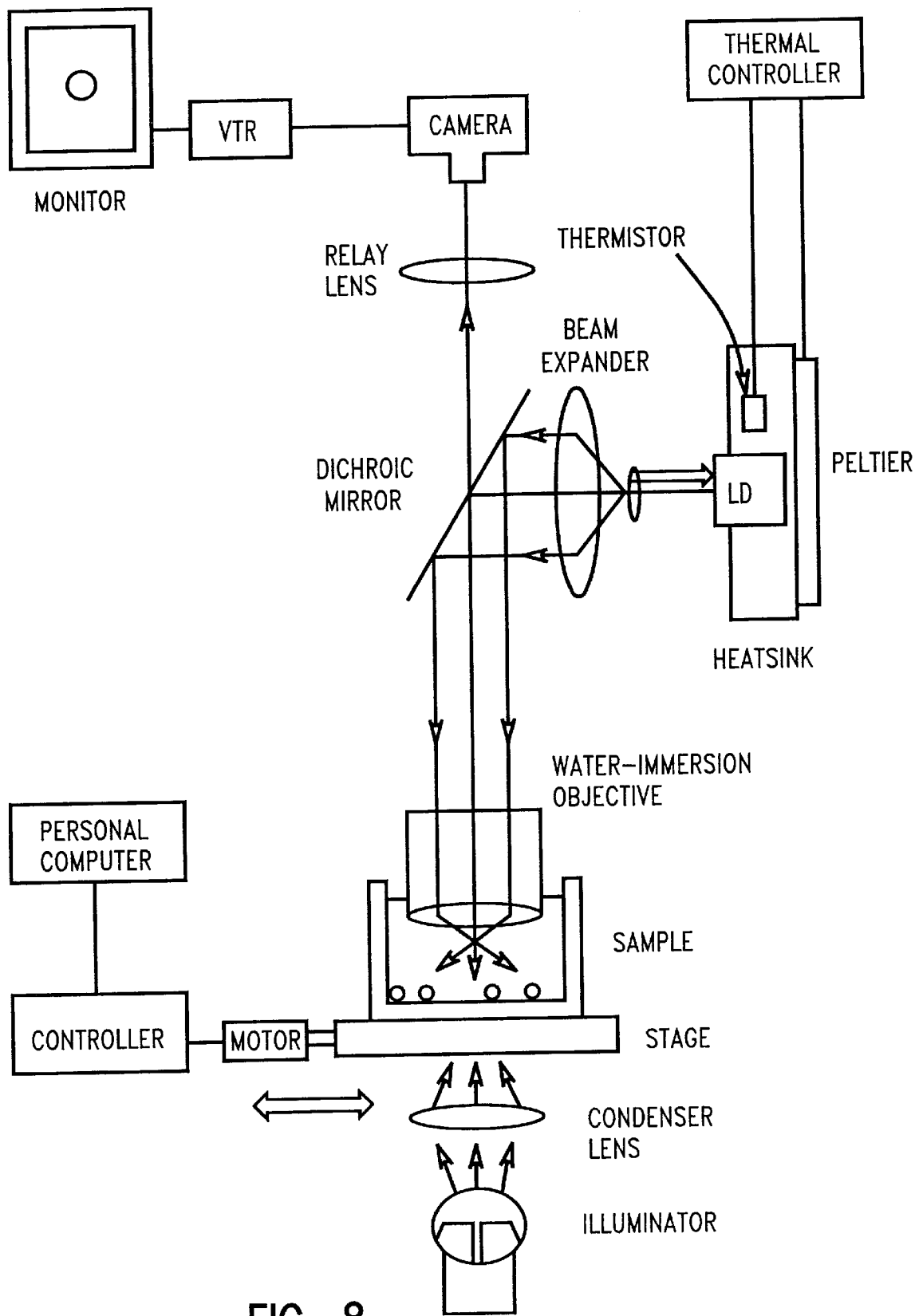
FIG. 8 shows an embodiment using optical trapping.

Optical trapping may be used to transiently immobilize a sample particle for determination of the presence or absence of phosphor on the particle. Conveniently, the wavelength range used to trap sample particles may be essentially identical to an excitation wavelength range for the up-converting phosphor(s) selected, so that optical trapping and excitation illumination is performed with the same source. FIG. 8 shows a block diagram of an apparatus used for single-beam gradient force trapping of small particles.

Figure 26:
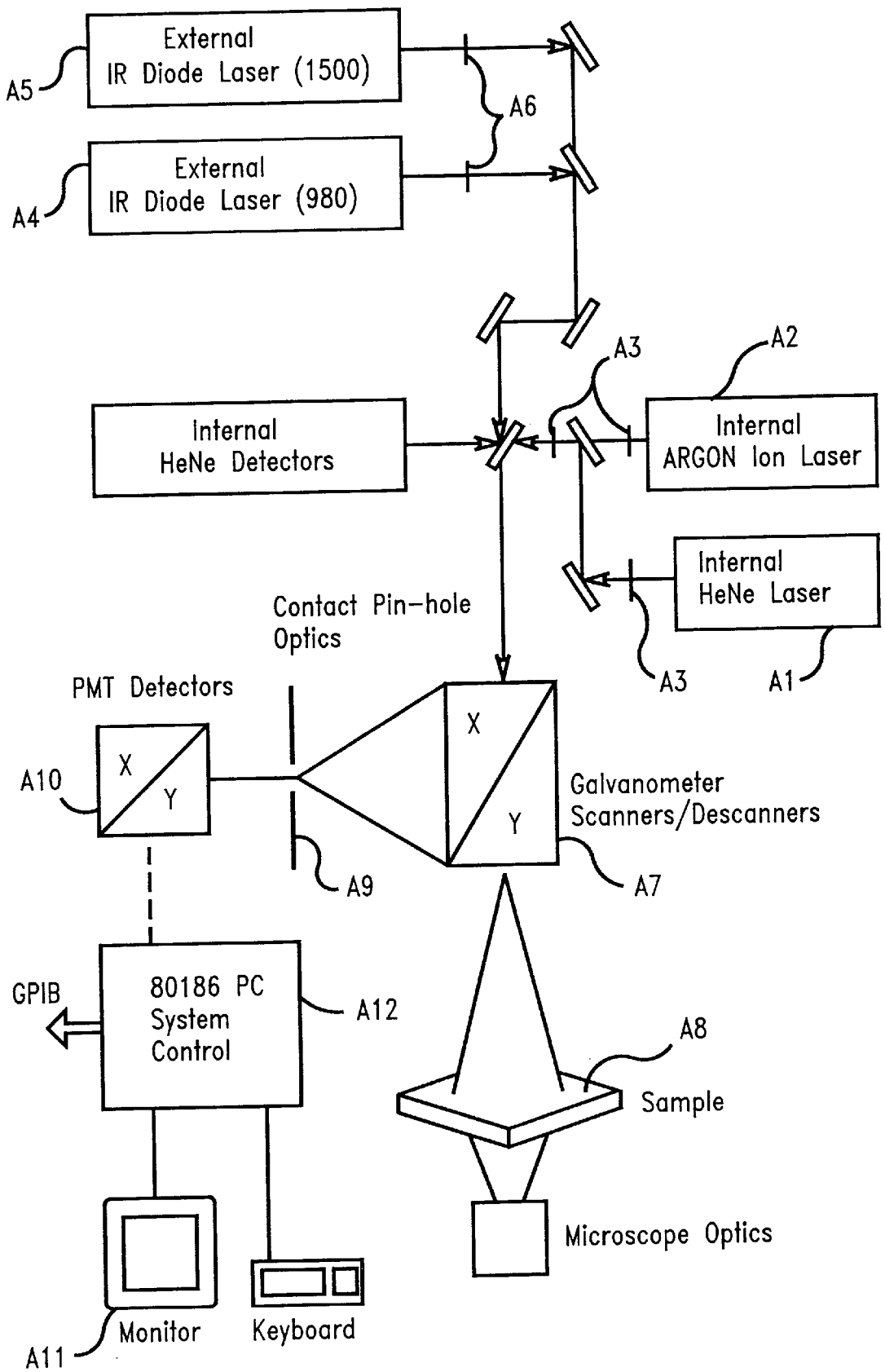
FIG. 26 shows a block diagram of one embodiment of apparatus for carrying out the present invention on a sample using a microscope.

FIG. 26 is a block diagram of one embodiment of apparatus for carrying out the present invention on a sample using a microscope. In this embodiment a standard microscope is modified to accept infrared scanning optics and image processing electronics. A suitable microscope for modification is the Zeiss model CLSM-10.

The microscope is fitted with a HeNe laser A1 for visible imaging and an argon laser A2 for both visible and UV imaging. Both lasers are mounted internally and are individually selectable through a series of motorized shutters A3. The upconverting phosphors are excited with an externally mounted IR laser diode. In the preferred embodiment, two IR laser diodes A4 and A5, operating at two different IR wavelengths, are coupled to the microscope thereby allowing multiple phosphor reporters to be identified. Laser diodes A4 and A5 are individually selectable using motorized shutters A6. When an IR beam is selected, it is routed through the microscope's qalvanometrically controlled scanning mirrors A7 which scan the beam in a raster fashion. The beam passes through the objective lens (not shown) onto a sample A8 and is reflected back through the objective lens to a set of galvanometrically controlled receiving mirrors A7. Receiving mirrors A7 reflect the light onto pinhole optics A9. If the confocal mode is selected, pinhole A9 limits the detected image to the light collected from the focal plane. The light is imaged on a photomultiplier tube (PMT) A10. The thickness of the focal plane is proportional to the size of the pinhole. The scanning speed is chosen such that sufficient signal intensity is received at the PMT A10. In the preferred embodiment of this apparatus, a 20 micrometer diameter pinhole is used which results in a depth of field of about 1 micrometer. If the confocal mode is not selected, the beam is deflected around pinhole optics A9 directly to PMT A10.

Once the optical signal is converted into an electronic one, a standard, composite video signal can be developed and displayed as an image on a television monitor A11. The image can be manipulated and enhanced through standard image processing software. In the preferred embodiment of this apparatus the software runs on an IBM 486 PC A12. The software can be used to perform averaging, filtering, edge detection and overlaying the images received from each of the different light sources.

In the confocal mode, it is possible to reconstruct a 3 dimensional view of sample A3. The reconstruction is formed by stepping through sample A8 at small intervals, making an image of the sample at each interval. The multiple sequential images are transferred to an external graphics machine (not shown) for reconstruction of the sample in 3 dimensions. These 3-D images can then be rotated to give different perspectives of the data sets, leading to a better understanding of the samples.

Figure 27:
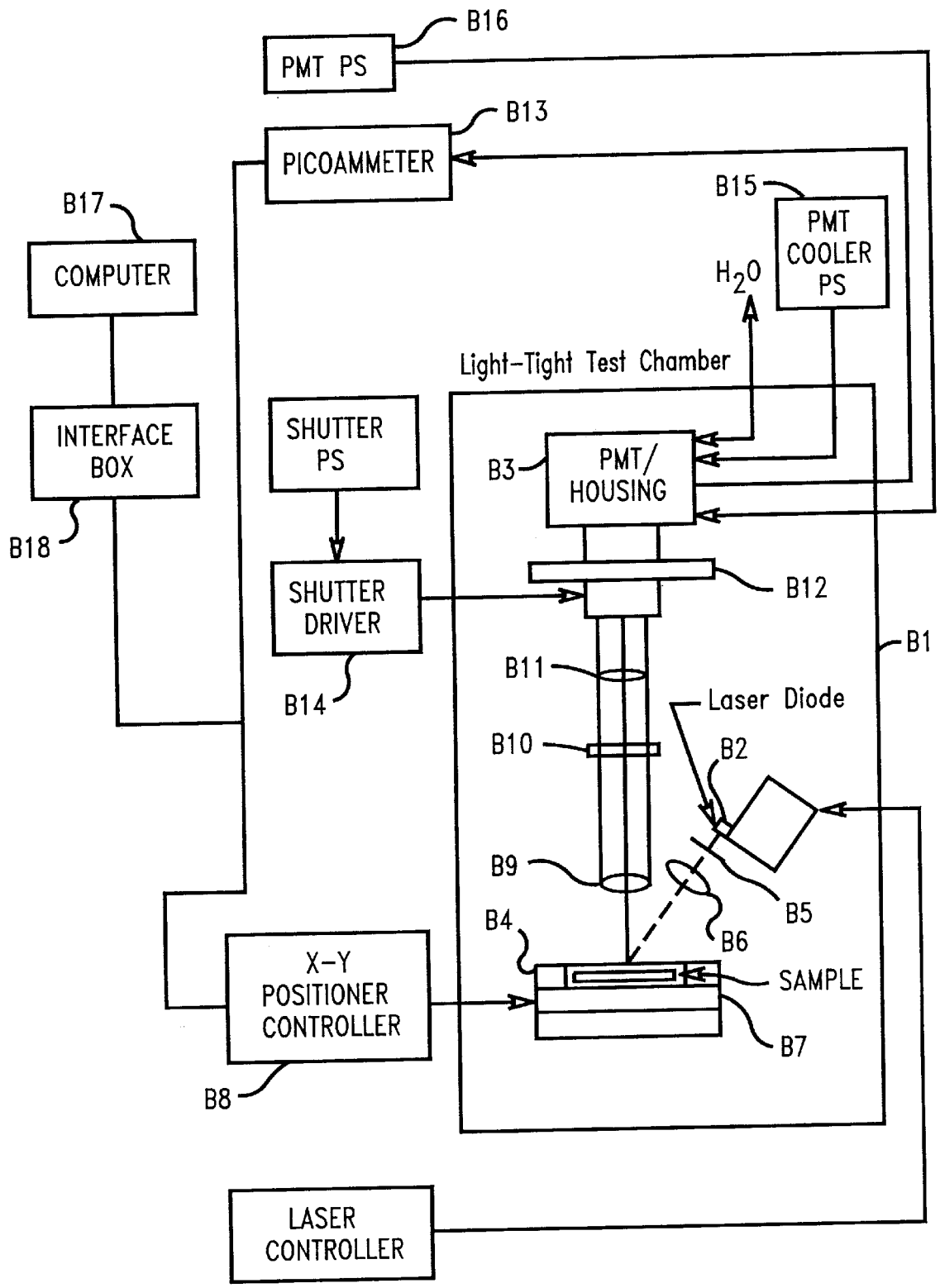
FIG. 27 is a block diagram of a microtiter plate reader for use with the present invention.

FIG. 27 is a block diagram of a microtiter plate reader for use with the present invention. Within a light-tight test chamber B1 is a near IR laser excitation source B2, a photomultiplier tube (PMT) detector B3, and a sample assay plate B4. In the preferred embodiment of this apparatus, assay plate B4 is a Terasaki HLA plate. This plate is preferred due to its small tapered sample wells which tend to concentrate the sample material into a relatively small target area. The target area in this configuration is still larger than the diameter of the laser beam. Furthermore, it is possible that the distribution of the assay material across the bottom of the well is not even. Because of these two factors, simply aiming the laser at the center of the bottom well surface is unlikely to provide accurate readings. There are several approaches that can be used to circumvent this problem. The first approach is to defocus the laser beam sufficiently to allow a larger amount of the target area to be interrogated. However, depending upon the output of laser B2, defocussing the beam may lower the sensitivity of the apparatus to an unacceptable level. Another approach is to raster scan the laser beam across the bottom of target well. A third and preferred approach is to simply automate the scanning and data collection system.

Light from laser B2 passes through a filter B5 and is focussed by a lens B6 onto an individual sample well of assay plate B4. Plate B4 is mounted on a pair of translators B7 which allow positioning in the horizontal and vertical directions. In the present configuration translators B7 allow approximately 2.5 centimeters of travel; sufficient to address 3 sample wells in each direction. Translators B7 are controlled by an x-y controller B8. Controller B8 allows for either manual or computerized control.

A sample well on plate B4, when containing upconverting phosphors, will emit visible light which is collected by a lens B9, passed through a filter B10, and focussed through a lens B11 and a shutter B12 onto PMT B3. PMT B3 outputs a current which is measured by a picoammeter B13. The PMT signal is proportional to the phosphor emission intensity. Shutter B12, controlled by a shutter driver B14, provides exposure protection to PMT B3, thereby preventing damage which may result from exposure to very intense light sources. Furthermore, overexposure of PMT B3 to light causes high dark currents which require several hours to decrease. PMT B3 is cooled for lower dark current and noise. Associated with the PMT cooler is a water-cooled power supply B15. A power supply B16 supplies high voltage to PMT B3.

Figure 28:
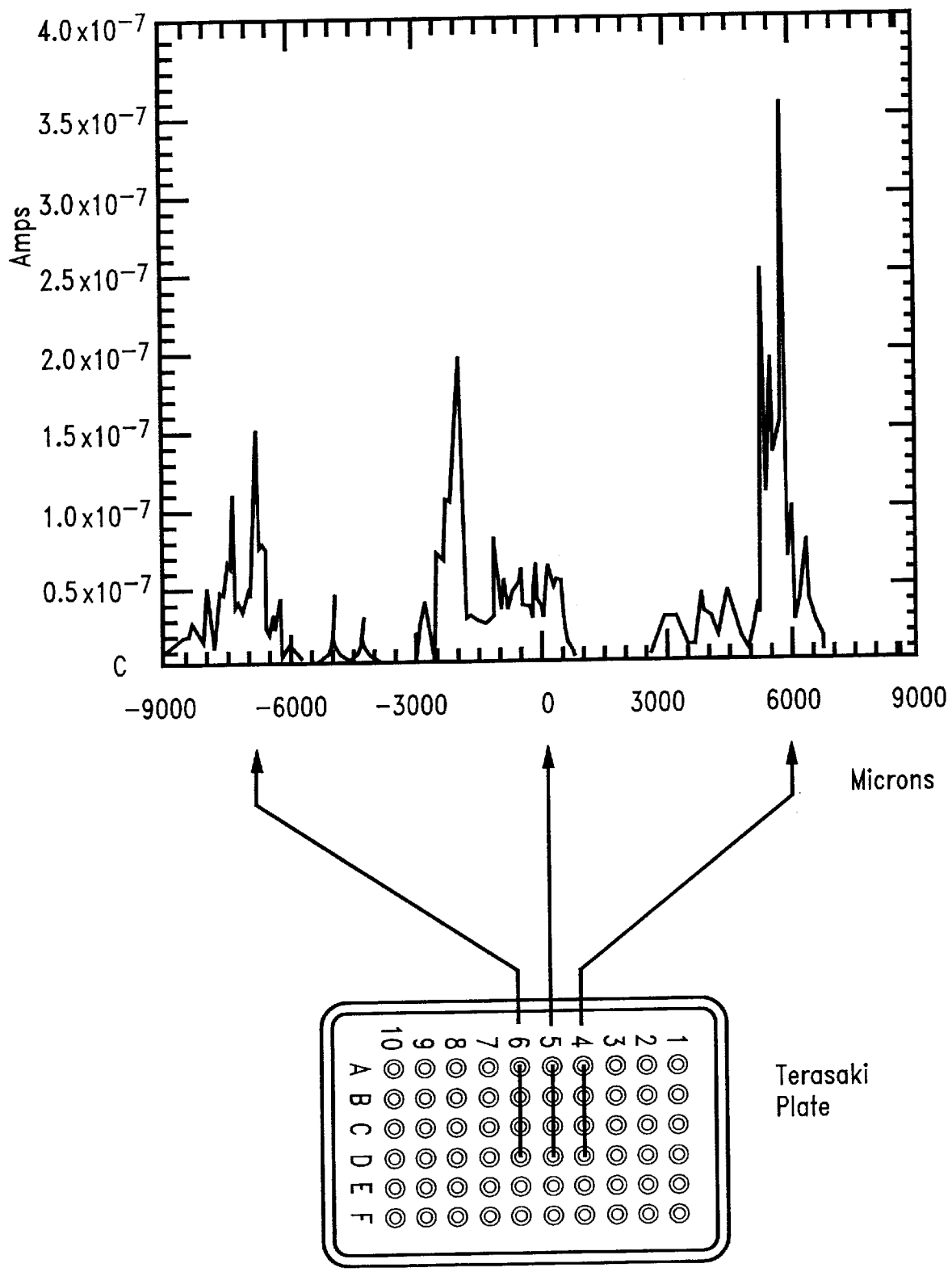
FIG. 28 is an illustration of the data for upconverting phosphors in three test wells.

When the apparatus is operated in a computerized mode, a computer B17 regulates controller B8 through an interface box B18. Picoammeter B13 can also be connected to computer B17, thereby allowing automated data acquisition to be performed. The data acquisition procedure moves translator B7 in the x direction to a first position at which location a specified number of current readings are taken and the average is calculated. Translator B7 then moves sample B4 a predetermined distance in the x direction to a new location where new data is collected. During this process, the data is plotted in order to provide the user with an immediate visual evaluation. After the scan is completed, the data can be saved or further data processing can be performed. FIG. 28 is an illustration of the data for upconverting phosphors in three test wells.

Figure 29:
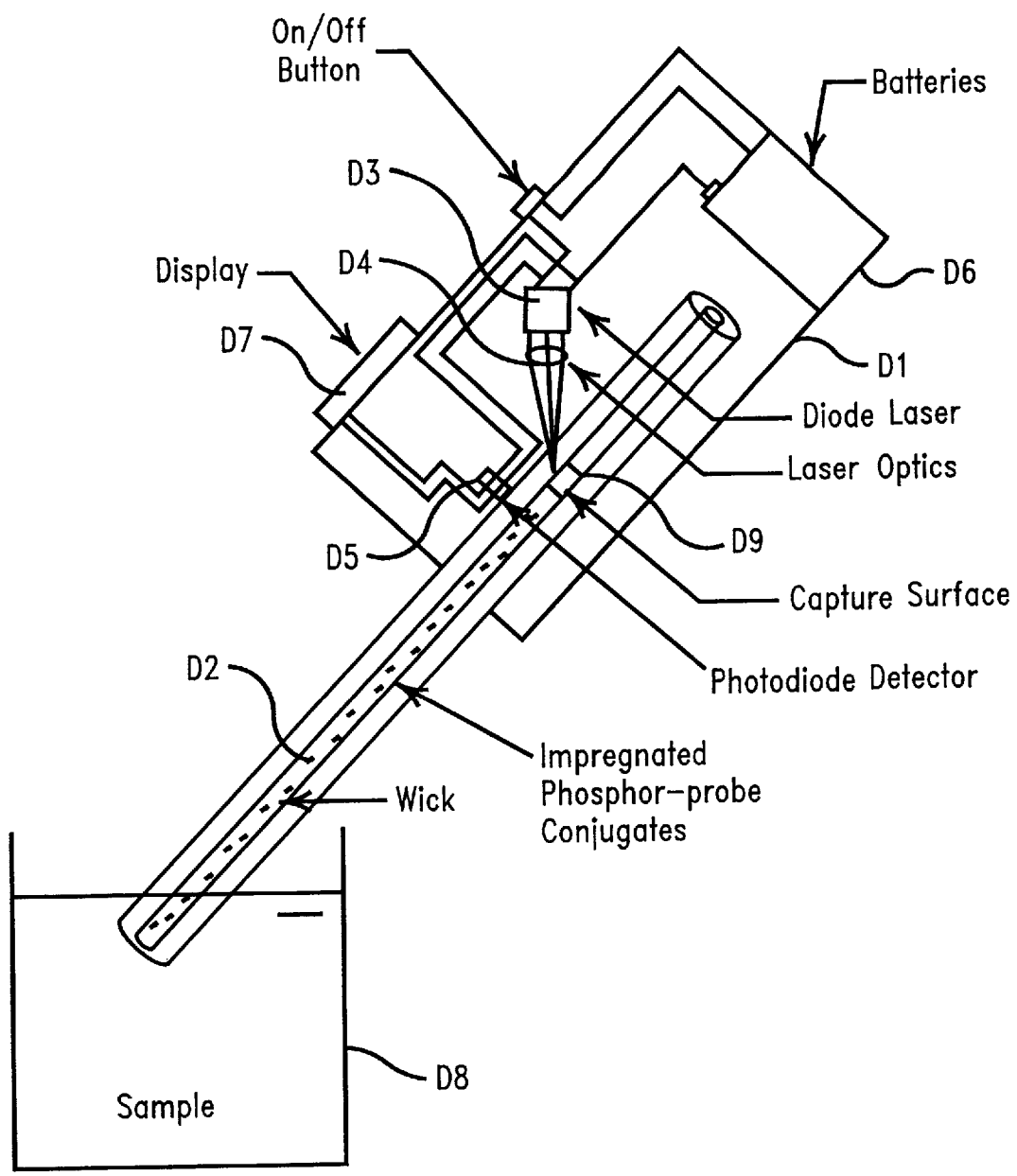
FIG. 29 is a schematic view of a second embodiment of a hand-held probe for carrying out the present invention.

FIG. 29 is a schematic view of a second embodiment of a hand-held probe for carrying out the present invention. This embodiment is comprised of a housing D1 and a capillary wick D2. Within housing D1 is a diode excitation laser D3, a lens assembly D4, a photodiode detector D5, and a battery supply D6. A display D7 mounted to one surface of housing D1 communicates the results of the test to the user. In the preferred embodiment, laser D3 operates in the 960–980 nanometer range.

In use, wick D2 wicks up a portion of a sample fluid D8 which is suspected of containing the target antigens. Target antigens bind to the antibodies present at a capture surface D9. Capture surface D9 is positioned at the focal point of source D3. The target antigens can be labeled with phosphor-antibody conjugates either before or after capture. In the preferred embodiment wick D2 is formed of glass. In this configuration capture surface D9 is prepared simply by filling the inside of the capillary with a bubble containing the antibodies of interest. By silanizing the inner surface with organofunctional silanes, conventional chemistries can be used to covalently link the antibodies or other biological macromolecule(s) to the inner tube wall at the site of the liquid bubble. The surface energy of the capillary is also easy to modify by silanization, which will help prevent nonspecific reagent and antigen adherence to the walls of the tube.

In the preferred embodiment of this apparatus, the lower portion of wick D2 is impregnated with upconverting phosphors that are conjugated to the target analytes or a cross-reactive epitope for the capture probe. In use, the phosphor conjugates chromatograph towards capture surface D9 as sample fluid D8 is drawn up wick D2. As phosphors accumulate at capture surface D9, they will begin to emit visible light upon excitation by diode laser D3. The visible light emitted by the phosphors is detected by detector D5. The output of detector D5 is displayed on display D7. The amount of upconverted light reaching the detector is directly proportional to the concentration of labeled target antigen captured at the capture surface.

Figure 30:
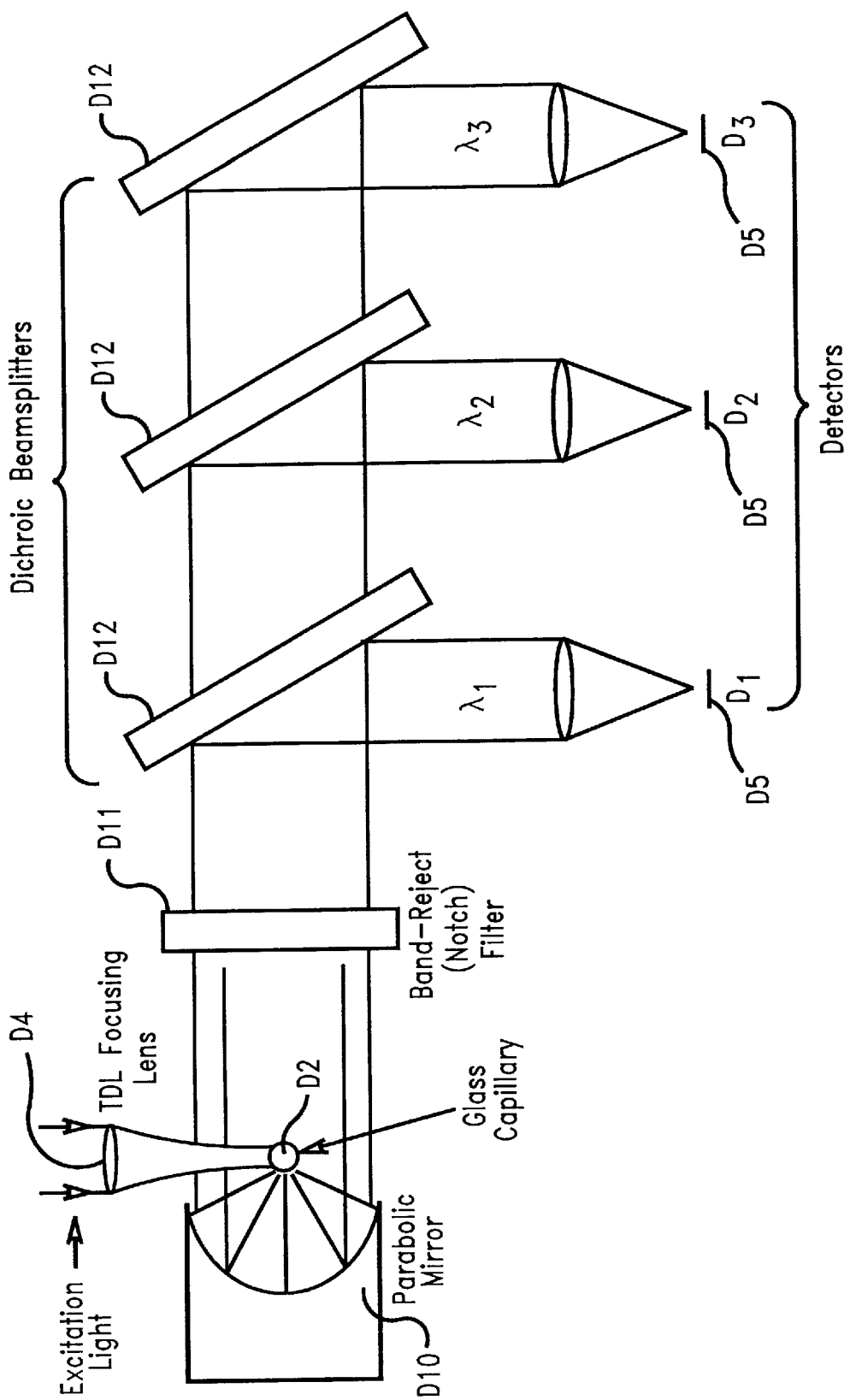
FIG. 30 illustrates a three channel configuration using interference filters.

The apparatus of FIG. 29 can be designed to simultaneously detect more than one target antigen. FIG. 30 illustrates a three channel configuration using interference filters. In this configuration capillary wick D2 is placed at the focus of a small parabolic reflector D10 capable of collecting approximately half of the emitted phosphorescence. The beam from diode laser D3 is directed onto capillary wick D2 at capture surface D9 along a direction perpendicular to the optical axis of reflector D10. Phosphorescent light from capture surface D9 is collected and collimated by mirror D10, directed through a notch filter D11 to reject the pump light, and onto three detectors D5 using three dichroic beam splitters D12. The reflectance bands of dichroic beamsplitters D12 are matched to the emission bands of the three phosphors used in the detection process.

In an alternate embodiment of this apparatus, dichroic beamsplitters D12 could be replaced with three bandpass filters used in the transmission mode. By placing the three filters on a rotation wheel, a single detector D5 could be used. Another alternative is to use a diffraction grating and a linear detector array to obtain an actual emission spectrum.

Figure 31A:
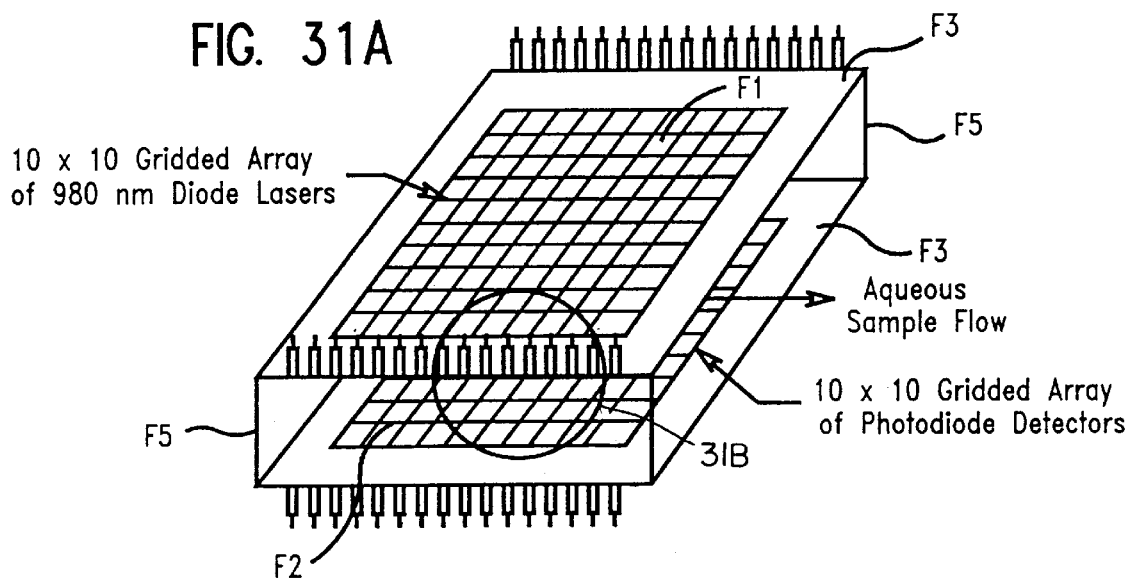
FIG. 31A is an illustration of an embodiment of the invention in which a diode laser array F1 and a detector array F2 are combined in a single device.
Figure 31B:
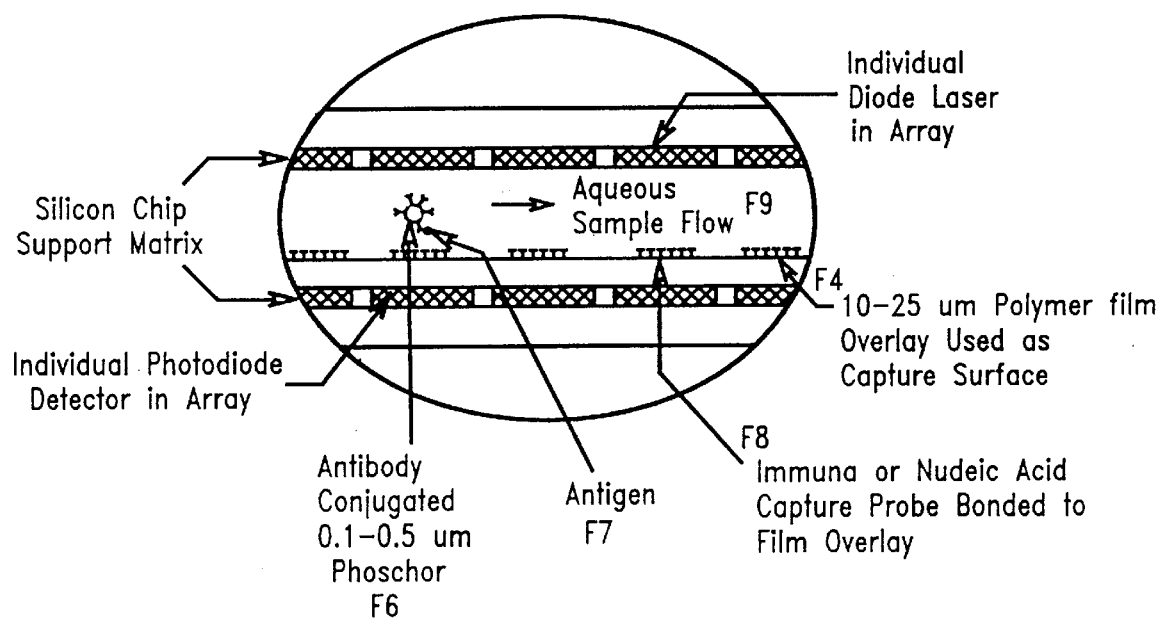
FIG. 31B is a detailed view of a small section of the device shown in FIG. 31A.

FIG. 31A is an illustration of an embodiment of the invention in which a diode laser array F1 and a detector array F2 are combined in a single device. In the preferred embodiment, arrays F1 and F2 are fabricated on a pair of silicon chips F3 with array dimensions of approximately 1 square centimeter. FIG. 31B is a detailed view of a small section of the device shown in FIG. 31A. overlaying detector array F2 is a polymer film F4 of approximately 10 to 25 micrometers thickness which is used as the capture surface. Arrays F1 and F2 are separated by a spacer F5. Array F1 is comprised of Fabrey-Perot diode lasers, Preferably tuned to 980 nanometers. Lasers of this type are easily fabricated in gridded array patterns using conventional photolithography techniques. Each individual laser in array F1 has a columnar beam designed to strike only the adjacent portion of capture surface F4. The required power density of the individual lasers is dependent upon the efficiencies of the phosphors being used as well as the required detection efficiency. The detectors comprising array F2 are chosen to have an extremely low sensitivity in the wavelength region in which laser array F1 operates. If additional discrimination between the excitation and emission Wavelengths is required, a cutoff filter can be used, Preferably incorporated directly into capture surface F3.

Upconverting phosphors F6 are conjugated by any of a variety of conventional biochemical crosslinking chemistries to antibody, nucleic acid probes, or other biological macromolecules (e.g., carbohydrates, lectins, streptavidin, MHC complexes), as well as to biological or chemical antigens (F7). Bonded to overlay F3 is a grid array F8 of complementary probes or antigens which are bound to capture surface F3 using the same crosslinking chemistries. In use, a sample fluid F9 flows between arrays F1 and F2, target probes or antigens are captured by grid array F8 and excited by laser array F1, and the emissions detected by detector array F2.

Typically, the upconverting phosphors to be used with this apparatus are approximately 0.1 to 0.5 micrometers. Since the size of the individual phosphor particles is of the order of the excitation wavelength, the power of the emission from the phosphors can be approximated by:

$$P_{em} = fND^{3.4}I_{ex}^2$$

where f is the phosphorescence efficiency (generally less than or equal to $10^{-17}$ cm$^4$W$^{-1}$ $\mu$m$^{-3.4}$ particle$^{-1}$), N is the number of phosphor particles in the light path, D is the diameter of the phosphor particles, and $I_{ex}$ is the power density of the excitation source.

Since the emitted power scales as the square of the excitation intensity, diagnostics using upconverting phosphors perform better in a microassay format. Assuming a constant power output from the excitation source, the excitation power density increases proportionally with the decrease in detection area, and the number of phosphor particles in the light path decreases linearly with a decrease in the detection area. Since the power of the light emitted from the phosphors scales with the square of the excitation power density, but linearly with the number of phosphors, $P_{em}$ will increase in inverse proportion to the detection area. Therefore, a 100×100 array will actually be 100 times more sensitive than a 10×10 array.

Fluorescence-Activated Cell Sorting

The up-converting phosphors described herein can be used as phosphorescent labels in fluorescent cell sorting by flow cytometry. Unlike conventional fluorescent dyes, up-converting phosphors possess the distinct advantage of not requiring excitation illumination in wavelength ranges (e.g., UV) that damage genetic material and cells. Typically, up-converting phosphor labels are attached to a binding reagent, such as an antibody, that binds with high affinity and specificity to a cell surface protein present on a subset of cells in a population of cells in suspension. The phosphor-labeled binding component is contacted with the cell suspension under binding conditions, so that cells having the cell surface protein bind to the labeled binding reagent, whereas cells lacking the cell surface protein do not substantially bind to the labeled binding reagent. The suspended cells are passed across a sample detector under conditions wherein only about one individual cell is present in a sample detection zone at a time. A source, typically an IR laser, illuminates each cell and a detector, typically a photomultiplier or photodiode, detects emitted radiation. The detector controls gating of the cell in the detection zone into one of a plurality of sample collection regions on the basis of the signal(s) detected. A general description of FACS apparatus and methods in provided in U.S. Pat. Nos. 4,172,227; 4,347,935; 4,661,913; 4,667,830; 5,093,234; 5,094,940; and 5,144,224, incorporated herein by reference. It is preferred that up-converting phosphors used as labels for FACS methods have excitation range(s) (and preferably also emission range(s)) which do not damage cells or genetic material; generally, radiation in the far red, and infrared ranges are preferred for excitation. It is believed that radiation in the range of 200 nm to 400 nm should be avoided, where possible, and the wavelength range 760 nm to 765 nm may be avoided in applications where maintenance of viable cells is desired.

Additional Variations

There are several apparatus design issues relating to the unique excitation and emission characteristics of upconverting phosphors which must be considered when using up-converting phosphors with flow cytometry. The first issue is the time required to reach maximum emission intensity. Since upconversion is a two photon process, upconverting phosphor emission is time delayed approximately 100 microseconds. The phosphor must remain within the excitation beam for this period of time regardless of the flow rate. Therefore given a flow rate between 1 and 10 meters per second with a channel width of 70 to 200 micrometers, the length of the excitation beam must be between 100 and 1000 micrometers. Given that the phosphor emissions saturate at an excitation intensity of about 200 watts per square centimeter, the laser source typically must have a power between 0.01 and 400 milliwatts to achieve phosphor saturation. This implies that multiple laser diodes may be required to obtain maximum phosphorescence at the fastest flow rates.

Another design issue is that associated with the detector. Since there is a considerable separation between the excitation and emission wavelengths of the up-converting phosphors, detection can be performed using a photomultiplier tube (PMT), a photodiode, or a CCD array. The phosphorescence decay time is long, with a decay half life of approximately 300 microseconds. The most sensitive method of detection is to integrate the signal measured by the PMT. However, 99 percent detection of the available phosphorescent signal requires that the phosphor remain in the sight path of the detector for 5 times the phosphorescence decay half-life (i.e., 1.5 milliseconds). Assuming a flow rate of 10 meters per second and a channel width of 200 micrometers, the PMT must be able to detect over a path length of 1.5 centimeters. This path length is also the required spacing between cells flowing through the cytometer, implying a maximum count rate of 667 cells per second. It is, however, possible to sacrifice some detection sensitivity by reducing the detection path length, at least to that required to attain steady-state emission from the phosphors. As long as a steady-state emission peak is reached by the phosphor in the excitation window, the peak signal received by the PMT should be directly proportional to the concentration of phosphors present. The nonphotobleaching property of the phosphors makes this form of detection possible. The loss in detection sensitivity corresponding to a 0.1 centimeter path length (versus a 1.5 centimeter path length) is approximately a factor of 3. Triggering the emission detector can be accomplished by observing the light scattered by the cell as it passes through the excitation source.

Figure 9:
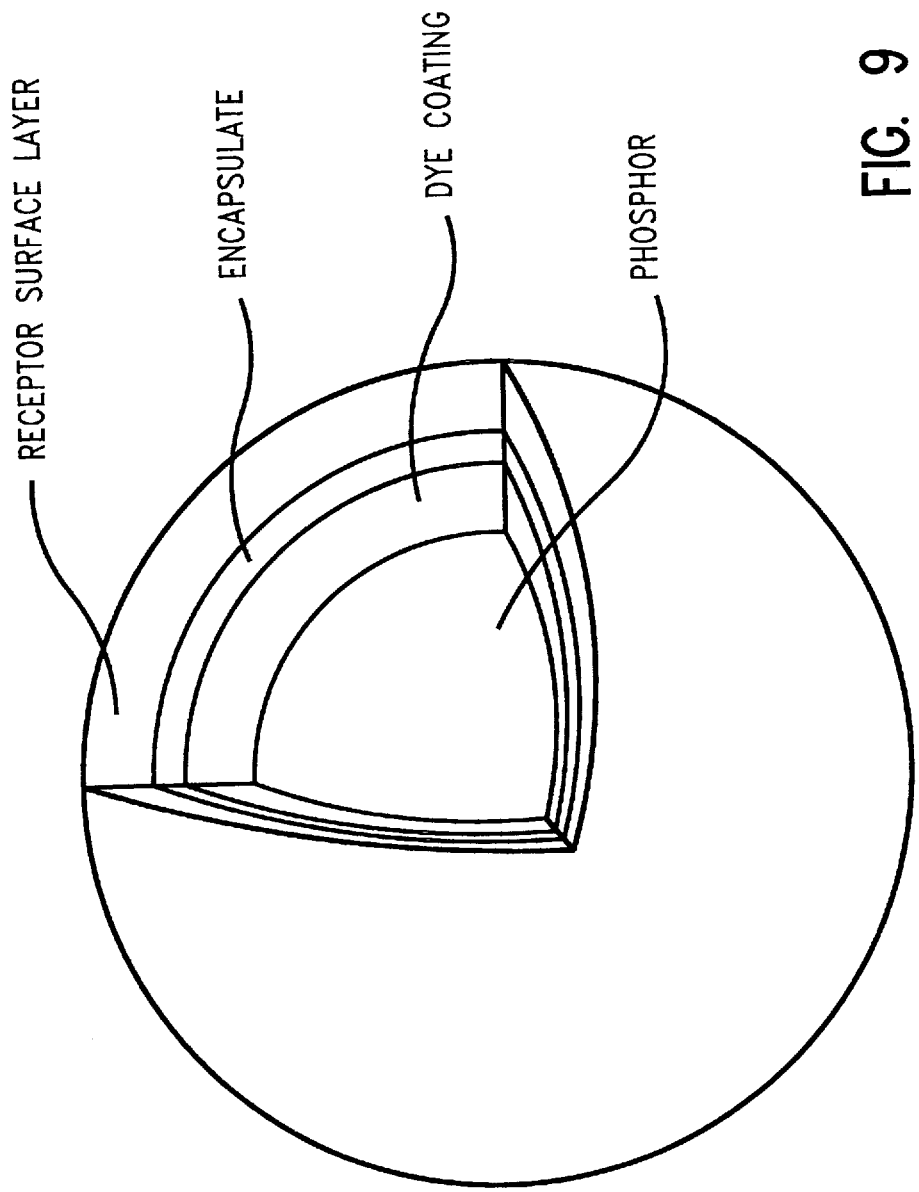
FIG. 9 shows schematically dye coating and encapsulation of an up-converting phosphor particle.

In environments where absorption of the up-converted phosphor radiation is high, the phosphor microparticles are coated with a fluorescent dye or combination of dyes, in selected proportions, which absorb at the up-converted frequency and subsequently re-radiate at other wavelengths. Because the single-photon absorption cross-sections for these fluors are typically very high, only a thin layer is required for complete absorption of the phosphor emission. This coat particle may then be encapsulated and coated in a suitable antigen or antibody receptor (e.g. microparticle). An example of this layering is depicted schematically in FIG. 9. There exists a wide variety of fluorescent dyes with strong absorption transitions in the visible, and their emission covers the visible range and extends into the infrared. Most have fluorescent efficiencies of 10% or more. In this manner, the emission wavelengths may be custom-tailored to pass through the particle's environment, and optical interference filters may again used to distinguish between excitation and emission wavelengths. If a relatively large wavelength "window" in the test medium exists, then the variety of emission wavelengths which may be coated on a single type of phosphor is limited only by the number of available dyes and dye combinations. Discrimination between various reporters is then readily carried out using the spectroscopic and multiplexing techniques described herein. Thus, the number of probe/reporter "fingerprints" which may be devised and used in a heterogenous mixture of multiple targets is virtually unlimited.

The principles described above may also be adapted to driving species-specific photocatalytic and photochemical reactions. In addition to spectroscopic selection, the long emission decay times of the phosphors permit relatively slow reactions or series of reactions to take place within the emission following photoexposure. This is especially useful when the phosphor-[catalyst or reactant] conjugate enters an environment through which the excitation wavelength cannot penetrate. This slow release also increases the probability that more targets will interact with the particle.

Figure 10A:
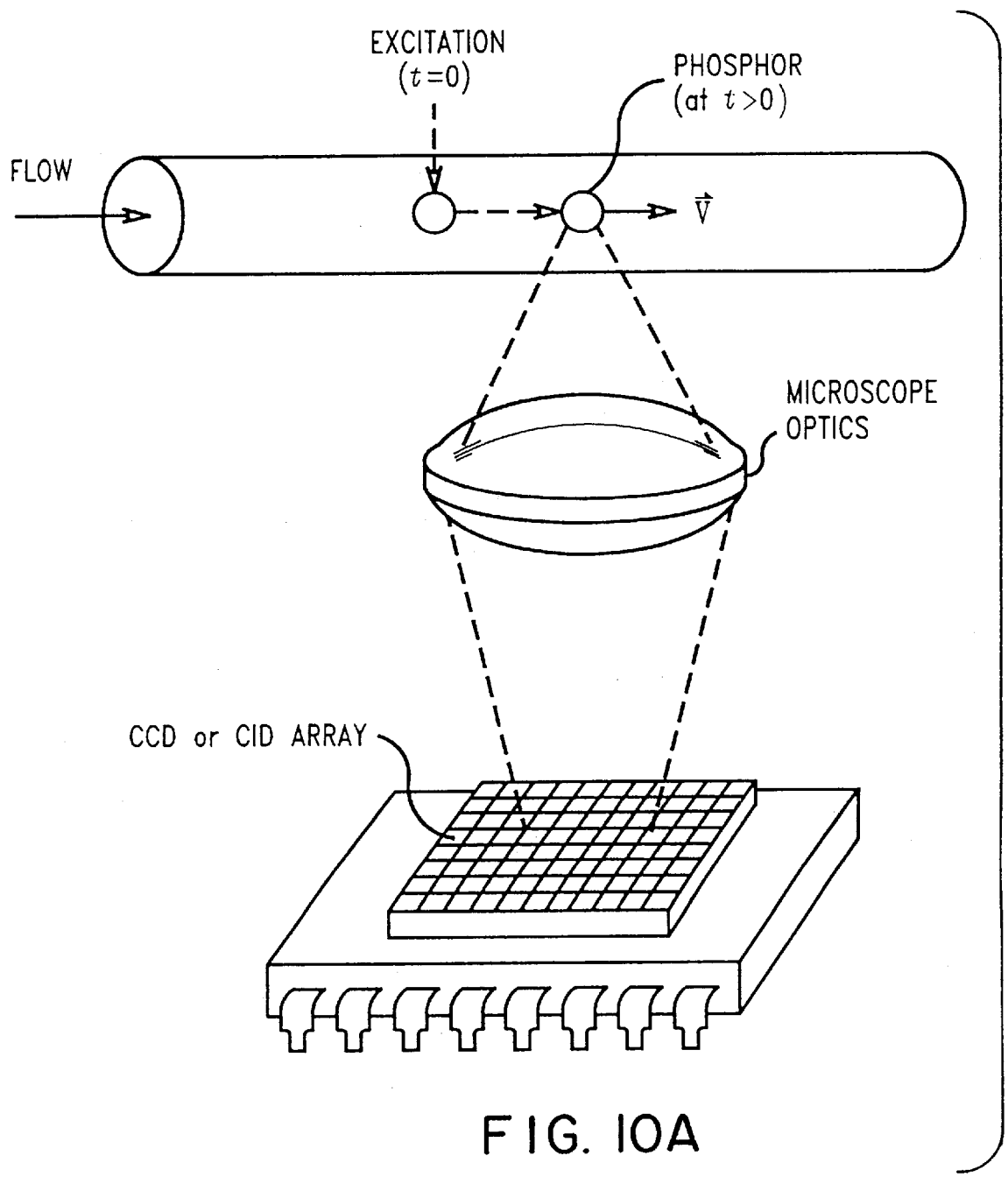
FIG. 10 shows schematically an apparatus for determining particle velocity and hydrodynamic or aerodynamic properties of a target.
Figure 10B:
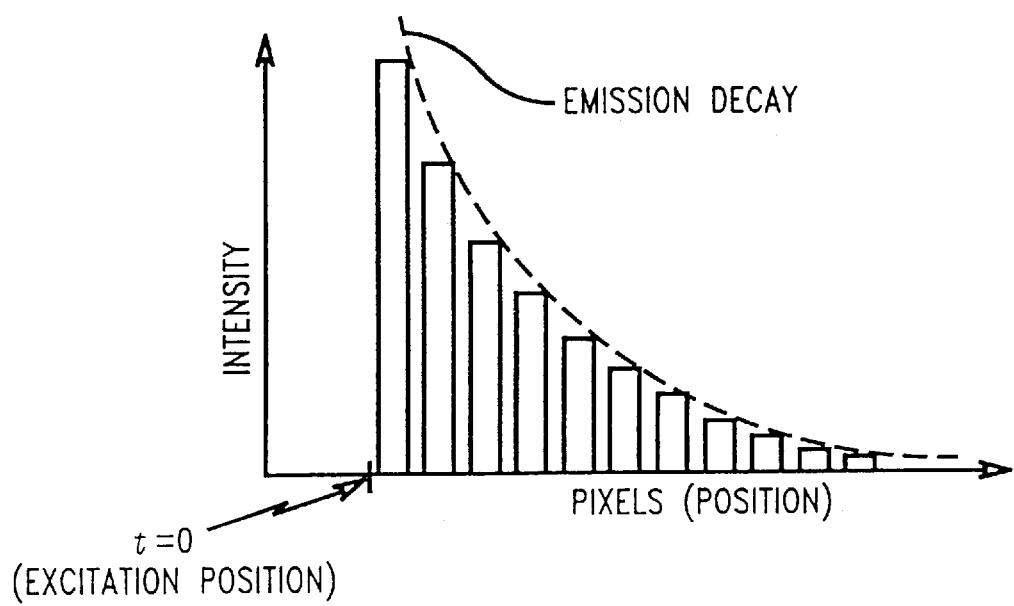

The unique decay rates of phosphor particles allow dynamic studies as well. In a system where continuous exposure to the excitation source is not possible, or is invasive and thereby undesirable, pulsed excitation followed by delayed fluorescence detection is necessary. After the phosphor reporter has been photoexcited, the subsequent emission from the phosphor or phosphor/dye conjugate particle lasts typically about a millisecond. In a dynamic environment, such as a static or flowing system with moving targets, the particle will emit a characteristically decaying intensity of light as it travels relative to the excitation/detection apparatus. Combined with imaging optics appropriate to the scale of the system and the velocities within the system, a CCD photoelectric sensor array will be used to detect the particle or particles movement across the array's field of view. The delayed emission of the phosphors, which is a well-characterized function of time, makes possible the dynamic tracking of individual particle's positions, directions and velocities, and optionally calculation of particle size, density, and hydrodynamic conformation. As a particle moves, it exposes more elements of the array, but with every-decreasing intensity. The more elements it exposes over a certain fraction of its decay time, the faster it is moving. Therefore, the integrated intensity pattern of a particle's emission "track" collected by the array is directly related to the velocity of the particle. The particles may be refreshed again at any time by the pulsed or chopped CW excitation source. FIG. 10 illustrates this scheme. Although only a depiction of "side-on" excitation and detection is shown, both side-on and end-on detection and excitation arrangements, or combinations, are possible. Reduction of the CCD array intensity information by computer analysis will allow near-real time tracking of the particles in a dynamically evolving or living systems. Data analysis and reduction performed by the computer would include a convolution of the intrinsic decay of the phosphor emission, the number of pixels illuminated and their signal level, the orientation of the decaying signal on the array, and the intensity contributions from a blur circle from particles moving in and out of the focal plane of the array. In an endon flow detection arrangement, the size of the blur circle would relate directly to how quickly the particle moves out of focus, thereby allowing the velocity of the particle to be determined. One possible application would be monitoring the chemistry and kinetics in a reaction column, alternatively, the application of this method to flow cytometry may permit the resolution of cells on the basis of hydrodynamic properties (size, shape, density). The method may also be useful for in vivo diagnostic applications (e.g., blood perfusion rate).

Up-converting phosphor labels may also be used to sense the temperature in the region at which the up-converting phosphor label is bound. Up-converting phosphor temperature measurement methods are described in Berthou H and Jorgensen C. K. (October, 1990) *Optics Lett.* 15(19): 1100, incorporated herein by reference.

Although the present invention has been described in some detail by way of illustration for purposes of clarity of understanding, it will be apparent that certain changes and modifications may be practiced within the scope of the claims.

The broad scope of this invention is best understood with reference to the following examples, which are not intended to limit the invention in any manner.

EXPERIMENTAL EXAMPLES

Validation of UP-Converting Inorganic Phosphors as Reporters

Up-converting phosphor particles comprising sodium yttrium fluoride doped with ytterbium-erbium were milled to submicron size, fractionated by particle size, and coated with polycarboxylic acid. $Na(Y_{0.80}Yb_{0.18}Er_{0.02})F_4$ was chosen for its high efficiency upon excitation in the range 940 to 960 nm. A Nd:Yag pumped dye laser/IR dye combination was used to generate 8-ns to 10-ns duration pulses in the above frequency range.

The laser pulses were used to illuminate a suspension of milled phosphor particles in liquid and attached to glass slides in situ. The suspension luminescence observed at right angles was monitored using a collection lens, a spatial filter in order to filter out scattered excitation light to the maximum possible extent, and a photomultiplier, vacuum photodiode, or simple solid state photodiode (depending on the light level observed).

Figure 11:
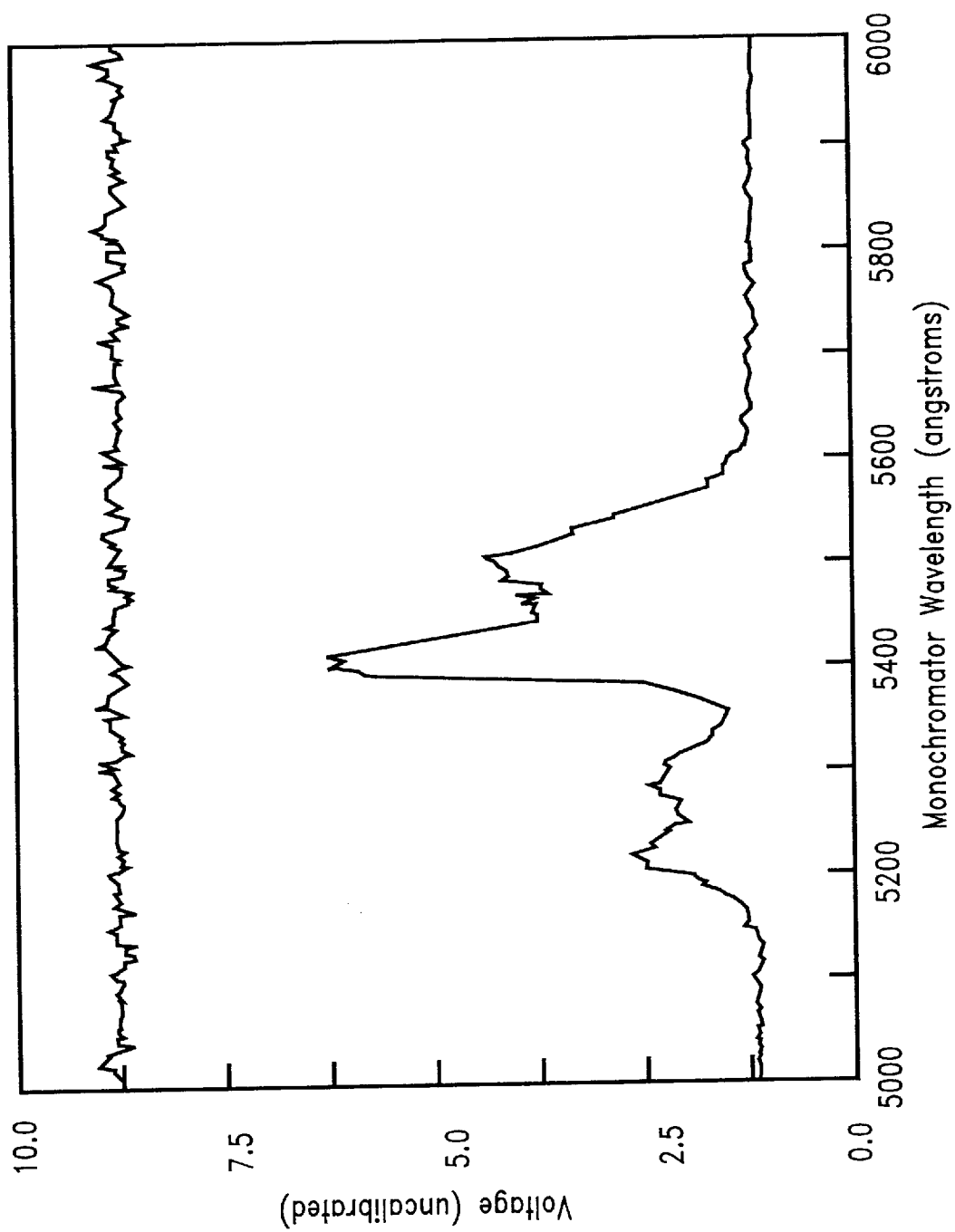
FIG. 11 is a phosphor emission spectrum of sodium yttrium fluoride-ytterbium/erbium up-converting phosphor with an excitation laser source at a wavelength maximum of 977.2 nm; emission maximum is about 541.0 nm.
Figure 12:
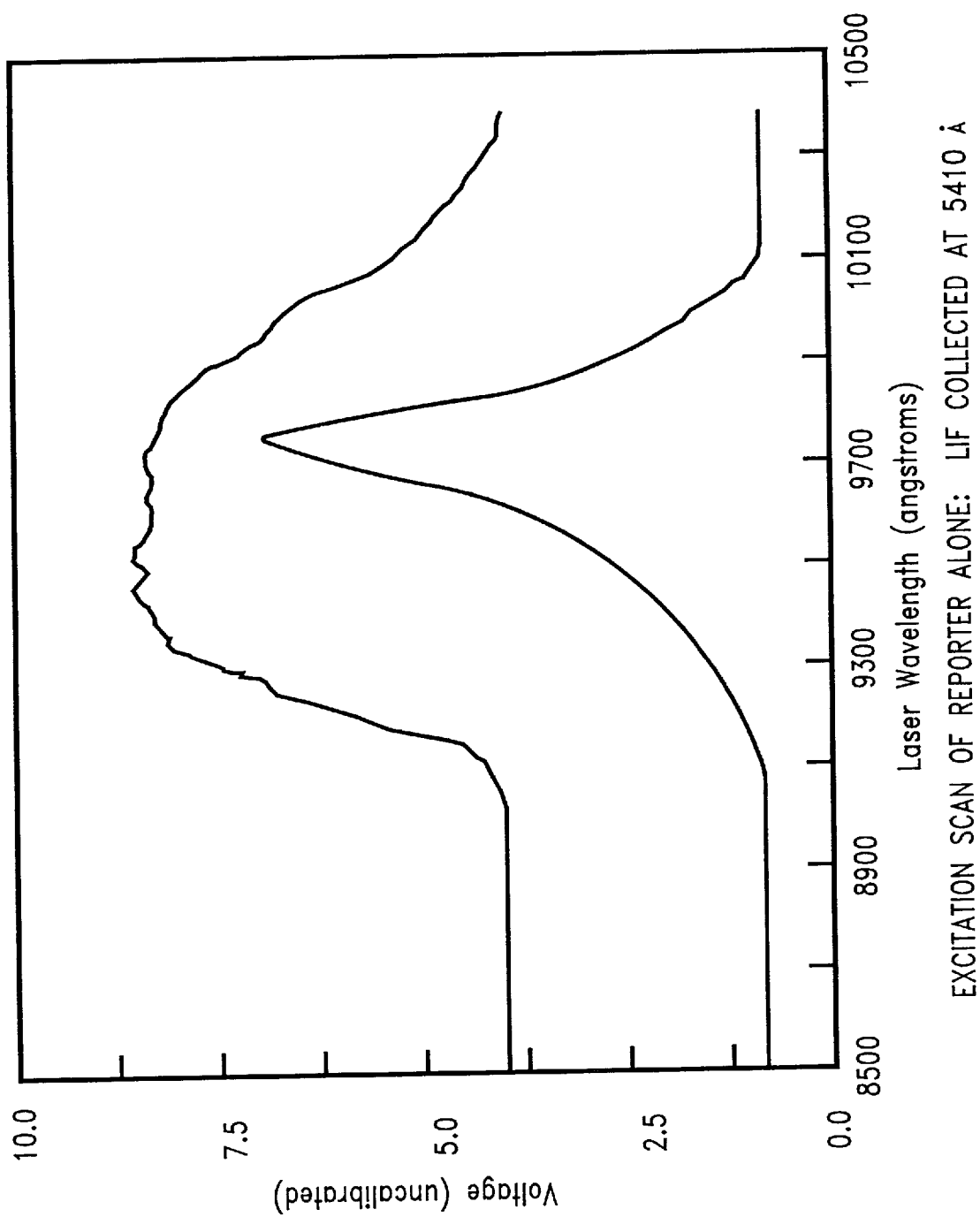
FIG. 12 is an excitation scan of the sodium yttrium fluoride-ytterbium/erbium phosphor excitation spectrum, with emission collection window set at 541.0 nm.
Figure 13:
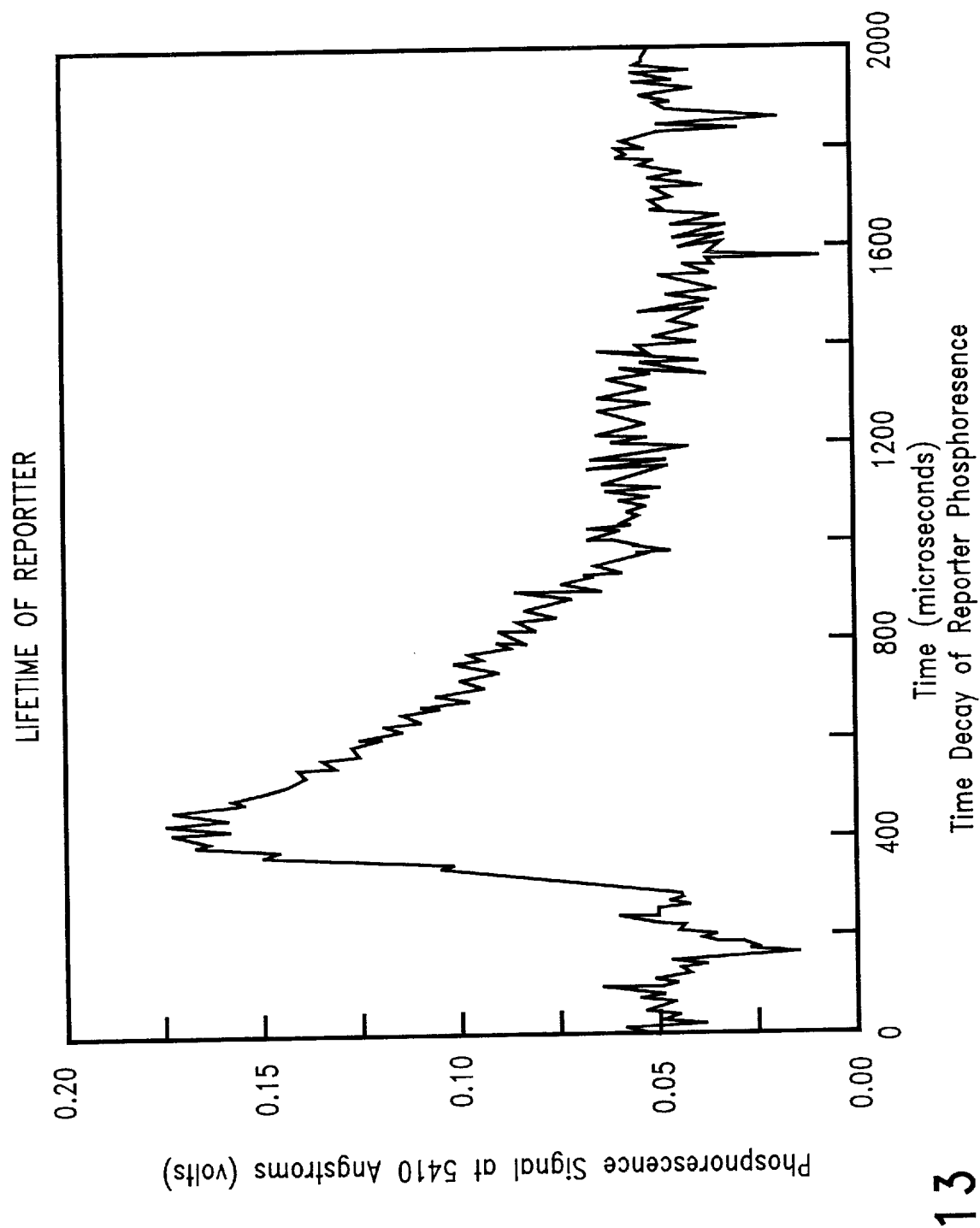
FIG. 13 is a time-decay measurement of the phosphor luminescence at 541 nm after termination of excitation illumination for sodium yttrium fluoride-ytterbium/erbium.
Figure 14:
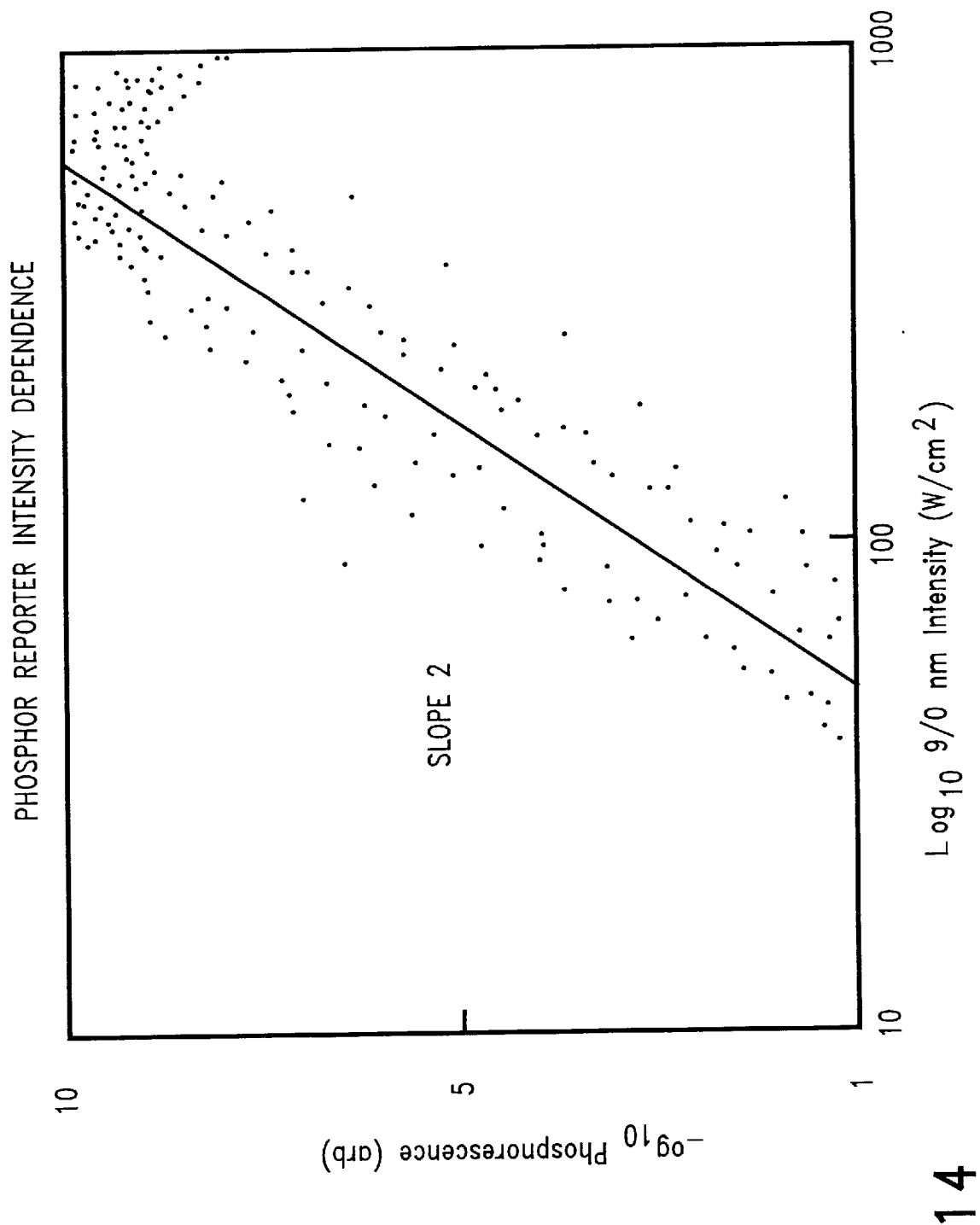
FIG. 14 shows the phosphor emission intensity as a function of excitation illumination intensity for a sodium yttrium fluoride-ytterbium/erbium phosphor.

The luminescent signal level was determined as a function of solution pH (range: 6–8), grain size, particle loading ($\mu g/cm^3$), and the nature of stabilizing anionic surfactant. Signals were recorded both as a time integral from a boxcar integrator and from a long RC time constant or as a transient signal using a transient digitizer in order to delineate the luminescence lifetime under particular experimental conditions. In situ signals were also measured by laser scanning microscopy. FIG. 11 is a fluorescence scan of the phosphor emission spectrum incident to excitation with a laser source at a wavelength maximum of 977.2 nm; emission maximum is about 541.0 nm. FIG. 12 is an excitation scan of the phosphor excitation spectrum, with emission collection window set at 541.0 nm; excitation maximum for the phosphor at the 541.0 nm, emission wavelength is approximately about 977 nm. FIG. 13 is a time-decay measurement of the phosphor luminescence at 541.0 nm after termination of excitation illumination; maximal phosphorescence appears at approximately 400 $\mu s$ with a gradual decay to a lower, stable level of phosphorescence at about 1000 $\mu s$. FIG. 14 shows the phosphor emission intensity as a function of excitation illumination intensity; phosphorescence intensity increases with excitation intensity up to almost about 1000 $W/cm^3$.

Figure 15:
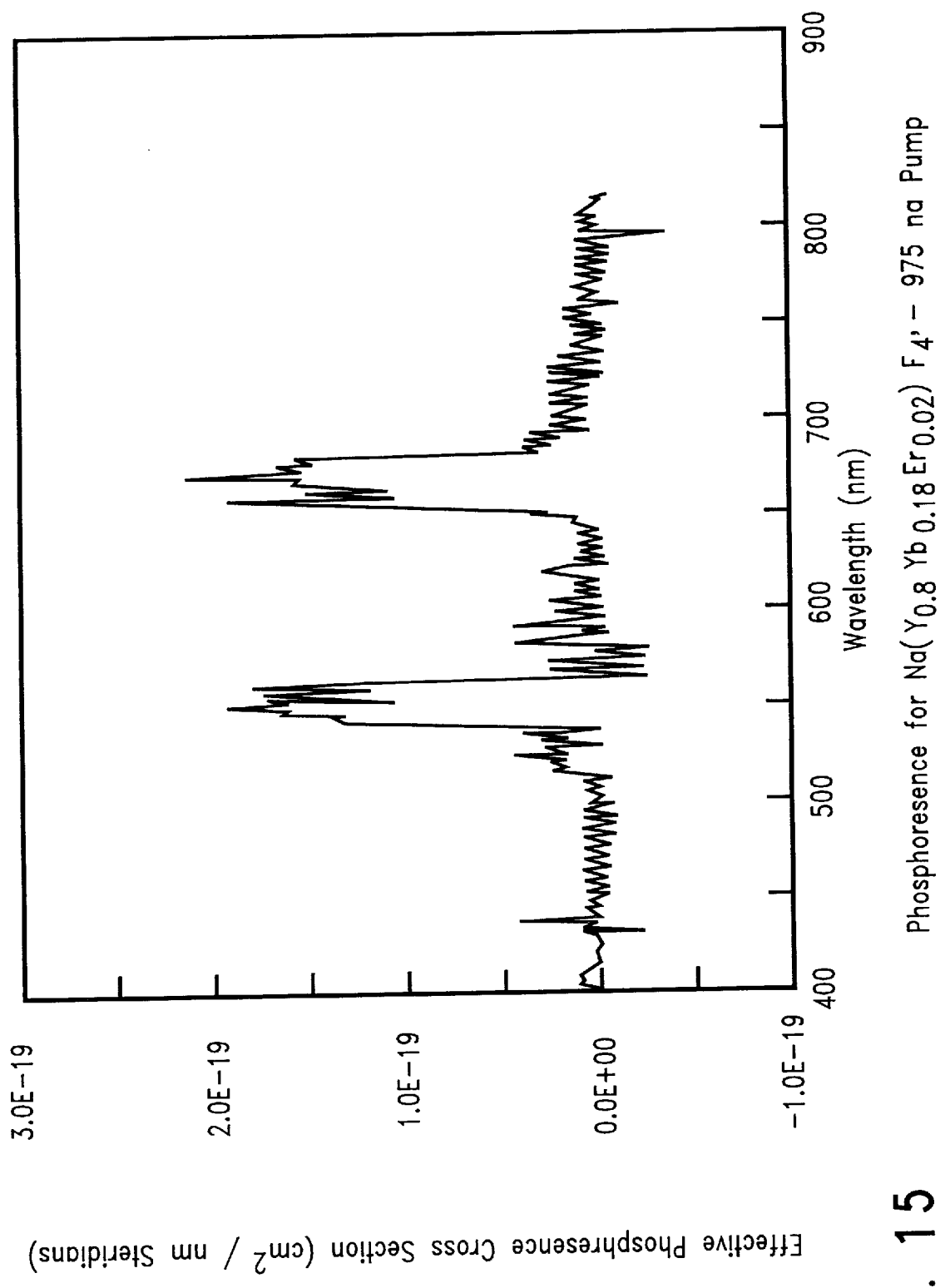
FIG. 15 shows effective single-photon phosphorescence cross-section for 0.3 μm particles of Na(Y$_{0.8}$Yb$_{0.12}$Er$_{0.08}$)F$_4$ following excitation with 200 W/cm$^2$ at 970 nm.
Figure 16:
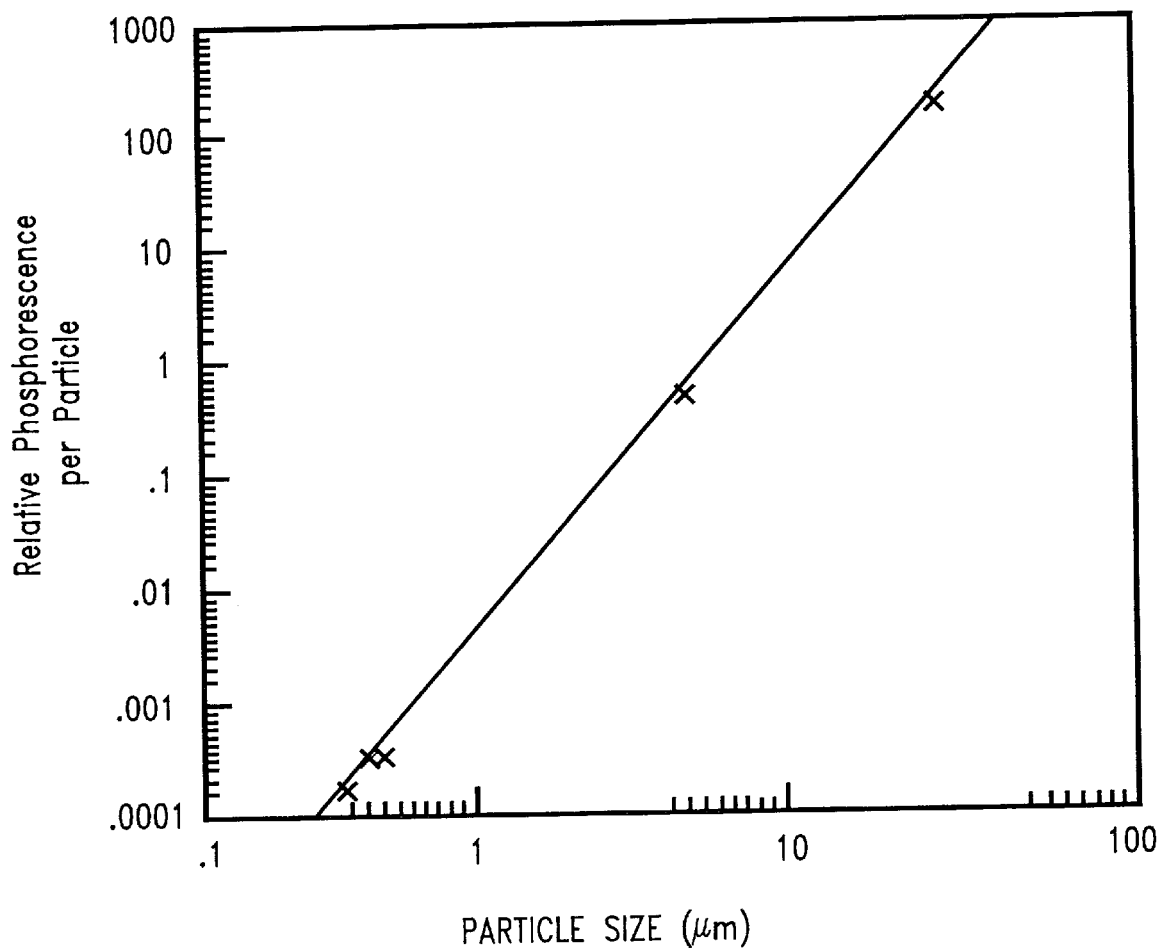
FIG. 16 shows size-dependence of phosphorescence cross-section for Na(Y$_{0.8}$Yb$_{0.12}$Er$_{0.08}$)F$_4$ particles.
Figure 17A:
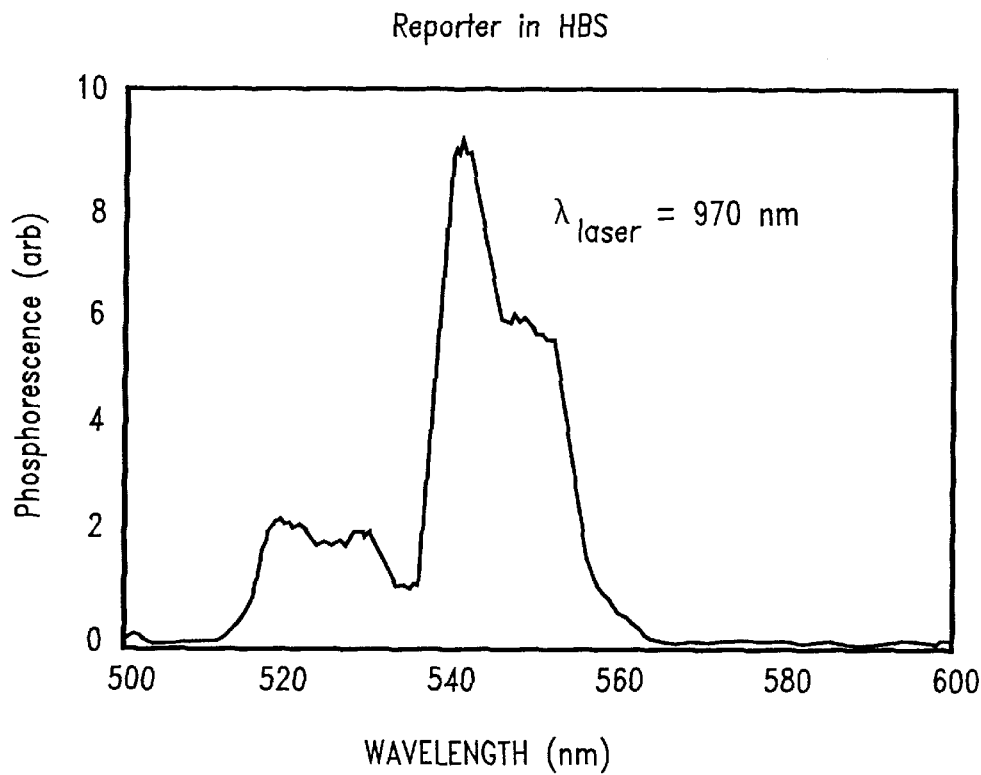
FIG. 17A shows a fluorescence scan of an up-converting phosphor reporter in Hepes-buffered saline induced by excitation with a 970-nm laser source.
Figure 17B:
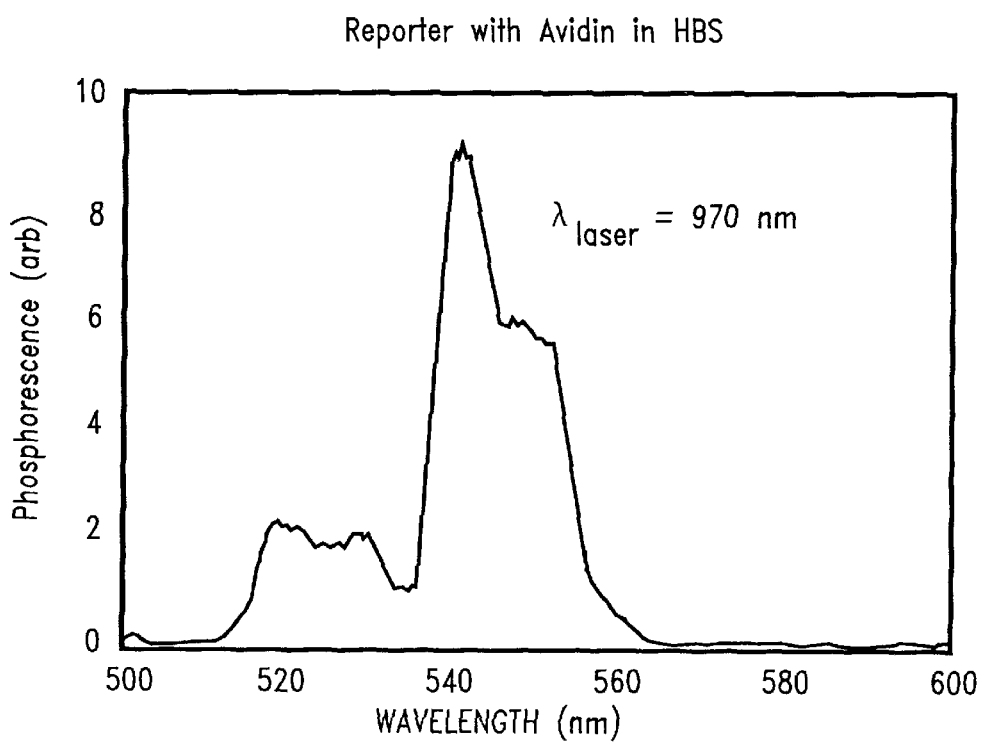
FIG. 17B shows a fluorescence spectrum scan of an up-converting phosphor reporter coated with streptavidin in Hepes-buffered saline induced by excitation with a 970-nm laser source.
Figure 18:
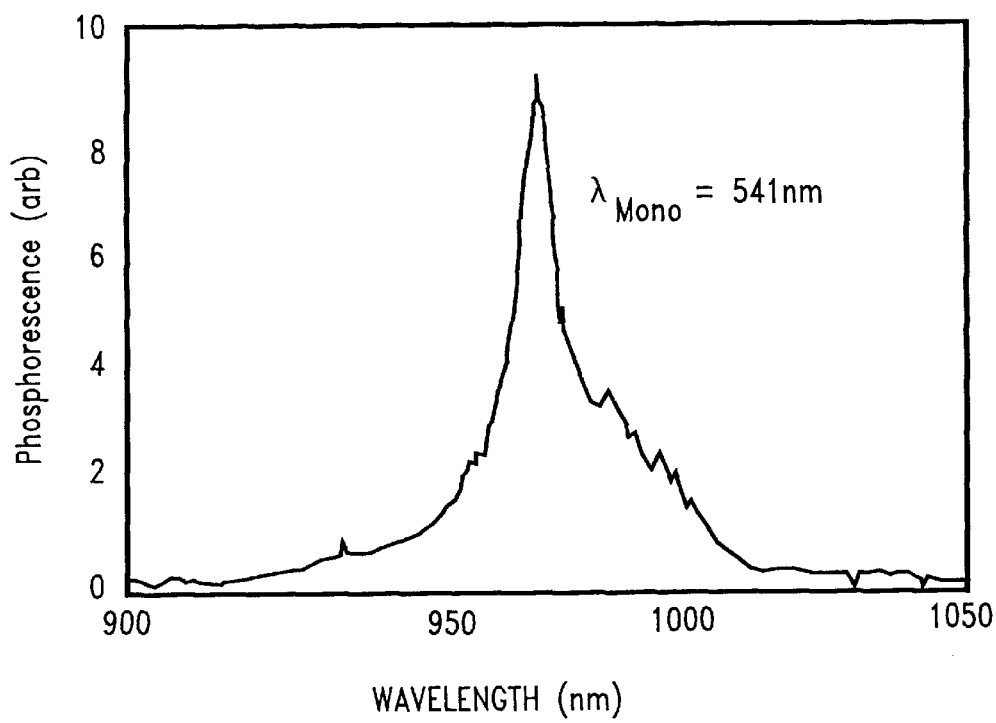
FIG. 18A shows an excitation spectrum scan of an up-converting phosphor reporter in Hepes-buffered saline with monochromatic detection of emission at 541 nm.
FIG. 18B shows an excitation spectrum scan of an up-converting phosphor reporter coated with streptavidin in Hepes-buffered saline with monochromatic detection of emission at 541 nm.
Figure 18:
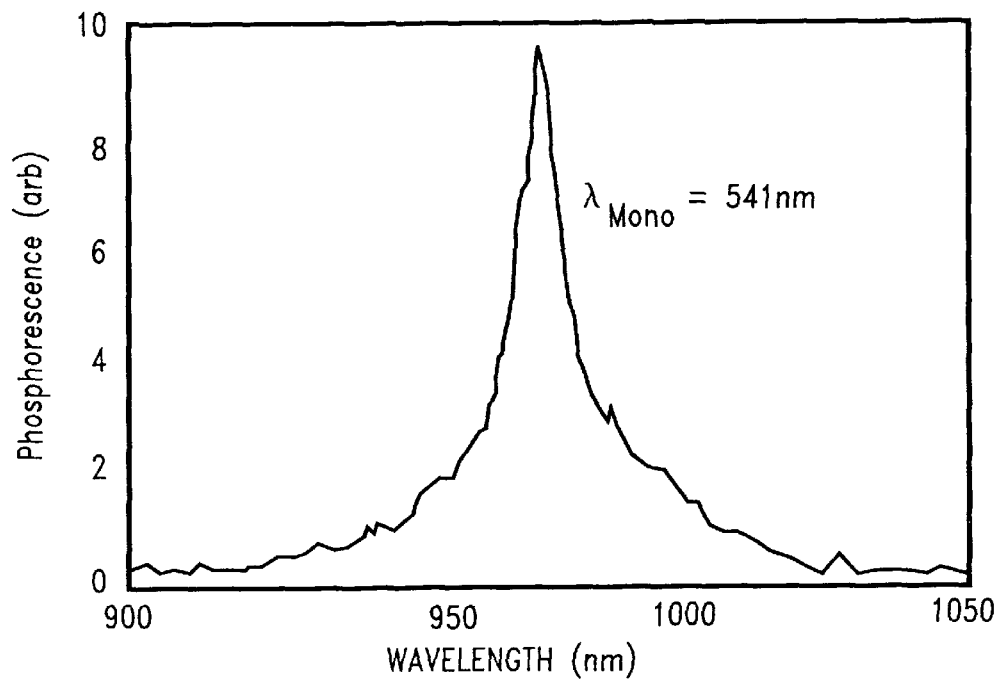

Phosphorescence efficiencies of submicron $Na(Y_{0.8}Yb_{0.12}Er_{0.08})F_4$ particles were measured. A Ti:sapphire laser was used as an excitation source and a spectrophotometer and photomultiplier was used as a detection system. Two types of measurement were performed. The first was a direct measurement in which the absolute emission per particle for phosphor suspensions was measured in emission bands at 540 nm and 660 nm. The calibrated cross-sections are shown in FIG. 15, and size-dependence is shown graphically in FIG. 16. This corresponded to a phosphorescence cross-section of approximately $1 \times 10^{-16}$ $cm^2$ for 0.3 $\mu m$ particles with excitation light at 975 nm and an intensity of approximately 20 $W/cm^2$. The emission efficiency of dry phosphor powder of about 25 $\mu m$ was also measured. On the basis of known values for the absorption cross-section of $Yb^{+3}$ in crystalline hosts (Lacovara et al. (1991) Op. Lett. 16: 1089, incorporated herein by reference) and the measured dependence of the phosphorescence emission on particle size, a phosphorescence cross-section of approximately $1 \times 10^{-15}$ $cm^2$ was found. The difference between these two measurements may be due to a difference in phosphorescence efficiency between dry phosphor and aqueous suspensions, or due to absorption of multiply scattered photons in the dry phosphor. On the basis of either of these cross-section estimates, the cross-section is sufficiently large to allow detection of single submicron phosphor particles at moderate laser intensities. At laser intensities of roughly 10 $W/cm^2$, the phosphorescence scales as the laser intensity to the 1.5 power.

Phosphor Particle Performance: Sensitivity of Detection

A series of Terasaki plates containing serial dilutions of monodisperse 0.3 $\mu m$ up-converting phosphor particles consisting of $(Y_{0.86}Yb_{0.08}Er_{0.06})_2O_2S$ were tested for up-conversion fluorescence under IR diode laser illumination in a prototype instrument.

The phosphor particles were prepared by settling in DMSO and were serially diluted into a 0.1% aqueous gum arabic solution. This appeared to completely eliminate any water dispersion problems. The serial dilutions used are listed in Table III.

TABLE III

| Label | Phosphor Loading (ng/well) | Phosphor Loading (particles/well) | Equivalent Detection Sensitivity (M) |
| --- | --- | --- | --- |
| $10^0$ | 1700 ± 90 | 23,600,000 ± 1,200,000 | $4 \times 10^{-12}$ |
| $10^{-1}$ | 170 ± 9 | 2,360,000 ± 120,000 | $4 \times 10^{-13}$ |
| $10^{-2}$ | 17 ± 0.9 | 236,000 ± 12,000 | $4 \times 10^{-14}$ |
| $10^{-3}$ | 1.7 ± 0.09 | 23,600 ± 1,200 | $4 \times 10^{-15}$ |
| $10^{-4}$ | 0.170 ± 0.009 | 2,360 ± 120 | $4 \times 10^{-16}$ |
| $10^{-5}$ | 0.017 ± 0.0009 | 236 ± 12 | $4 \times 10^{-17}$ |
| $10^{-6}$ | 0.0017 ± 0.00009 | 23.6 ± 1.2 | $4 \times 10^{-18}$ |

The stock DMSO dispersion had a phosphor density of 1.70±0.09 mg/mL (at 95% confidence limits), determined gravimetrically by evaporating 4-1 mL samples. This translates to $23.6 \times 10^9$ particles/mL (assuming an average particle size of 0.3 $\mu m$ and particle density of 5.3 g/mL). The residue after evaporating the samples over the weekend at 110°–120° C. was noticeably yellow, but did phosphoresce when tested with an IR diode laser.

Visual green light emanated from all serial dilutions down to $10^{-3}$ (i.e., 1.7 $\mu g/mL$ or $23.6 \times 10^6$ particles/mL) in a 1 mL polypropylene microfuge tube using a hand-held diode laser in a dark room. The $10^{-1}$ and $10^{-2}$ dilutions were visibly cloudy. Either 1 $\mu l$ of each serial dilution, or 0.1 $\mu l$ of the next higher dilution, were pipetted into a well on the Terisaki plate. It was found that 1 $\mu l$ fills the bottom of the well and 0.1 $\mu l$ spreads along the edge of the well, but does not cover the entire surface. Because of the statistical and pipetting problems associated with small volumes with low particle concentrations, 2 to 4 replicates were prepared of each dilution.

The well of a Terasaki plate holds a 10 $\mu l$ sample volume. Assuming all the phosphor particles contained in this volume adhere to the bottom of the sample well, we can estimate an equivalent detection sensitivity (Table III). It should be noted that $10^{-15}$ to $10^{-18}$ M is the normal range of enzyme-linked surface assays.

Control Sample Results

The control samples were scanned using a prototype up-conversion fluorimeter device (David Sarnoff Research Center). The samples were scanned by moving the plate in 50 $\mu m$ increments, using a motorized X-Y positioning stage, relative to the focal point of an infrared diode laser.

The IR diode laser was operated at 63 mW (100 mA). The beam was focused to $2.4 \times 10^{-3}$ cm$^2$ at the focal point. As the bottom of the sample well is about $1.4 \times 10^{-2}$ cm$^2$ (1365 µm diameter), the beam covers less than 17% of the well bottom surface at any individual position. The well also has sloping side walls which widen from bottom to top of the sample well and are also interrogated by a progressively divergent laser beam. Neglecting losses in the optics, the IR light intensity at the focal point (bottom of the sample well) was approximately 26–27 W/cm$^2$ at 980 nm wavelength. A photomultipler tube (PMT) was used for detection of the visible (upconverted) light emitted from the sample. Since the laser beam width was smaller than the surface area at the bottom of the sample well, the plate was aligned by visual inspection against the focal point of the diode laser so that the laser was centered in the middle well (C6 when reading wells C5, C6 and C7, and D6 when reading wells D5, D6, and D7).

Figure 19:
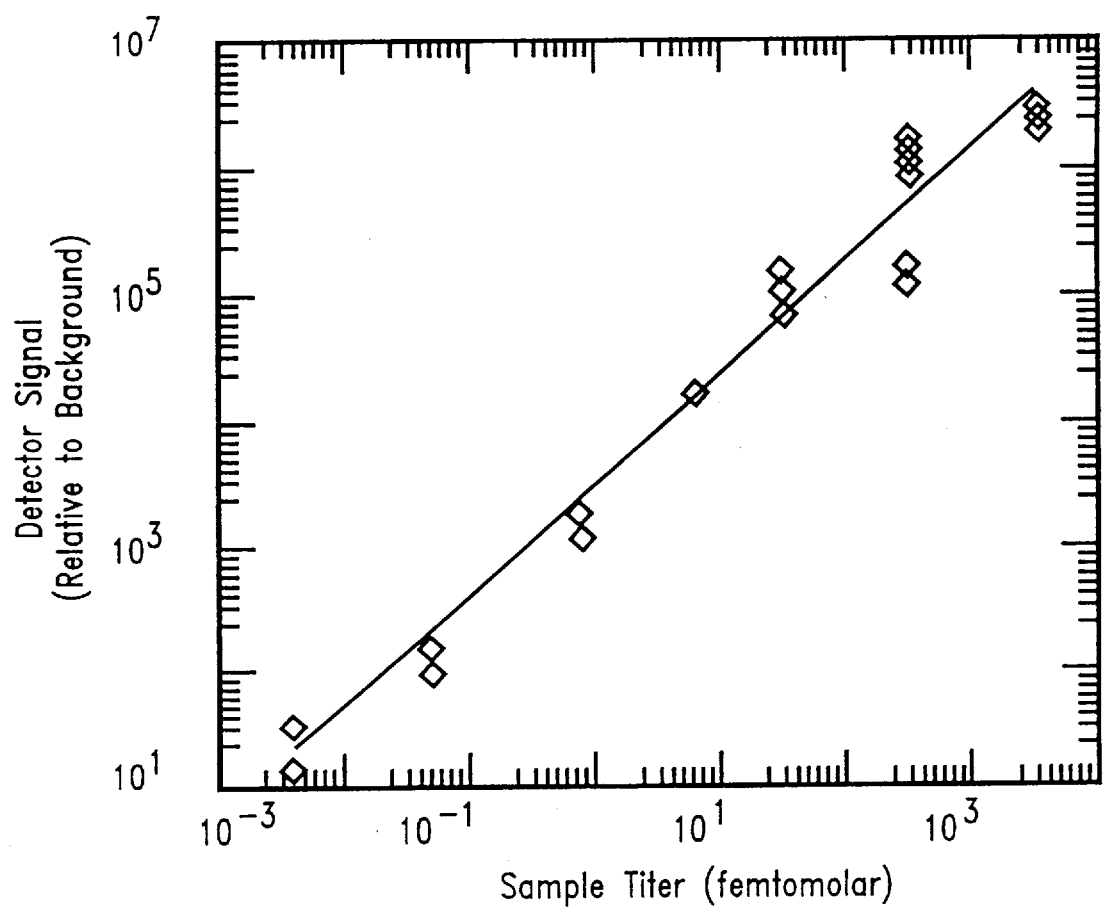
FIG. 19 shows the integrated signal obtained from samples of (Y$_{0.86}$Yb$_{0.08}$Er$_{0.06}$)$_2$O$_2$S showing the relationship between phosphor concentration and up-converted signal.

The PMT signal (amps) was recorded at each plate position and numerically integrated over the width of the sample well (approximately 4000 µm). Several scans were made at different positions in the $10^{-2}$ to $10^0$ dilution sample wells to determine the uniformity of the particle distribution. The background signal was determined by integrating the average dark field current of the PMT over a 4000 µm distance, which yields an integrated background signal of $1 \times 10^{-9}$ µa-m. The integration products of the samples wells were scaled to this background signal, and are shown in FIG. 19.

Immunodiagnostic Sample Detection

A series of IgG/anti-IgG samples for demonstrating the capabilities of the up-converting phosphor reporters in a immunosorbant assay format was prepared. These samples consisted of six individual wells (positive samples) coated with antigen (mouse IgG) and bovine serum albumin (BSA), and six wells coated with BSA alone (negative controls). Nominal 0.3 µm $(Y_{0.86}Yb_{0.8}Er_{0.06})_2O_2S$ phosphor particles coated with goat anti-mouse IgG antibody (anti-IgG) were then used as the reporter-antibody conjugate.

Six wells (C5, C6, C7, D5, D6, and D7) of a clear polystyrene Terasaki plate were coated with mouse IgG by incubating at 37° C. against 5 µL of a 100 µg/µL mouse IgG solution in phosphate buffered saline (PBS). After 1 h, this solution was aspirated off and each sample well was washed with 10 µL of 3% BSA in PBS. This was immediately aspirated off and replaced with 20 µL of 3% BSA in PBS. Each sample well was post-coated with BSA by incubating against the 20 µL of BSA/PBS solution for 1 h at 37° C. The post-coat solution was aspirated off and the plates stored at 4° C. overnight. These wells were considered in positive samples. The same six wells in a second Terasaki plate were prepared in an identical fashion, except they were not coated with mouse IgG. This second set of sample wells were considered negative controls.

Phosphor-Antibody Conjugate

A solution of $(Y_{0.86}Yb_{0.08}Er_{0.06})_2O_2S$ phosphor particles was prepared by suspending the dry phosphors into DMSO. The initial particle density was approximately $10^7$ particles/mL as determined by counting the number of particles contained in the field of an optical microscope. It should be noted that the 0.3 µm fundamental particle size was below the resolution limits of the microscope. This solution was allowed to settle undisturbed for 3 days. The supernatant, which was turbid and presumably contained mostly monodisperse smaller particles was used for subsequent conjugation.

Goat anti-mouse IgG antibody (Ab) was conjugated (by adsorption) onto the DMSO fractionated phosphor particles. This was done by mixing 200 µL of the Ab solution (in 0.1M Tris-HCl, pH 7.2) with 100 µL of the phosphor suspension in DMSO. Several different Ab concentrations were tried in the range of 0.025 to 1 µg/µL. A concentration of 0.25 µg/µL appeared to result in the most efficient coating (i.e., maximum Ab utilization with a minimum of clumping of the phosphor particles). The phosphors were equilibrated overnight at room temperature with the Ab in this DMSO/Tris solution with gentle agitation. The resulting phosphor-Ab conjugates were centrifuged from this solution and resuspended in a 3 µg/mL BSA solution in PBS for post-coating. The resulting BSA/PSA resuspension was used directly for the assay.

The degree of Ab adsorption to the phosphors, and residual Ab activity, was determined by titrating the phosphor-bound Ab with a fluorescein isothiocyanate (FITC) conjugated-mouse IgG. The resulting FITC-labeled phosphors were passed through a Cyteron Absolute flow cytometer, which was also capable of measuring the relative size of the particles. Two distinct size subpopulations were observed with about 65% of the counted particles appearing as small, presumably monodisperse particles, and 35% being significantly larger, presumably aggregates. Only 60% of the smaller subpopulation appeared to have significant quantities of active Ab (determined by FITC fluorescence). Of the purported aggregates, about 90% appeared to contain active Ab (by FITC fluorescence). This suggests that less than 40% of the phosphor-Ab conjugates were of an appropriate size (nominal 0.3 µm) and exhibited anti-mouse IgG activity. A similar fraction of phosphor-Ab conjugates (31%) were active but carried a significantly larger phosphor reporter.

The PMT signal (amps) was recorded at each plate position and numerically integrated over the width of the sample well (approximately 4000 µm). The average signals (with 95% confidence limits) are:

Average of Positive Samples=$1.30 \times 10^{-4} \pm 1.25 \times 10^{-4}$ µa-m

Average of Negative Controls=$4.20 \times 10^{-6} \pm 6.82 \times 10^{-6}$ µa-m

The positive samples and negative controls are statistically different at the 99.9% confidence level. The positive samples emit on average 30.0±29.7 times more light than the negative controls.

Linkage of Phosphors to Biological Macromolecules

In order to delineate further the parameters for up-converting phosphors as biochemical reporters, biological linkers were attached to phosphor particles. Sodium yttrium fluoride-ytterbium/erbium phosphor particles were coated with streptavidin. The excitation and emission spectral properties of the phosphor alone and the phosphor coated with streptavidin were measured (FIGS. 17A, 17B, 18A, and 18B) and both the uncoated and streptavidin-coated phosphors were almost identical in their absorption and emission properties, indicating that the attachment of macromolecular linkers (e.g., proteins) have little if any effect on the phosphorescent properties of the up-converting phosphor. The streptavidin-coated phosphors were then specifically bound to biotinylated magnetic beads, demonstrating the applicability of linker-conjugated inorganic phosphors as reporters in biochemical assays, such as immunoassays, immunohistochemistry, nucleic acid hybridizations, and other assays. Magnetic bead technology allows for the easy separation of biotin-bound streptavidin-coated phosphor from a solution, and is particularly well-suited for sandwich assays wherein the magnetic bead is the solid substrate.

Figure 20:
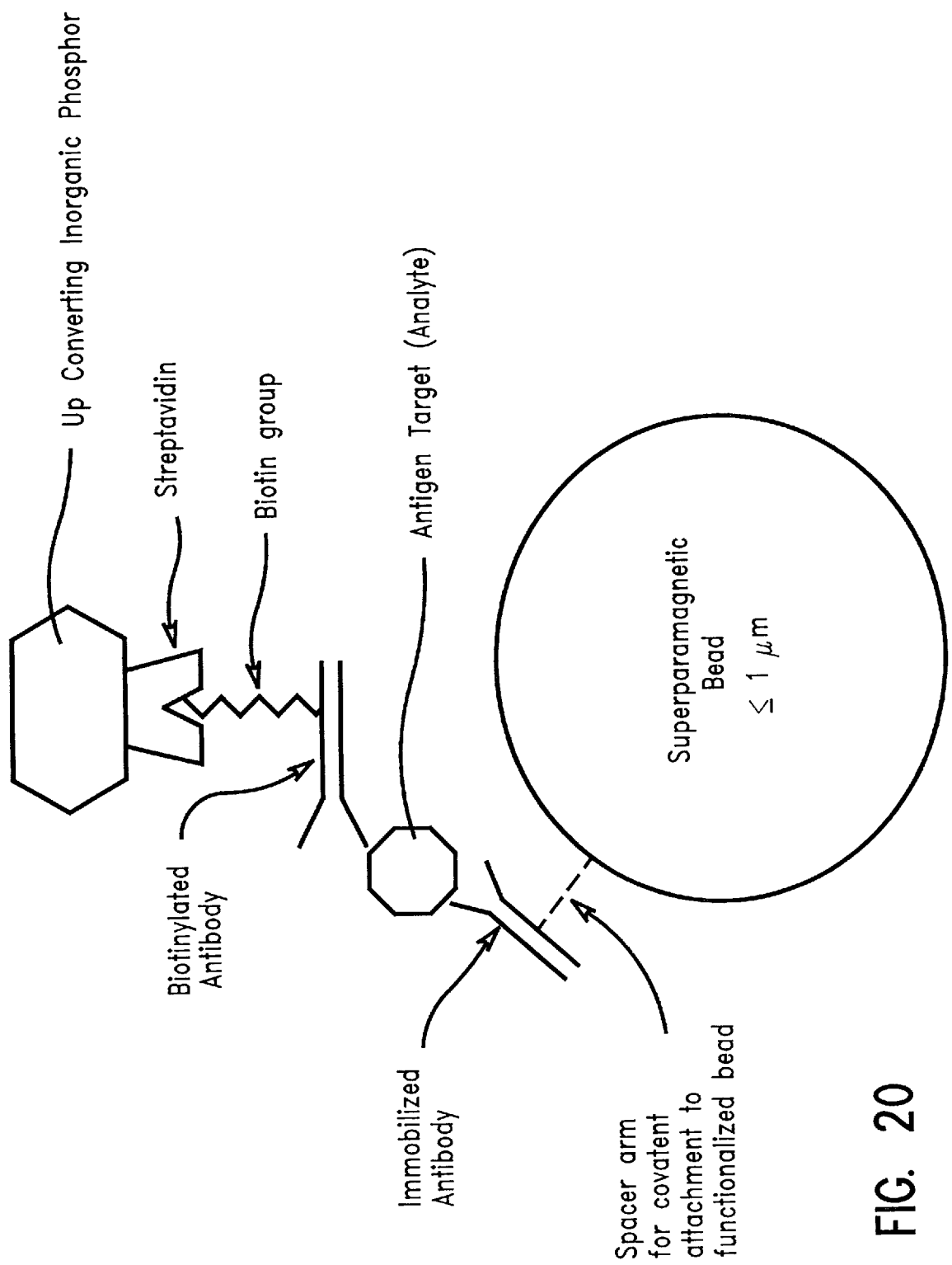
FIG. 20 shows schematically one embodiment of an sandwich immunoassay for detecting an analyte in a solution by binding the analyte (e.g., an antigen target) to a biotinylated antibody and to an immobilized antibody, wherein the analyte forms a sandwich complex immobilized on a solid substrate superparamagnetic microbead.

Advantageously, streptavidin-biotin chemistry is widely used in a variety of biological assays, for which up-converting phosphor reporters are suited. FIG. 20 shows schematically, for example and not limitation, one embodiment of an immunoassay for detecting an analyte in a solution by binding the analyte (e.g., an antigen target) to a biotinylated antibody, wherein the analyte forms a sandwich complex immobilized on a solid substrate (e.g., a magnetic bead) by linking a first binding component bound directly to the solid substrate to a second binding component (e.g., the biotinylated antibody); a streptavidin-coated up-converting phosphor then binds specifically to the biotinylated antibody in the sandwich and serves to report formation of the sandwich complex on the solid substrate (which is a measure of the analyte concentration). When the solid substrate is a magnetic bead, it is readily removed from the sample solution by magnetic separation and the amount of phosphor attached to the bead(s) in sandwich complex(es) are determined by measuring specific up-converting phosphorescence. Thus, sandwich complex phosphorescence provides a quantitative measure of analyte concentration.

Biotinylated polynucleotides are also conveniently used as hybridization probes, which can be bound by streptavidin-coated up-converting phosphors to report hybrid formation.

Background Phosphorescence in Biological Samples

Background signals were determined in two biological samples for determination of potential background in immunoassays. Sputum and urine were used as samples in the same apparatus as used for the phosphorescence sensitivity measurements (supra). No background levels were found above the system noise levels set by the photomultiplier dark current. This noise level allows detection of signals from on the order of a few hundred particles/cm$^3$. This is close to a single particle in the detection volume of the system.

A photomultiplier is a preferred choice for a detector for high sensitivity measurements of up-converting phosphors since photomultipliers can be selected to produce high quantum efficiency at the up-converted (i.e., emitted) wavelengths and virtually no response in the range of the longer excitation wavelengths.

Detection of Cell Antigens with Phosphor-Labeled Antibodies

Streptavidin is attached to the up-converting phosphor particles as described, supra. The mouse lymphoma cell line, EL-4, is probed with a hamster anti-CD3 antibody which specifically binds to the 30 kD cell surface EL-4 CD3 T lymphocyte differentiation antigen. The primary hamster antibody is then specifically bound by a biotinylated goat-antihamster secondary antibody. The biotinylated secondary antibody is then detected with the streptavidin-phosphor conjugate. This type of multiple antibody attachment and labeling is termed antibody layering.

Addition of multiple layers (e.g., binding the primary hamster Ab with a goat-antihamster Ab, followed by binding with a biotinylated rabbit-antigoat Ab) are used to increase the distance separating the phosphor from the target. The layering effect on signal intensity and target detection specificity is calibrated and optimized for the individual application by performing layer antibody layering from one layer (primary antibody is biotinylated) to at least five layers and ascertaining the optimal number of layers for detecting CD3 on EL-4 cells.

Figure 21:
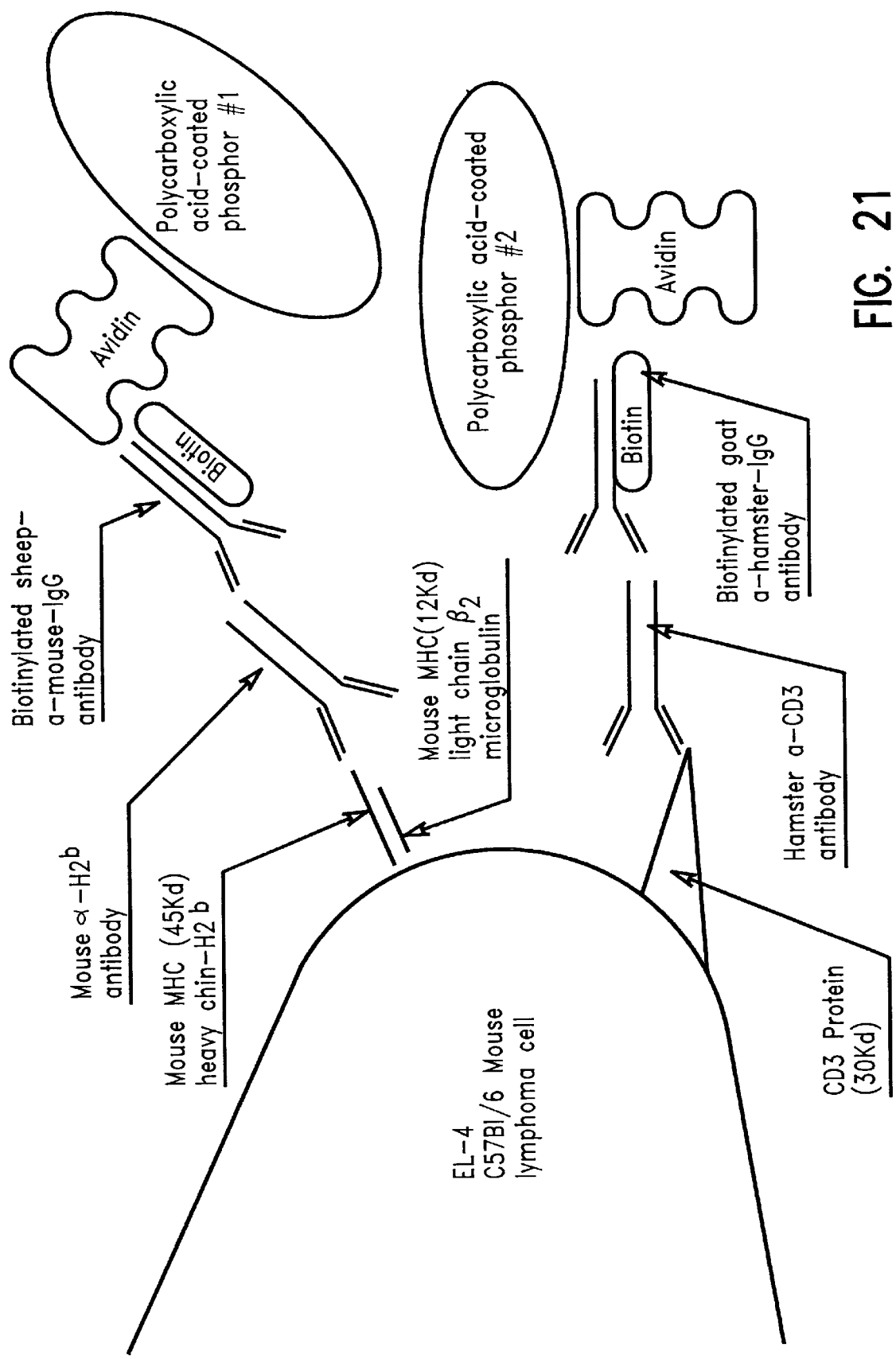
FIG. 21 shows schematically detection and discrimination of two cell surface antigens with specific antibodies labeled with two phosphors with distinct phosphorescence characteristics.

FIG. 21 schematically portrays simultaneous detection of two EL-4 cell surface antigens using phosphors which can be distinguished on the basis of excitation and/or emission spectra. Detection of both antigens in the scheme shown in FIG. 21 uses a biotinylated terminal antibody which is conjugated to streptavidin-coated phosphor (#1 or #2) prior to incubation with the Ab-layered sample. Thus, the phosphor-antibody specificity is retained through the unusually strong (KD approx. $1 \times 10^{15} M^{-1}$) non-covalent bond between streptavidin and biotin which is pre-formed before incubation with the primary antibody-bound sample. Quantitation of each antigen is accomplished by detecting the distinct signal(s) attributable to each individual phosphor species. Phosphorescent signals can be distinguished on the basis of excitation spectrum, emission spectrum, fluorescence decay time, or a combination of these or other properties.

Figure 22:
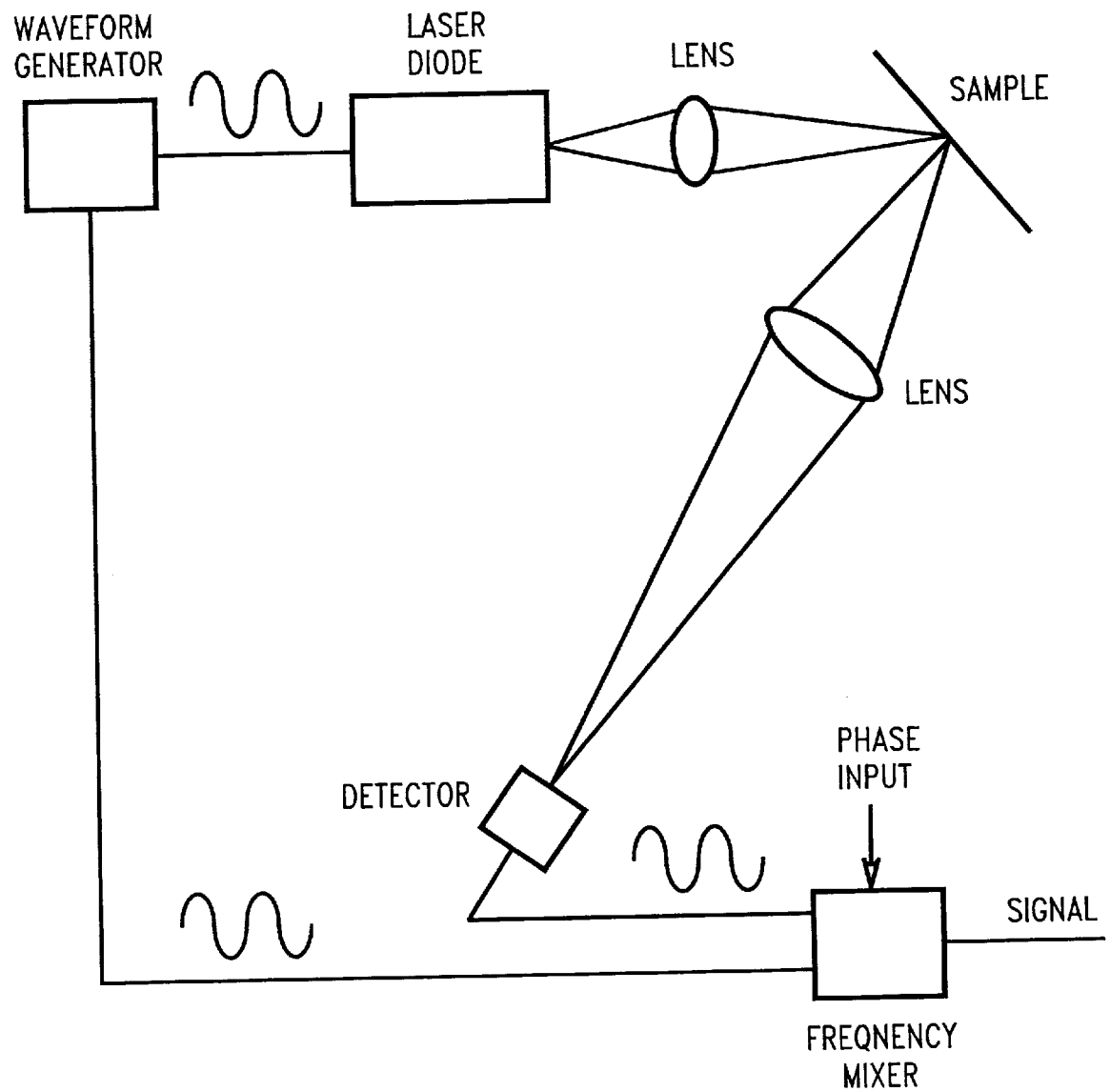
FIG. 22 shows a schematic of an apparatus for phase-sensitive detection.

FIG. 22 shows a schematic of an apparatus for phase-sensitive detection, which affords additional background discrimination. The pulse or frequency mixer is set to pass the signal and discriminate against the background following frequency calibration for maximum background rejection.

Covalent Conjugation of Upconverting Phosphor Label to Avidin

An upconverting yttrium-ytterbium-erbium ($Y_{0.86}Yb_{0.08}Er_{0.06}$) oxysulfide ($O_2S$) phosphor was linked to avidin by the following procedure:

Monodisperse upconverting phosphor particles were silanized with thiopropyltriethoxysilane (Huls) following the procedure detailed by Arkles (in: Silicone Compounds: Register and Review, Hills America, pgs. 59–75, 1991). This consisted of adding thiopropyltriethoxysilane (2 g) and 95% aq. ethanol (100 mL) to a 500 mL Erlenmeyer flask and stirred for 2 minutes. Approximately 8 mL of the 65 mg/mL phosphor suspension in DMSO was then added to the mixture. This suspension was stirred for an additional 2 minutes, then transferred to centrifuge tubes and centrifuged to separate the phosphor particles. The pellets were washed twice with 95% aq. ethanol centrifuging each time. The resulting particles were collected and dried overnight under vacuum at approximately 30° C. A quantity (127 mg) of dry silanized phosphors were resuspended in 1.5 mL of DMSO (phosphor stock).

A solution containing 1.19 mg of avidin (Pierce) in 1.0 mL of borate buffer (954 mg sodium borate decahydrate and 17.7 mL of 0.1N NCl in 50 mL of deionized water, pH 8.3) was prepared (Avidin stock). Another solution containing 1.7 mg of N-succinimidyl(4-iodoacetyl) aminobenzoate (Pierce Chemical) in 1.2 mL of DMSO was prepared (SIAB stock). A quantity (10 µL) of the SIAB stock was added to the 1.0 mL of Avidin stock and stirred at room temperature 30 min to allow the N-hydroxysuccimide ester of the SIAB to react with primary amines on the avidin (Avidin-SIAB stock).

A 20 mL scintillation vial was prepared containing 10 mL of borate buffer (pH 8.3). The following additions were then made to this vial: 21.6 µL of the avidin-SIAB stock solution followed by 1.5 mL of the phosphor stock. This reaction mixture was stirred at room temperature in the dark overnight to allow the SIAB activated avidin to react with the thiol groups present on the silanized phosphor surface and resulting in the covalent linkage of avidin to the phosphor particles.

After the overnight incubation 1.0 mL of the reaction mixture was centrifuged (1 min at 10,000 g) and the supernatant removed. The pellet was resuspended in 1.0 mL of phosphate buffered saline (pH 7.2, Pierce) and centrifuged again to wash any unconjugated protein from the phosphors. This washing process was repeated. The washed pellet was resuspended in 1.0 mL of phosphate buffered saline and used directly in diagnostic assays as described below.

Measurement Apparatus

A modified SLM Aminco 48000 Fluorimeter was used to measure the fluorescence spectrum from the phosphor samples. The modifications to this device consisted of adding a laser diode (David Sarnoff CD-299R-FA #13) which was input to the fluorimeter through port 3. The laser diode emits at $\lambda=985.1$ nm. Spectral data provided by the David Sarnoff Research Center also shows a small peak at 980.2 nm. This peak has 15% the intensity of the peak at 985 nm.

A 5.08 cm focal length lens was used to collimate the diode laser beam. The power of the IR laser light was measured as 6.1 mW at the cuvette location with a drive current of 75 mA. The beam was not focused at the center of the cuvette. This is true for the standard visible light from the fluorimeter excitation monochromator as well. The laser diode beam is diverging as it enters the cuvette holder and is approximately 4 mm (H)×2 mm (V) by the time it reaches the center of the cell, neglecting the changes in refractive index of the cell wall and the liquid.

Light emitted is scanned with a monochromator and detected by a photomultiplying tube (PMT) 90° from the direction of the excitation light. The detection limits for the modified SLM Aminco 48000 were determined by serial dilution to be $4\times10^{-16}$M (240,000 phosphor particles per mL) in PBS. Phosphor emission peaks in the spectrum were seen at wavelengths of 406±2 nm, 434±2 nm, 522±2 nm, and 548±2 nm. The largest peak was at 548 nm. The intensity of the 548 nm peak was used to discriminate samples.

Linkage of Avidin-Phosphor Conjugate to Cell Surface Marker

A lymphoblastoid cell line (Human Genetic Mutant Cell Repository #GM07092) was cultured in RPMI 1640 media containing 15% heat inactivated fetal calf serum. A suspension of cells ($10^7$ cells) was centrifuged and resuspended in an equal volume of phosphate buffered saline (PBS) pH 7.4. Cells were washed two times in PBS and resuspended to a final concentration of $5\times10^6$ cells/ml. These cells were then incubated with a mouse IgG1 monoclonal antibody to human $\beta_2$-microglobulin, a Class I histocompatibility antigen in polystyrene centrifuge tubes. The cells were immunoprecipitated for 30 minutes at 4° C. with an antibody concentration of 10 μg/ml. The cells were harvested by centrifugation, washed twice in PBS, resuspended in PBS and then aliquoted (250 μL) into six fresh centrifuge tubes. Four of these samples received biotinylated goat anti-mouse IgG, while the remaining two received FITC-labelled goat anti-mouse IgG. These immunoprecipitations were performed at 4° C. for 30 minutes in volume of 400 μL with a final second antibody concentration of 20 μg/ml. The cells were harvested and washed in PBS as above but were resuspended in 50 μL of blocking buffer (0.2% purified casein in PBS, Tropix, Bedford, Mass.). The cell-antibody complexes were blocked in this solution for 30 minutes at room temperature and then transferred to fresh tubes.

A pre-blocked suspension (40 μL) of either avidin-Phosphor conjugate, avidin-FITC, avidin, or unconjugated Phosphor was added to four of the cell samples conjugated with the biotinylated anti-mouse IgG (H&L). In addition, an equal amount of pre-blocked avidin-Phosphor or unconjugated Phosphor was added to the remaining two cell samples immunoprecipitated with the non-biotinylated FITC-labelled anti-mouse IgG (H&L). The avidin reporter conjugates or negative controls were pre-blocked as follows. Avidin-Phosphor and Phosphor alone was diluted in blocking buffer by adding 10 μL of a 6.7 mg/ml suspension to a final volume of 100 μL. Avidin-FITC and the avidin alone controls were also diluted in blocking buffer by adding 27 μL of 2.5 mg/ml solution to a final volume of 100 μL. These reagents were blocked at room temperature for 3 hours with intermittent resuspension and then added to 50 μL of cells labelled with biotinylated or non-biotinylated second antibody. The avidin-biotin reactions were performed at room temperature for 30 minutes with occasional resuspension. The reactions were stopped by harvesting the cells by centrifugation and washing twice in blocking buffer. The samples were resuspended in 100 μL of blocking buffer and allowed to settle for 4–5 minutes. Slides for imaging were prepared by pipetting 5 μL of settled cells from the bottom of the tube. Cells were imaged by confocal laser microscopy under appropriate conditions to observe cell surface FITC and up-converting phosphor signals. The observations are summarized in Table IV.

TABLE IV

| Tube | Type of goat anti-mouse IgG | Avidin Conjugate | Cell Surface Phosphor Signal | Cell Surface FITC Signal |
|---|---|---|---|---|
| 1 | biotinylated | Avidin-Phosphor | + | − |
| 2 | biotinylated | Phosphor | − | − |
| 3 | biotinylated | Avidin | − | − |
| 4 | biotinylated | Avidin-FITC | − | + |
| 5 | FITC labelled | Avidin-Phosphor | − | + |
| 6 | FITC labelled | Phosphor | − | + |

The remainder of the samples were used to resuspend paramagnetic, polystyrene beads bound with sheep anti-mouse IgG. For each of the six samples, $3\times10^7$ beads were pre-washed with blocking buffer for 1 hour at room temperature in Eppendorf tubes. The buffer was removed by aspiration while the tubes were in a magnetic rack. The magnetic beads with anti-mouse IgG were allowed to bind to the antibody labelled cells for 1 hour at room temperature with intermittent resuspension. The magnetic beads were then collected on a magnetic rack, washed four times in blocking buffer, resuspended in 100 μL blocking buffer, transferred to a fresh tube, and up-converting phosphorescence was measured on the fluorimeter.

To scan for phosphor emission, the emission monochromator bandwidth was set to 8 nm and the spectra were scanned from 500 to 700 nm with a step size of 2 nm. Samples were also measured for FITC signal by exciting the samples with 37 μM at $\lambda=490$ nm with a 2 nm bandwidth. Since the excitation wavelength (490 nm) and the emission wavelength (514 nm) are very close for FITC, higher resolution was required to get separable signals than with phosphor labelling. The intensity of the 490 nm signal was 240 μW/cm² at the center of the well. FITC emission spectra were scanned at 0.5 nm increments from 450 nm to 750 nm with a 2 nm bandwidth on the emission monochromator. Sample 1 is the positive control and clearly yielded the highest emission signal. Sample 2 indicates that any non-specific adsorption of the phosphors to the sample is limited and is readily discriminated from signal attributable to avidin-conjugated phosphor and showing that avidin linked phosphors can specifically bind only when they are conjugated with the probe, in this example through the biotin-avidin linkage. Sample 3 is the negative control which contains no phosphors, only avidin. Sample 4 shows FITC-conjugated avidin. Although FITC signals were observed on the cell surface by laser microscopy, the signals were below the level of detection on the fluorimeter for measurement of FITC, and since there was no phosphor in the sample there was no significant phosphor signal. Samples 5 and 6 show that FITC-conjugated primary antibodies can be detected and that the presence of phosphor or avidin-phosphor does not significantly disrupt binding of the primary antibody to its target antigen.

Linkage of Avidin-Phosphor Conjugate to DNA

Plasmid DNA (25 μg) was nick translated in the presence of 20 mM dGTP, 20 mM dCTP, 20 mM biotin-14 DATP, 13 mM dTTP, and 7 mM digoxigenin-11 dUTP and purified by ethanol precipitation. The average size of the biotinylated, digoxygenin labelled fragments was estimated to be between 200–300 nucleotides as estimated by gel electrophoresis. Approximately 20 μg DNA was immunoprecipitated for 1 hour at 22° C. with 10 μg/ml mouse monoclonal anti-digoxigenin IgG1 solution (PBS) in a 200 μL volume. An equivalent reaction containing no DNA was also prepared. Each of the two samples were then aliquoted (50 μL) into three fresh Eppendorf tubes.

The avidin-conjugates were blocked for 1 hour at room temperature by diluting 500 μg of an avidin-phosphor suspension, unconjugated phosphor suspension, or avidin solution in 300 μL of blocking buffer. For each of the samples (summarized below in Table V) 50 μL of the anti-digoxigenin conjugates was added to 150 μL of pre-blocked avidin-conjugates or avidin and were incubated for 30 minutes at room temperature.

Unbound avidin-conjugates were removed by resuspending $3 \times 10^7$ paramagnetic beads linked with sheep anti-mouse IgG (pre-blocked in blocking buffer). After incubation for 30 minutes at room temperature with intermittent resuspension, the beads were separated on a magnetic rack and washed 4 to 6 times in PBS. The antibody-DNA bound beads were then measured on the fluorimeter.

The samples were scanned from 500 to 700 nm with a bandwidth of 8 nm and step size of 2 nm. Each PMT value reported (Table V) represents an average over 5 scans. Sample 1 is expected to provide the highest PMT signal since biotinylated DNA is present and can bind to the avidin-linked phosphors. Sample 2 indicates the level of nonspecific adsorption of the phosphors to the sample which is found to be insignificant since the PMT signal is observed to be the same as that of the negative control (sample 4) which contains no phosphors. Sample 3 is another control and shows that the avidin-linked phosphors do not bind to the paramagnetic beads in the absence of DNA. Samples 5 and 6 show results of FITC-labeled avidin used to validate assay.

TABLE V

Upconverting Phosphor Nucleic Acid Diagnostic Assay Results

| Sample | DNA | Reporter | PMT Signal (V @ 546 nm) | PMT Signal (V @ 514 nm) |
|---|---|---|---|---|
| 1 | DNA labeled with digoxigenin and biotin | Avidin linked Phosphor | 6.1297 | 2.4788 |
| 2 | DNA labeled with digoxigenin and biotin | Silanized Phosphor | 1.0528 | 4.4022 |
| 3 | No DNA | Avidin linked Phosphor | 1.6302 | 3.5779 |
| 4 | DNA labelled with digoxigenin and biotin | Avidin | 0.8505 | 2.8067 |
| 5 | DNA labelled with digoxigenin and biotin | FITC-Avidin | 1.0484 | 8.4394 |
| 6 | No DNA | FITC-Avidin | 1.0899 | 3.5779 |

Phosphor Downconversion Evaluation

A sample of the $(Y_{0.86}Yb_{0.08}Er_{0.06})_2O_2S$ phosphors were scanned for the presence of a downconverted signal. This was accomplished by exciting a sample of the monodisperse phosphors described above ($4 \times 10^{-12}$M in DMSO) with 1.3 mW of monochromatic light at 350 nm with a 16 nm bandwidth for the excitation source. Detection was accomplished by scanning this sample from 350 to 800 nm with a monochomator bandwidth of 8 nm. Scanning was performed in 2 nm increments. No downconversion was observed. Moreover, no downconversion was seen at the excitation wavelengths cited by Tanke et al. (U.S. Pat. No. 5,043,265). Thus, the upconverting phosphors tested are unlike those reported in Tanke et al.

HOMOGENEOUS ASSAYS

The multiphoton activation process characteristic of upconverting phosphors can be exploited to produce assays that require no sample washing steps. Such diagnostic assays that do not require the removal of unbound phosphor labels from the sample are herein termed homogeneous assays, and can also be termed pseudohomogeneous assays.

Homogeneous Assay Example 1

Figure 23:
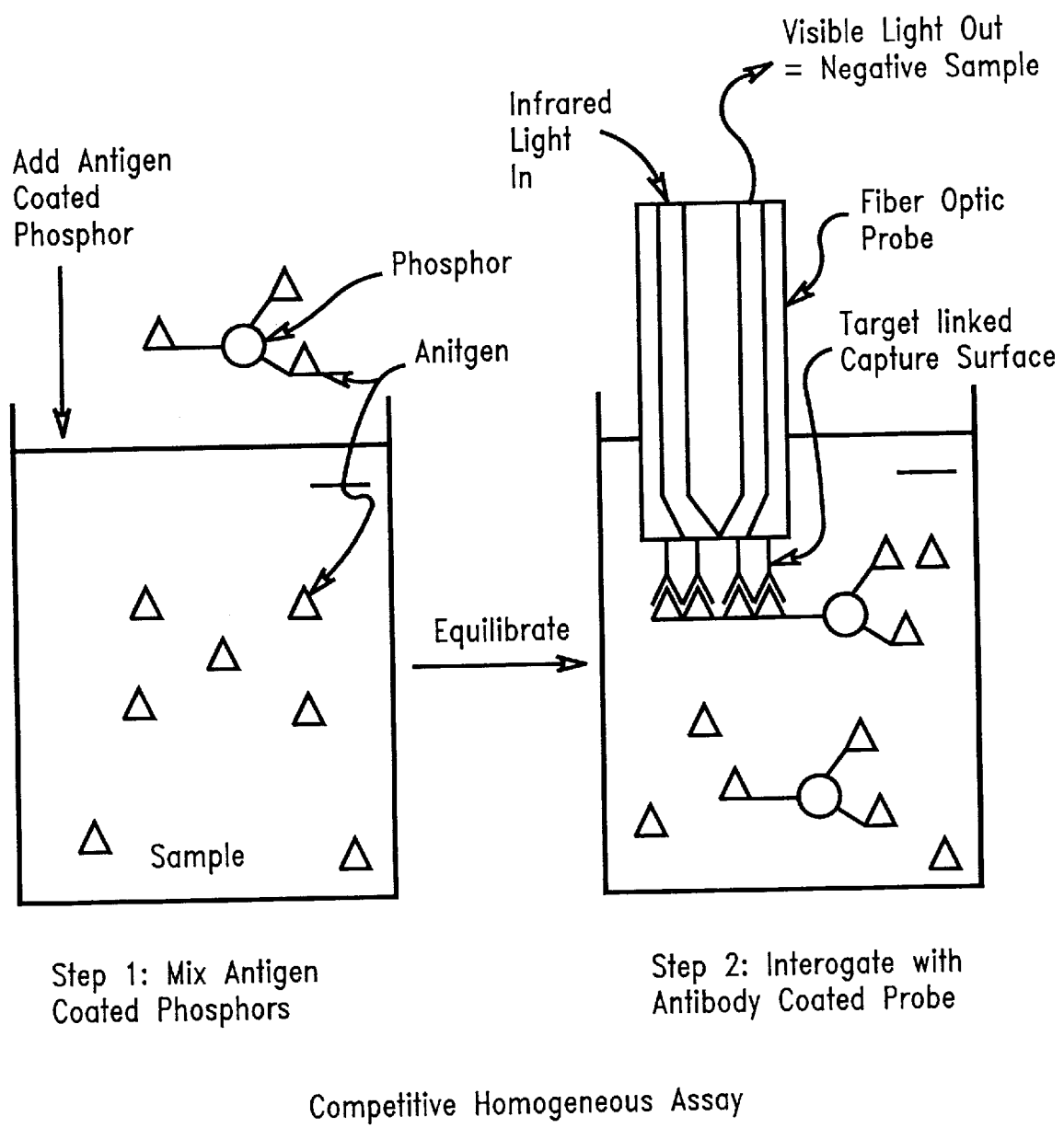
FIG. 23 show a schematic of a competitive homogeneous assay using phosphors as labels and fiber optic illumination at a capture surface.
Figure 24:
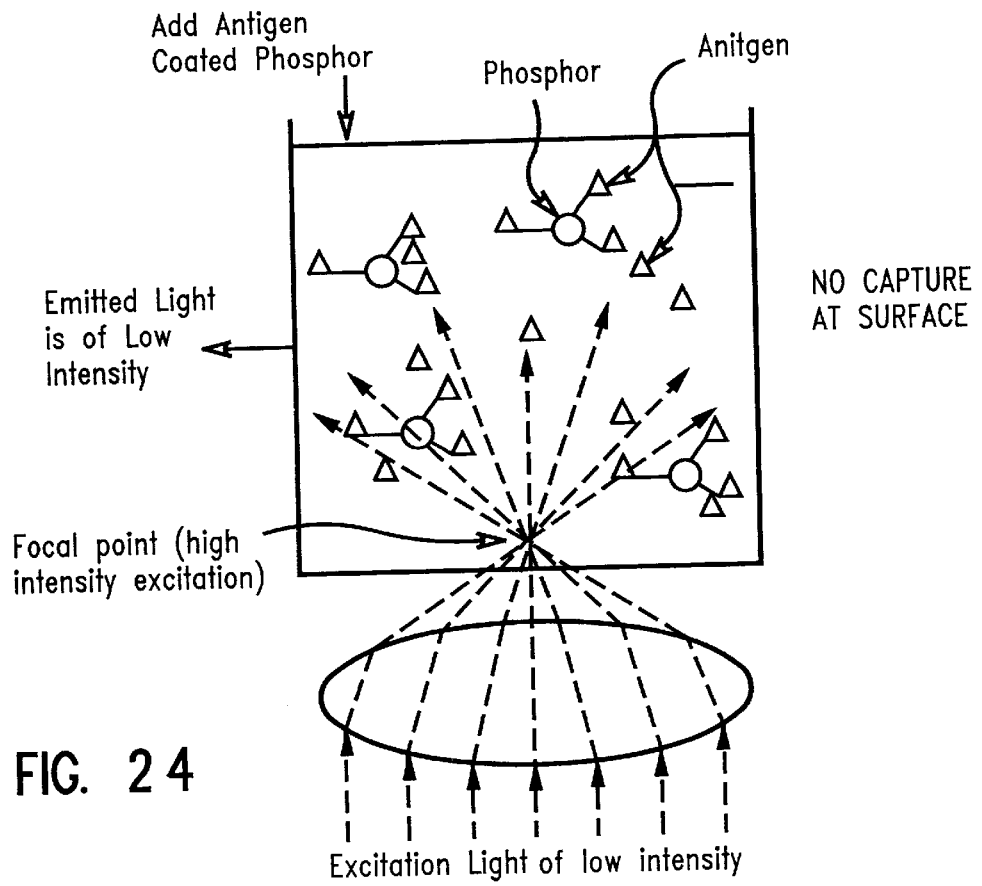
FIG. 24A & FIG. 24B show a schematic of a competitive homogeneous antigen capture assay using phosphors as labels and a convergent illumination beam focused on the capture surface.
Figure 24:
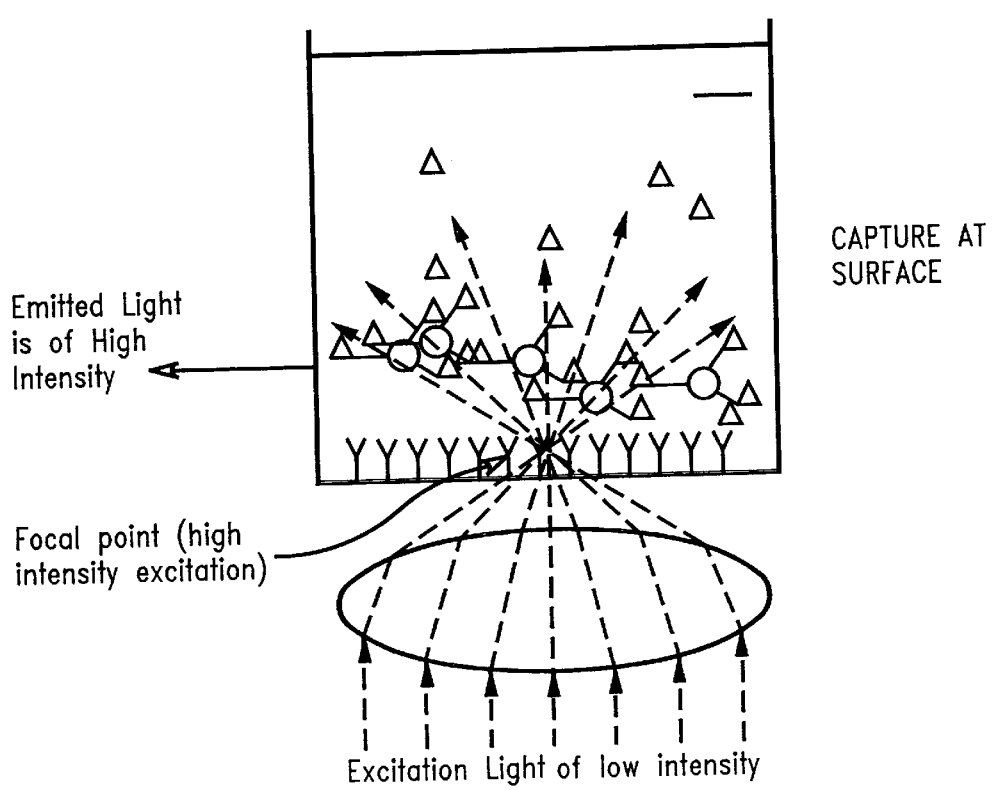

One embodiment of a homogeneous assay consists of the use of an upconverting phosphor label linked to an appropriate probe (e.g., an antibody or DNA). The phosphor-labeled probe specifically binds to a target (e.g., antigen or nucleic acid) that is linked to a capturing surface. A suitable capture surface can be the tip of a light carrying optical fiber (FIG. 23) or the bottom surface of a sample container (FIG. 24A and 24B). Upon incubation of the target-labelled capture surface with the phosphor-labelled probe, phosphor particles will accumulate at the capture surface as a function of the amount of target present on the capturing surface. The target may be linked directly to the capturing surface or may be immobilized by interaction with a binding agent (e.g., specific antibody reactive with target, polynucleotide that binds target) that is itself linked to the capturing surface (such as in a sandwich immunoassay, for example).

Detection of the phosphor bound to the capture surface is effected using an excitation light that is focused from a low intensity beam of large cross-section to a high intensity beam of small cross-section with the focal point of the beam being at or very near the capture surface. Focusing of the excitation light is accomplished by transmission through optical elements that have a very small focal length, such that the beam diverges and becomes less intense, within a short distance of the capture surface.

Since the intensity of the light emitted from the upconverting phosphor labels is proportional to the excitation light intensity raised to a power of two or greater, phosphors near the focal point of the excitation source will emit significantly more light than those remaining in suspension in the sample away from the capture surface. Therefore, binding of upconverting phosphor linked probes to the capture surface will yield an increase in emitted light intensity measured from the sample as a whole or as measured from a control sample in which phosphors do not bind to the capture surface. Emitted light intensity may be plotted as a function of target concentration using for standardization (calibration) a series of samples containing predetermined concentrations of target. The emitted light intensity from a test sample (unknown concentration of target) can be compared to the standard curve thus generated to determine the concentration of target.

Examples of suitable homogeneous assay formats include, but are not limited to, immunodiagnostic sandwich assays and antigen and/or antibody surface competition assays.

Homogeneous Assay Example 2

Figures 25A, 25B:
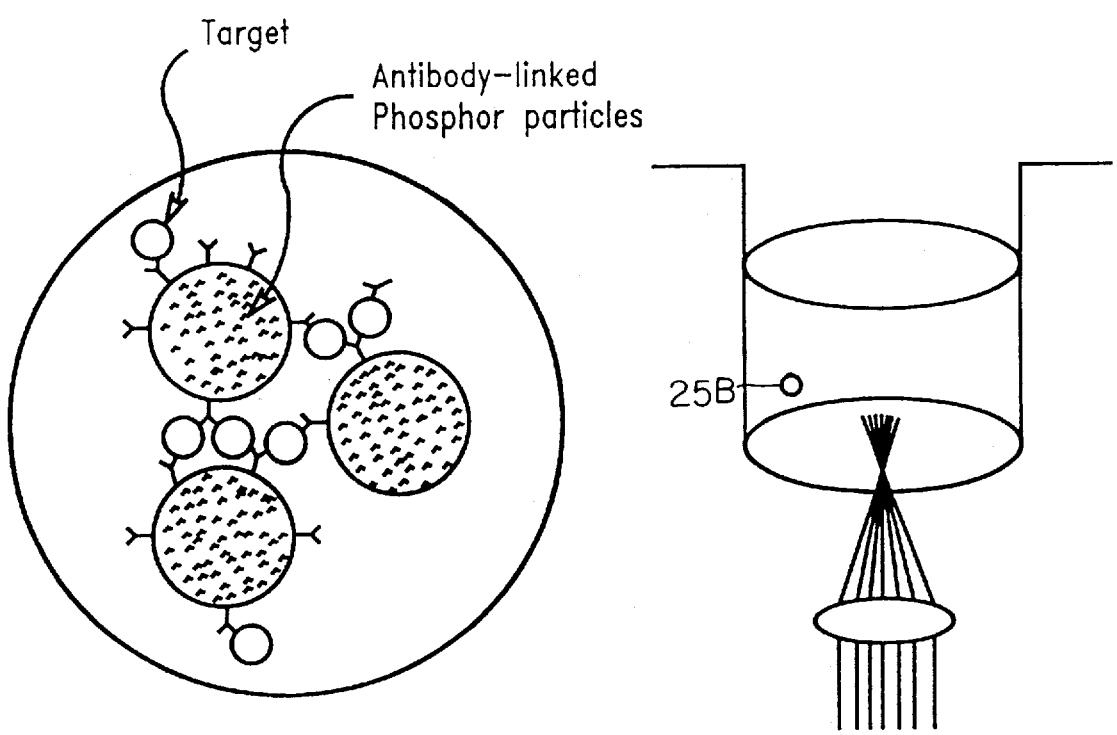
FIG. 25 shows a schematic of a homogeneous immunoprecipitation assay using phosphors as labels and a convergent illumination beam focused on the capture surface wherein the capture surface collects immunoprecipitates.

Another embodiment allows for the accumulation of upconverting phosphor linked probes at the detection surface by the application of centrifugal or gravitational settling. In this embodiment an upconverting phosphor is linked to multiple probes. All the probes must bind to the same target, although said binding can be accomplished at different locations (e.g., as antibody probes may target different epitopes on a single antigen). The multiprobe phosphor can then be used to effect the aggregation of targets in solution or suspension in the sample. This aggregation will result in the formation of a large insoluble phosphor-probe-target complex that precipitates from solution or suspension (FIG. 25). The aggregated complex containing phosphors accumulates at a detection surface while nonaggregated material remains in solution or suspension. Detection is accomplished as described in the above example using a sharply converging excitation beam.

Evaluation of Up-Converting Chelates

Up-conversion has been performed in rare earth chelates and rare earth salt solutions. Chelates of erbium and neodymium have been prepared with ethylenediaminetetraacetic acid (EDTA) and dipicolinic acid (DPA). The erbium chelates were pumped using light near 793.5 nm from a Ti:sapphire laser (the excitation scheme of Macfarlane (1989) *Appl. Phys. Lett* 54: 2301). This approach produced upconversion but not satisfactorily, which we attribute to weak absorption for the first step due to the increase in linewidth in the chelate over the low temperature crystal used for the up-conversion laser.

Figure 32:
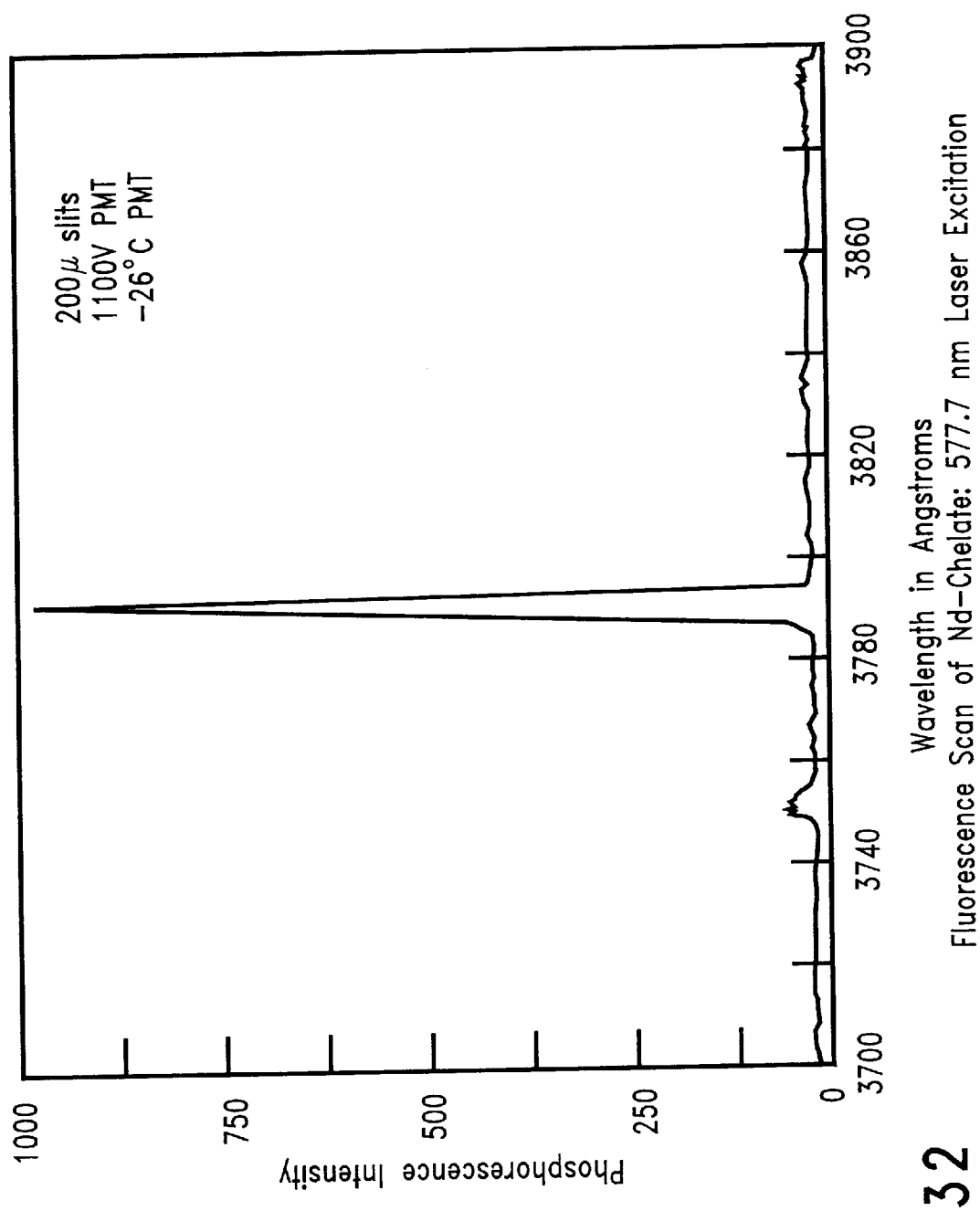
FIG. 32 is an emission spectrum for up-conversion from neodymium chelated in EDTA.

The neodymium chelates were excited with light near 580 nm from a Nd:YAG-pumped dye laser (following the excitation scheme of Macfarlane et al. (1988) *Appl. Phys. Lett* 52: 1300). An emission spectrum for the emitted up-converted light at 380 nm is shown in FIG. 32. We estimate the up-conversion cross section to be $10_{570}$-27 >> $cm_{570}2$>> for this experiment.

We have also observed up-conversion in thulium acetate hexahydrate and holmium chloride hexahydrate in solution following the excitation schemes of Allain et al. (1990) *Electron. Lett.* 26: 166, and Allain et al. (1990) *Electron. Lett.* 26: 261, respectively. The salts were dissolved in heavy water, and excitation was performed using a krypton laser. Although the up-conversion was weak, the up-conversion should be improved if chelated compounds are used instead of dissolved salts.

Although the present invention has been described in some detail by way of illustration for purposes of clarity of understanding, it will be apparent that certain changes and modifications may be practiced within the scope of the claims.

We claim:

1. A method for detecting an analyte in a sample, comprising the steps of:

contacting a sample containing a target analyte with a labeled probe to specifically bind the target analyte and form a labeled probe-target complex, wherein the labeled probe comprises a probe attached to an up-converting chelate complex comprising a rare earth ion and a ligand and being capable of converting excitation radiation to emission radiation of a shorter wavelength;

separating any bound labeled probe from the labeled probe-target complex;

illuminating the labeled probe-target complex with excitation radiation; and detecting emission radiation of at least one label emission wavelength, wherein the emission radiation has a shorter wavelength than the excitation radiation.

2. A method of claim 1, further comprising, before the contacting step, the step of attaching the up-converting chelate complex to the probe to form the labeled probe.

3. A method according to claim 1, wherein the rare earth ion is selected from the group of an erbium ion, neodymium ion, thulium ion, a holmium ion and a praseodymium ion.

4. A method according to claim 3, wherein the ligand is selected from the group ethylenediaminetetraacetic acid, dipicolinic acid, diethylenetriaminetetraacetic acid, diethylenetriaminepentaacetic acid, tetraazacyclotetradecanetetraacetic acid, an antibiotic, a protein, a phthalocyanine and a cryptate.

5. A method for detecting an analyte in a sample, comprising the steps of:

contacting a sample containing a target analyte with a probe to specifically bind the target analyte and form a probe-target complex;

contacting the probe-target complex with a label to form a labeled probe-target complex, wherein the label is an up-converting chelate complex comprising a rare earth ion and a ligand and being capable of converting excitation radiation to emission radiation of a shorter wavelength;

separating any unbound label from the labeled probe-target complex;

illuminating the labeled probe-target complex with excitation radiation; and detecting emission radiation of at least one label emission wavelength, wherein the emission radiation has a shorter wavelength than the excitation radiation.

6. A method for detecting an analyte in a sample, comprising the steps of:

contacting a sample containing a target analyte with a labeled probe to specifically bind the target analyte and form a labeled probe-target complex, wherein the labeled probe comprises a probe attached to an up-converting chelate complex comprising a rare earth ion and a ligand and wherein the up-converting chelate complex is capable of converting excitation radiation to emission radiation of a shorter wavelength;

differentiating the labeled probe-target complex from any unbound labeled probe in the sample;

illuminating the labeled probe-target complex with excitation radiation; and detecting emission radiation of at least one label emission wavelength from the labeled probe-target complex, wherein the emission radiation has a shorter wavelength than the excitation radiation.

* * * * *